(12) United States Patent
Cassayre et al.

(10) Patent No.: US 11,104,671 B2
(45) Date of Patent: *Aug. 31, 2021

(54) INSECTICIDAL COMPOUNDS

(71) Applicant: SYNGENTA PARTICIPATIONS AG, Basel (CH)

(72) Inventors: Jérôme Yves Cassayre, Stein (CH); Myriem El Qacemi, Stein (CH); André Stoller, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/496,758

(22) PCT Filed: Mar. 22, 2018

(86) PCT No.: PCT/EP2018/057344
§ 371 (c)(1),
(2) Date: Sep. 23, 2019

(87) PCT Pub. No.: WO2018/172477
PCT Pub. Date: Sep. 27, 2018

(65) Prior Publication Data
US 2020/0031817 A1 Jan. 30, 2020

(30) Foreign Application Priority Data

Mar. 23, 2017 (EP) .................................. 17162622

(51) Int. Cl.
C07D 413/12 (2006.01)
C07D 413/14 (2006.01)
C07D 417/12 (2006.01)
A01N 43/80 (2006.01)

(52) U.S. Cl.
CPC ........... *C07D 413/12* (2013.01); *A01N 43/80* (2013.01); *C07D 413/14* (2013.01); *C07D 417/12* (2013.01)

(58) Field of Classification Search
None
See application file for complete search history.

(56) References Cited

U.S. PATENT DOCUMENTS 10,588,317 B2 * 3/2020 Cassayre .............. C07D 413/14
2013/0338197 A1 12/2013 Mita et al.

FOREIGN PATENT DOCUMENTS

WO 2011067272 A1 6/2011
WO 201263959 A1 12/2012
WO 2017050922 A1 3/2017

OTHER PUBLICATIONS

International Search Report of International Patent Application No. PCT/EP2018/057344 dated May 15, 2018.

* cited by examiner

*Primary Examiner* — Alton N Pryor
(74) *Attorney, Agent, or Firm* — BakerHostetler; Toni-Junell Herbert

(57) ABSTRACT

The present invention relates to compounds of formula (I) wherein $A^1$, $A^2$, $A^3$, $A^4$, $R^1$, $R^2$, $R^3$, $R^4$ and n are as defined in claim 1; or a tautomer, isomer, enantiomer, salt or N-oxide thereof; to intermediates for preparing compounds of formula (I), to compositions comprising them and to methods of using them to combat and control insect, acarine, nematode and mollusc pests.

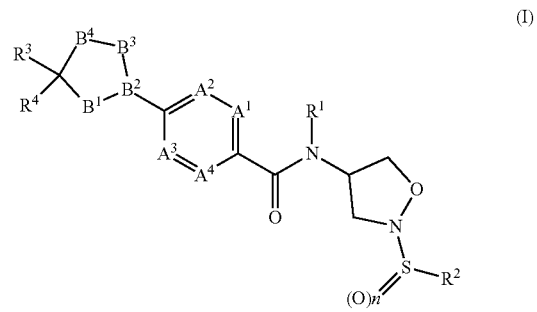

25 Claims, No Drawings

INSECTICIDAL COMPOUNDS

The present invention relates to certain isoxazolidine derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in WO2011067272.

It has now surprisingly been found that certain isoxazolidine, dihydrothiophene, dihydrolsothiazole, pyrrolidine and dihydrofurane derivatives have highly potent insecticidal properties.

The present invention provides, in a first aspect of the invention, compounds of formula (I)

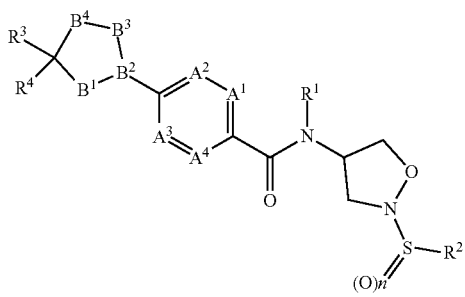

wherein $A^1$, $A^2$, $A^3$ and $A^4$ are independently of one another C—H, C—$R^5$, or nitrogen;

$B^1$-$B^2$-$B^3$-$B^4$ is —C($R^{5a}R^{5b}$)—C=N—O—, —CH$_2$—C=N—CH$_2$—, —CH$_2$—C=CH$_2$—S—, —CH$_2$—C=N—S—, —CH$_2$—N—CH$_2$—CH$_2$—, —CH$_2$—C=CH—O—, —CH(OH)—N—CH$_2$—CH$_2$—, —C(O)—N—CH$_2$—CH$_2$—, —CH$_2$—C=N—O— or —CH=C—CH$_2$—O—;

$R^1$ is hydrogen, $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl-, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl, $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group;

$R^2$ is $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —N($R^8$)($R^9$), —OR$^{10}$ or halogen;

$R^3$ is $C_1$-$C_8$haloalkyl;

$R^4$ is aryl, aryl substituted by one to three $R^7$, heteroaryl or heteroaryl substituted by one to three $R^7$;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge, a —CH$_2$—CH$_2$—CH$_2$— bridge, a —CH(OH)—CH$_2$—CH$_2$— bridge, a —C(O)—CH$_2$—CH$_2$— bridge, or a —N=CH—CH=CH— bridge;

$R^{5a}$ and $R^{5b}$ are, independently of each other, hydrogen, cyano, halogen, hydroxyl, $C_1$-$C_8$alkyl-, $C_1$-$C_8$alkyl- substituted by one to five $R^{6a}$, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, arylthio- or arylthio- wherein the aryl moiety is substituted by one to five $R^7$, arylsulfinyl- or arylsulfinyl- wherein the aryl moiety is substituted by one to five $R^7$, arylsulfonyl- or arylsulfonyl- wherein the aryl moiety is substituted by one to five $R^7$, heterocyclylthio- or heterocyclylthio- wherein the heterocyclyl moiety is substituted by one to five $R^7$, heterocyclylsulfinyl- or heterocyclylsulfinyl- wherein the heterocyclyl moiety is substituted by one to five $R^7$, or heterocyclylsulfonyl- or heterocyclylsulfonyl- wherein the heterocyclyl moiety is substituted by one to five $R^7$, $C_1$-$C_8$alkyl, $C_2$-$C_8$alkenyl, $C_2$-$C_8$alkynyl, $C_1$-$C_8$haloalkyl, $C_2$-$C_8$haloalkenyl, hydroxy, $C_1$-$C_8$alkoxy, $C_3$-$C_8$alkenyloxy, $C_3$-$C_8$alkynyloxy, or $C_1$-$C_8$haloalkoxy, provided that at least one of $R^{5a}$ and $R^{5b}$ is not hydrogen;

$R^{6a}$ is independently cyano, nitro, amino, $C_1$-$C_8$alkylamino, N,N—$C_1$-$C_8$dialkylamino, hydroxy, $C_1$-$C_8$alkoxy, or $C_1$-$C_8$haloalkoxy;

$R^{6b}$ is independently halogen, cyano, nitro, oxo, $C_1$-$C_8$alkyl, $C_1$-$C_8$haloalkyl, amino, $C_1$-$C_8$alkylamino, N,N—$C_1$-$C_8$dialkylamino, hydroxyl, $C_1$-$C_8$alkoxy, $C_1$-$C_8$haloalkoxy, phenyl, phenyl substituted by one to three $R^7$, 5-6 membered heteroaryl, 5-6 membered heteroaryl substituted by one to three $R^7$;

$R^7$ is independently halogen, cyano, nitro, $C_1$-$C_8$alkyl, $C_1$-$C_8$haloalkyl, $C_1$-$C_8$alkoxy, $C_1$-$C_8$haloalkoxy;

$R^8$ and $R^9$ are independently hydrogen, cyano, cyano-$C_1$-$C_8$alkyl, $C_1$-$C_8$alkyl, $C_1$-$C_8$alkyl substituted by one to three $R^{6a}$, $C_2$-$C_8$alkenyl, $C_2$-$C_8$alkenyl substituted by one to three $R^7$, $C_1$-$C_8$alkoxy, $C_1$-$C_8$haloalkoxy, $C_1$-$C_8$haloalkoxy substituted by one to three $R^7$, $C_1$-$C_8$alkoxy substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —S(O)$R^{10}$, —S(O)$_2R^{10}$, COR$^{10}$, COOR$^{10}$, or $R^8$ and $R^9$ together with the nitrogen atom can be linked through a $C_3$-$C_8$alkylene chain, a $C_3$-$C_8$alkylene chain substituted by one to three $R^{6b}$ or a $C_3$-$C_8$alkylene chain, where one carbon atom is replaced by O, S, S(O) or $SO_2$;

$R^{10}$ is hydrogen, cyano-$C_1$-$C_8$alkyl, $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or $SO_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$;

n is 1 or 2;

provided that if $B^1$-$B^2$-$B^3$-$B^4$ is —$CH_2$—C=N—O— then the only meaning of $R^5$ is that two $R^5$ on adjacent carbon atoms together form a —$CH_2$—$CH_2$—$CH_2$— bridge, a —CH(OH)—$CH_2$—$CH_2$— bridge or a —C(O)—$CH_2$—$CH_2$-bridge;

and an agrochemically acceptable salt, stereoisomer, enantiomer, tautomer and N-oxide thereof.

Compounds of formula (I) which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkylcarbonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

As used herein, the term "$C_2$-$C_8$alkynyl" refers to a straight or branched hydrocarbon chain radical group consisting solely of carbon and hydrogen atoms, containing at least one triple bond, having from two to eight carbon atoms, and which is attached to the rest of the molecule by a single bond. Examples of $C_2$-$C_8$ alkynyl include, but are not limited to, ethynyl, prop-1-ynyl, but-1-ynyl and but-2-ynyl.

As used herein, the term "$C_2$-$C_8$alkenyl" refers to a straight or branched hydrocarbon chain radical group consisting solely of carbon and hydrogen atoms, containing at least one double bond, having from two to eight carbon atoms, and which is attached to the rest of the molecule by a single bond. Examples of $C_2$-$C_8$alkenyl include, but are not limited to, prop-1-enyl, but-1-enyl and but-2-enyl.

As used herein, alkylcarbonyloxyalkyl refers to a group —ROC(O)R, wherein each R is, independently, $C_1$-$C_8$ alkyl.

As used herein, alkoxycarbonylsulfanyl refers to a group —SC(O)OR, wherein R is $C_1$-$C_8$ alkyl.

As used herein, alkylaminocarbonyloxyalkyl refers to a group —ROC(O)NHR, wherein each R is, independently, $C_1$-$C_8$ alkyl.

As used herein, dialkylaminocarbonyloxyalkyl refers to a group —ROC(O)NRR, wherein each R is, independently, $C_1$-$C_8$ alkyl.

As used herein, alkylaminocarbonylalkyl refers to a group —RC(O)NHR, wherein each R is, independently, $C_1$-$C_8$ alkyl.

As used herein, dialkylaminocarbonylalkyl refers to a group —RC(O)NRR, wherein each R is, independently, $C_1$-$C_8$ alkyl.

As used herein, alkoxycarbonylalkylaminoalkyl refers to a group —RNH(R)C(O)OR, wherein each R is, independently, $C_1$-$C_8$ alkyl.

Heteroaryl groups are preferably 5-6 membered heteroaryl or are 5-6 membered heteroaryl substituted by one to three $R^7$, where heteroaryl groups contain 1 to 3 hetero atoms selected from the group consisting of nitrogen, oxygen and sulfur, it not being possible for each ring system to contain more than 2 oxygen atoms and more than 2 sulfur atoms. Examples of monocyclic groups include pyridyl, pyridazinyl, pyrimidinyl, pyrazinyl, pyrrolyl, pyrazolyl, imidazolyl, triazolyl (e.g. 1.2.4 triazolyl), furanyl, thiophenyl, oxazolyl, isoxazolyl, oxadiazolyl, thiazolyl, isothiazolyl, tetrazolyl and thiadiazolyl.

The compounds of formula (I) according to the invention also include hydrates which may be formed during the salt formation.

Preferred values of $A^1$, $A^2$, $A^3$, $A^4$, $B^1$-$B^2$-$B^3$-$B^4$, $R^1$, $R^2$, $R^3$, $R^4$, $R^5$, $R^{5a}$, $R^{5b}$, $R^{6a}$, $R^{6b}$, $R^7$, $R^8$, $R^9$, and $R^{10}$, in relation to each compound of the present invention, including the intermediate compounds, are, in any combination (including combinations of preferred values with the original values) as set out below.

Preferably no more than two of $A^1$, $A^2$, $A^3$ and $A^4$ are nitrogen.

Preferably $A^1$ is C—H or C—$R^5$; more preferably $A^1$ is C—$R^5$.

Preferably $A^2$ is C—H or C—$R^5$; more preferably $A^2$ is C—H.

Preferably $A^3$ is C—H or N; more preferably $A^3$ is C—H.
Preferably $A^4$ is C—H or N; more preferably $A^4$ is C—H.
Preferably each of $A^2$, $A^3$ and $A^4$ are C—H and $A^1$ is C—$R^5$.

Preferably $B^1$-$B^2$-$B^3$-$B^4$ is —CH=C—CH$_2$—O—.
Preferably $B^1$-$B^2$-$B^3$-$B^4$—CH$_2$—C=CH—O—.
Preferably $B^1$-$B^2$-$B^3$-$B^4$ is —CH$_2$—N—CH$_2$—CH$_2$—.
Preferably $B^1$-$B^2$-$B^3$-$B^4$ is —CH$_2$—C=N—S—.
Preferably $B^1$-$B^2$-$B^3$-$B^4$ is —CH$_2$—C=CH$_2$—S—.
Preferably $B^1$-$B^2$-$B^3$-$B^4$ is —CH$_2$—C=N—CH$_2$—.
Preferably $B^1$-$B^2$-$B^3$-$B^4$ is —C($R^{5a}R^{5b}$)—C=N—O—.
Preferably $B^1$-$B^2$-$B^3$-$B^4$ is —CH(OH)—N—CH$_2$—CH$_2$—.
Preferably $B^1$-$B^2$-$B^3$-$B^4$ is —C(O)—N—CH$_2$—CH$_2$—.
Preferably $B^1$-$B^2$-$B^3$-$B^4$ is —CH$_2$—C=N—O—.

Preferably $R^1$ is hydrogen, $C_1$-$C_8$alkyl, $C_1$-$C_8$alkylcarbonyl- or $C_1$-$C_8$alkoxycarbonyl-; more preferably hydrogen, methyl, ethyl, methylcarbonyl-, or methoxycarbonyl-; most preferably hydrogen, methyl or ethyl; especially hydrogen or methyl; more especially hydrogen.

In a further embodiment, $R^1$ is $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxyc- arbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl, or $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group; preferably, $R^1$ is $C_1$-$C_8$alkyl, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, wherein each alkyl or alkoxy group may be optionally substituted with from one to three halogen atoms or with a cyano group, more preferably, $R^1$ is $C_1$-$C_8$cyanoalkyl, $C_1$-$C_8$alkoxy-$C_1$-$C_8$alkyl, $C_1$-$C_8$alkoxycarbonyl or $C_1$-$C_8$alkylcarbonyloxy$C_1$-$C_8$alkyl; most preferably, $R^1$ is methoxymethyl, ethoxymethyl, methoxycarbonyl, ethoxycarbonyl, methylcarbonyloxymethyl, 1-m ethylethylcarbonyloxymethyl or 1,1-dimethylethylcarbonyloxymethyl.

Preferably $R^2$ is $C_1$-$C_8$alkyl, $C_1$-$C_8$alkyl substituted by one to three $R^{6a}$, $C_2$-$C_8$alkenyl, $C_2$-$C_8$alkynyl, $C_3$-$C_8$cycloalkyl, $C_1$-$C_8$haloalkyl, di-$C_1$-$C_8$alkylamino, —N($R^8$)($R^9$), aryl, aryl substituted by one to three $R^{6b}$, 5-6 membered heteroaryl, 5-6 membered heteroaryl substituted by one to three $R^{6b}$ or halogen; more preferably $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_4$cycloalkyl, $C_1$-$C_4$haloalkyl, di-$C_1$-$C_4$alkylamino, —N($R^8$)($R^9$), 1-3 halo-substituted phenyl, 5-6 membered heteroaryl or fluoro; most preferably methyl, ethyl, cyclopropyl, chloromethyl, fluoromethyl, difluoromethyl, fluoro, dimethylamino or methylamino.

Preferably $R^3$ is $C_1$-$C_4$haloalkyl; more preferably chlorodifluoromethyl or trifluoromethyl; most preferably trifluoromethyl.

Preferably $R^4$ is aryl, aryl substituted by one to three $R^7$, 5-6 membered heteroaryl or 5-6 membered heteroaryl substituted by one to three $R^7$; more preferably $R^4$ is aryl or aryl substituted by one to three $R^7$; most preferably phenyl or phenyl substituted by one to three $R^7$; even more preferably $R^4$ is phenyl substituted by one to three $R^7$; especially $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl, or 3,4,5-trichloro-phenyl.

Preferably $R^5$ is independently halogen, cyano, $C_3$-$C_8$cycloalkyl, $C_1$-$C_8$haloalkyl, or $C_2$-$C_8$alkenyl, or two $R^5$ on adjacent carbon atoms together form a —CH=CH—CH=CH— bridge or a —CH$_2$—CH$_2$—CH$_2$— bridge; more preferably halogen, cyano, $C_2$-$C_8$ alkenyl, $C_3$-$C_8$cycloalkyl, or $C_1$-$C_8$haloalkyl; even more preferably bromo, chloro, fluoro, cyano, methyl, ethyl, trifluoromethyl, cyclopropyl, or vinyl; yet even more preferably bromo, chloro, fluoro, cyclopropyl, trifluoromethyl, vinyl, or methyl; most preferably chloro, bromo, trifluoromethyl, fluoro, or methyl.

Preferably $R^{5a}$ is halogen, hydroxyl, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkyl, $C_2$-$C_8$alkenyl, $C_2$-$C_8$alkynyl, $C_1$-$C_8$haloalkyl, $C_2$-$C_8$haloalkenyl, most preferably halogen, $C_1$-$C_8$alkylthio- or $C_1$-$C_8$alkyl.

Preferably $R^{5b}$ is halogen or hydrogen, most preferably hydrogen.

Preferably $R^{6a}$ independently is cyano, halogen, $C_1$-$C_4$alkoxy, or $C_1$-$C_4$haloalkoxy; more preferably fluoro, cyano, methoxy, difluoromethoxy or trifluoromethoxy.

Preferably $R^{6b}$ independently is halogen, cyano, $C_1$-$C_4$alkyl, or $C_1$-$C_4$haloalkyl, $C_1$-$C_4$alkoxy, or $C_1$-$C_4$haloalkoxy; more preferably bromo, chloro, fluoro, cyano, methyl, ethyl, trifluoromethyl, methoxy, difluoromethoxy, trifluoromethoxy; most preferably chloro, fluoro, cyano, methyl, ethyl, trifluoromethyl, methoxy, or trifluoromethoxy; especially chloro, fluoro, cyano, methyl, ethyl, trifluoromethyl, methoxy, or trifluoromethoxy; more especially bromo, fluoro, chloro, or trifluoromethyl.

Preferably $R^7$ is independently halogen, cyano, $C_1$-$C_4$alkyl, $C_1$-$C_4$haloalkyl, $C_1$-$C_4$alkoxy or $C_1$-$C_4$haloalkoxy; more preferably, methyl, fluoro, chloro, bromo, trifluoromethyl, trifluoromethoxy, cyano or methoxy, even more preferably $R^7$ is Cl, Br, F, CF$_3$, CH$_3$ or OCF$_3$.

Preferably $R^8$ and $R^9$ are independently hydrogen, cyano-$C_1$-$C_8$alkyl, $C_1$-$C_8$alkyl, $C_3$-$C_8$cycloalkyl, $C_1$-$C_8$haloalkyl, $C_1$-$C_8$alkoxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$; more preferably $R^8$ and $R^9$ are independently hydrogen, cyano-$C_1$-$C_8$alkyl-, $C_1$-$C_8$alkyl, $C_3$-$C_8$cycloalkyl, $C_1$-$C_8$alkoxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$; yet even more preferably $R^8$ and $R^9$ are independently hydrogen, $C_1$-$C_4$alkyl, $C_3$-$C_6$cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$— or phenyl-$CH_2$— wherein the phenyl moiety is substituted by one to three $R^7$, furanyl or furanyl substituted by one to three $R^7$, thietanyl, oxetanyl, oxo-thietanyl, or dioxo-thietanyl; yet even more preferably $R^8$ and $R^9$ are independently hydrogen, methyl, ethyl, propyl, isopropyl, cyclopropyl, cyclobutyl, oxetanyl, thietanyl, trifluoroethyl, difluoroethyl, allyl, propargyl, cyanomethyl, benzyl, benzyl substituted by one to three $R^7$, or pyridine-methyl- or pyridine-methyl- substituted by one to three $R^7$; especially $R^8$ and $R^9$ are independently hydrogen and methyl.

Preferably each $R^{19}$ is independently hydrogen, $C_1$-$C_8$alkyl, $C_1$-$C_8$haloalkyl or $C_3$-$C_8$cycloalkyl, more preferably hydrogen, $C_1$-$C_4$alkyl, $C_1$-$C_4$haloalkyl or $C_3$-$C_6$cycloalkyl, most preferably, hydrogen, methyl, ethyl or cyclopropyl.

Preferably n is 2.

In an embodiment E1 of formula (I), independent of other embodiments, $A^1$ is $CR^5$ and $A^2$, $A^3$ and $A^4$ are each CH, wherein $R^5$ is as defined in the first aspect of the invention.

In an embodiment E2 of formula (I), independent of other embodiments, $R^1$ is hydrogen, $C_1$-$C_8$alkyl, $C_1$-$C_8$alkylcarbonyl- or $C_1$-$C_8$alkoxycarbonyl-.

In an embodiment E2a of formula (I), independent of other embodiments, $R^1$ is $C_1$-$C_8$alkyl, $C_1$-$C_8$alkylcarbonyl-, $C_3$-$C_6$cycloalkylcarbonyl, $C_1$-$C_8$alkoxy, $C_1$-$C_8$alkoxy-$C_1$-$C_8$alkyl, $C_1$-$C_8$alkoxycarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl, wherein each alkyl or alkoxy group may be optionally substituted with from one to three halogen atoms or with a cyano group.

In an embodiment E3 of formula (I), independent of other embodiments, $R^2$ is $C_1$-$C_8$alkyl, $C_1$-$C_8$alkyl substituted by one to three $R^{6a}$, $C_2$-$C_8$alkenyl, $C_2$-$C_8$alkynyl, $C_3$-$C_8$cycloalkyl, $C_1$-$C_8$haloalkyl, di-$C_1$-$C_8$alkylamino, —N($R^8$)($R^9$), aryl, aryl substituted by one to three $R^{6b}$, 5-6 membered heteroaryl, 5-6 membered heteroaryl substituted by one to three $R^{6b}$, wherein $R^{6a}$ and $R^{6b}$ are as defined in the first aspect of the invention or halogen.

In an embodiment E4 of formula (I), independent of other embodiments, $R^3$ is $C_1$-$C_4$haloalkyl.

In an embodiment E5 of formula (I), independent of other embodiments, $R^4$ is aryl, aryl substituted by one to three $R^7$, 5-6 membered heteroaryl or 5-6 membered heteroaryl substituted by one to three $R^7$, wherein $R^7$ is as defined in the first aspect of the invention.

Embodiment E6 of formula (I) provides compounds of formula (I) wherein $A^1$ is $CR^5$ and $A^2$, $A^3$ and $A^4$ are each CH; $R^1$ is hydrogen, methyl, ethyl, methylcarbonyl-, or methoxycarbonyl; $R^2$ is $C_1$-$C_8$alkyl, $C_1$-$C_8$alkyl substituted by one to three $R^{6a}$, $C_2$-$C_8$alkenyl, $C_2$-$C_8$alkynyl, $C_3$-$C_8$cycloalkyl, $C_1$-$C_8$haloalkyl, di-$C_1$-$C_8$alkylamino, aryl, aryl substituted by one to three $R^{6b}$, 5-6 membered heteroaryl, 5-6 membered heteroaryl substituted by one to three $R^{6b}$ or fluoro; $R^3$ is $C_1$-$C_4$haloalkyl; $R^4$ is aryl or aryl substituted by one to three $R^7$; and n is 2; wherein $R^5$ is halogen or $C_1$-$C_8$alkyl, $C_3$-$C_8$cycloalkyl, $C_1$-$C_8$haloalkyl, or $C_2$-$C_8$alkenyl; $R^{6a}$ is independently cyano, halogen, $C_1$-$C_4$alkoxy, or $C_1$-$C_4$haloalkoxy; and $R^{6b}$ is independently halogen, cyano, $C_1$-$C_4$alkyl, or $C_1$-$C_4$haloalkyl, $C_1$-$C_4$alkoxy, or $C_1$-$C_4$haloalkoxy.

Embodiment E7 of formula (I) provides compounds of formula (I) wherein $A^1$ is $CR^5$ and $A^2$, $A^3$ and $A^4$ are each CH; $R^1$ is hydrogen, methyl, ethyl, methylcarbonyl-, or methoxycarbonyl; $R^2$ is $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_6$cycloalkyl, $C_1$-$C_4$haloalkyl, di-$C_1$-$C_4$alkylamino, —NH($C_1$-$C_4$alkyl), fluoro, phenyl, or 5-6 membered heteroaryl; $R^3$ is $C_1$-$C_4$haloalkyl; $R^4$ is aryl or aryl substituted by one to three $R^7$; and n is 2; wherein $R^5$ is halogen, cyano, $C_1$-$C_8$alkyl, $C_3$-$C_8$cycloalkyl, $C_1$-$C_8$haloalkyl, $C_2$-$C_8$alkenyl; $R^{6a}$ is independently fluoro, cyano, methoxy, difluoromethoxy or trifluoromethoxy; and $R^7$ is independently bromo, chloro, fluoro, cyano, methyl, ethyl, trifluoromethyl, methoxy, difluoromethoxy, trifluoromethoxy.

Embodiment E8 of formula (I) provides compounds of formula (I) wherein $A^1$ is $CR^5$ and $A^2$, $A^3$ and $A^4$ are each CH; $R^1$ is hydrogen; $R^2$ is $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_6$cycloalkyl, $C_1$-$C_4$haloalkyl, di-$C_1$-$C_4$alkylamino, —NH($C_1$-$C_4$alkyl), fluoro, 1-3 halo-substituted phenyl, or 5-6 membered heteroaryl; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E9 of formula (I) provides compounds of formula (I) wherein $A^1$ is $CR^5$ and $A^2$, $A^3$ and $A^4$ are each CH; $R^1$ is hydrogen; $R^2$ is $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_5$cycloalkyl, $C_1$-$C_4$haloalkyl, di-$C_1$-$C_4$alkylamino, —NH($C_1$-$C_4$alkyl), fluoro or 5-6 membered heteroaryl; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E10 of formula (I) provides compounds of formula (I) wherein $A^1$ is $CR^5$ and $A^2$, $A^3$ and $A^4$ are each CH; $R^1$ is hydrogen; $R^2$ is methyl, ethyl, propyl, isopropyl, cyclopropyl, cyclobutyl, oxetanyl, thietanyl, chloromethyl, fluoromethyl, difluoromethyl, trifluoroethyl, difluoroethyl, allyl, propargyl, cyanomethyl, dimethylamino, methylamino or fluoro; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E11 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is chloro, bromo, trifluoromethyl, fluoro, or methyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl; or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E12 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is chloro or methyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E13 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is chloro, bromo, trifluoromethyl, fluoro, or methyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E14 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is chloro or methyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E15 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is chloro; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E16 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E17 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E18 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E19 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is bromo; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl, or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E20 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E21 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E22 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E23 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is methyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl, or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E24 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E25 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E26 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E27 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is trifluoromethyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl, or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E28 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E29 of formula (I) provides compounds of formula (I) wherein $A^2$, $A^3$ and $A^4$ are each CH; $R^1$ is hydrogen; $R^3$ is chlorodifluoromethyl or trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E30 of formula (I) provides compounds of formula (I) wherein $A^2$, $A^3$ and $A^4$ are each CH; $R^1$ is hydrogen; $R^3$ is trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluoro-phenyl, 3,4,5-trichloro-phenyl, 3-bromo-5-trifluoromethyl-phenyl, 3-chloro-5-trifluoromethyl-phenyl.

Embodiment E31 of formula (I) provides compounds of formula (I) wherein $A^1$ is $CR^5$ and $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^2$ is $C_1$-$C_8$alkyl, $C_1$-$C_8$alkyl substituted by one to three $R^{6a}$, $C_2$-$C_8$alkenyl, $C_2$-$C_8$alkynyl, $C_3$-$C_8$cycloalkyl, $C_1$-$C_8$haloalkyl, di-$C_1$-$C_8$alkylamino, aryl, aryl substituted by one to three $R^{6b}$, 5-6 membered heteroaryl, 5-6 membered heteroaryl substituted by one to three $R^{6b}$ or fluoro; $R^3$ is $C_1$-$C_4$haloalkyl; $R^4$ is aryl or aryl substituted by one to three $R^7$; and n is 2; wherein $R^5$ is halogen or $C_1$-$C_8$alkyl, $C_3$-$C_8$cycloalkyl, $C_1$-$C_8$haloalkyl, or $C_2$-$C_8$alkenyl; $R^{6a}$ is independently cyano, halogen, $C_1$-$C_4$alkoxy, or $C_1$-$C_4$haloalkoxy; and $R^{6b}$ is independently halogen, cyano, $C_1$-$C_4$alkyl, or $C_1$-$C_4$haloalkyl, $C_1$-$C_4$alkoxy, or $C_1$-$C_4$haloalkoxy.

Embodiment E32 of formula (I) provides compounds of formula (I) wherein $A^1$ is $CR^5$ and $A^2$, $A^3$ and $A^4$ are each CH; $R^1$ is methoxymethyl, ethoxymethyl, methoxycarbonyl, ethoxycarbonyl, methylcarbonyloxymethyl, 1-m ethylethylcarbonyloxymethyl or 1,1-dimethylethylcarbonyloxymethyl; $R^2$ is $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_5$cycloalkyl, $C_1$-$C_4$haloalkyl, di-$C_1$-$C_4$alkylamino, —NH($C_1$-$C_4$alkyl), fluoro, phenyl, or 5-6 membered heteroaryl; $R^3$ is $C_1$-$C_4$haloalkyl; $R^4$ is aryl or aryl substituted by one to three $R^7$; and n is 2; wherein $R^5$ is halogen, cyano, $C_1$-$C_8$alkyl, $C_3$-$C_8$cycloalkyl, $C_1$-$C_8$haloalkyl, $C_2$-$C_8$alkenyl; $R^{6a}$ is independently fluoro, cyano, methoxy, difluoromethoxy or trifluoromethoxy; and $R^7$ is independently bromo, chloro, fluoro, cyano, methyl, ethyl, trifluoromethyl, methoxy, difluoromethoxy, trifluoromethoxy.

Embodiment E33 of formula (I) provides compounds of formula (I) wherein $A^1$ is $CR^5$ and $A^2$, $A^3$ and $A^4$ are each CH; $R^1$ is methoxymethyl, ethoxymethyl, methoxycarbonyl, ethoxycarbonyl, methylcarbonyloxymethyl, 1-m ethylethylcarbonyloxymethyl or 1,1-dimethylethylcarbonyloxymethyl; $R^2$ is $C_1$-$C_4$alkyl, $C_1$-$C_4$alkyl substituted by one to three $R^{6a}$, $C_2$-$C_4$alkenyl, $C_2$-$C_4$alkynyl, $C_3$-$C_5$cycloalkyl, $C_1$-$C_4$haloalkyl, di-$C_1$-$C_4$alkylamino, —NH($C_1$-$C_4$alkyl), fluoro, 1-3 halo-substituted phenyl, or 5-6 membered heteroaryl; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E34 of formula (I) provides compounds of formula (I) wherein $A^1$ is $CR^5$ and $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^2$ is $C_1$-$C_4$alkyl substituted by one to three $R^{6a}$, $C_2$-$C_4$alkenyl, $C_2$-$C_4$alkynyl, $C_3$-$C_5$cycloalkyl, $C_1$-$C_4$haloalkyl, —NH($C_1$-$C_4$alkyl), fluoro or 5-6 membered heteroaryl; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E35 of formula (I) provides compounds of formula (I) wherein $A^1$ is $CR^5$ and $A^2$, $A^3$ and $A^4$ are each CH; $R^1$ is methoxymethyl, ethoxymethyl, methoxycarbonyl, ethoxycarbonyl, methylcarbonyloxymethyl, 1-m ethylethylcarbonyloxymethyl or 1,1-dimethylethylcarbonyloxymethyl; $R^2$ is methyl, ethyl, propyl, isopropyl, cyclopropyl, cyclobutyl, oxetanyl, thietanyl, chloromethyl, fluoromethyl, difluoromethyl, trifluoroethyl, difluoroethyl, allyl, propargyl, cyanomethyl, dimethylamino, methylamino or fluoro; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

Embodiment E36 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is chloro, bromo, trifluoromethyl, fluoro, or methyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl, or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E37 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is chloro or methyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E38 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is chloro, bromo, trifluoromethyl, fluoro, or methyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E39 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is chloro or methyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E40 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is chloro; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl; or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E41 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E42 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E43 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is chloro; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E44 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is bromo; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl; or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E45 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E46 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E47 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is bromo; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E48 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is methyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl; or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E49 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichlorophenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E50 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E51 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is methyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

Embodiment E52 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is trifluoromethyl; $R^2$ is methyl, ethyl, cyclopropyl, chloromethyl, fluoromethyl, difluoromethyl, iso-propyl, methylamino, dimethlyamino, fluoro, cyclobutyl, 3,3,3,-trifluoropropyl; or 2,2,2-trifluoroethyl, or methoxyethyl; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E53 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; especially $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl, pyridyl, or 3-5-substituted pyridyl wherein the substituents are selected from bromo, chloro, fluoro or trifluoro; more preferably $R^4$ is 3,5-dibromo-phenyl, 3,5-dichloro-phenyl, 3,5-bis-(trifluoromethyl)-phenyl, 4-bromo-3,5-dichlorophenyl, 3,4,5-trichloro-phenyl, 3,5-dichloro-4-fluorophenyl.

Embodiment E54 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is chlorodifluoromethyl or trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is phenyl, pyridyl, mono-, di- or tri-substituted phenyl where the substituents are independently selected from chloro, bromo, fluoro, or trifluoromethyl, or mono- or di-substituted pyridyl where the substituents are independently selected from chloro, bromo, fluoro, or trifluoromethyl.

Embodiment E55 of formula (I) provides compounds of formula (I) wherein $A^2$, $A^3$ and $A^4$ are each CH; $R^1$ is methoxymethyl, ethoxymethyl, methoxycarbonyl, ethoxycarbonyl, methylcarbonyloxymethyl, 1-methylethylcarbonyloxymethyl or 1,1-dimethylethylcarbonyloxymethyl; $R^3$ is trifluoromethyl; n is 2; $A^1$ is $CR^5$, wherein $R^5$ is trifluoromethyl; $R^2$ is methyl, ethyl, cyclopropyl, methylamino, dimethlyamino, chloromethyl, fluoromethyl, difluoromethyl or fluoro; and $R^4$ is 3,5-dichloro-4-fluorophenyl, 3,4,5-trichloro-phenyl, 3-bromo-5-trifluoromethyl-phenyl, 3-chloro-5-trifluoromethyl-phenyl.

In one embodiment the invention provides compounds of formula (IA)

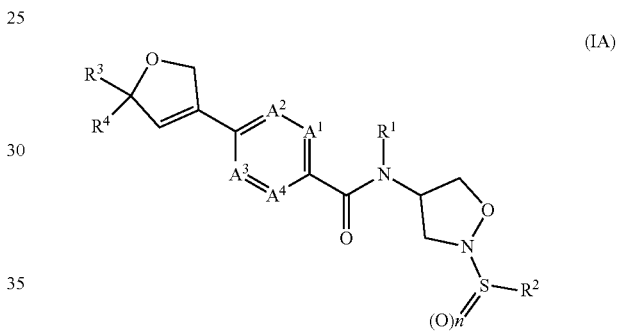

(IA)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IB)

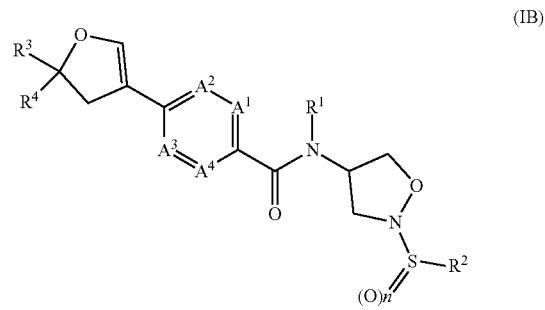

(IB)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IC)

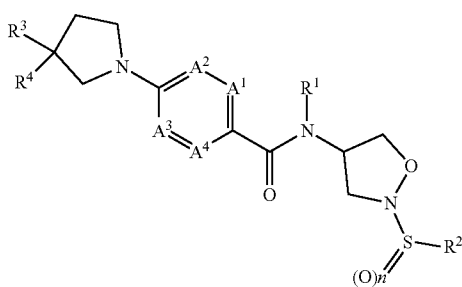

(IC)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (ID)

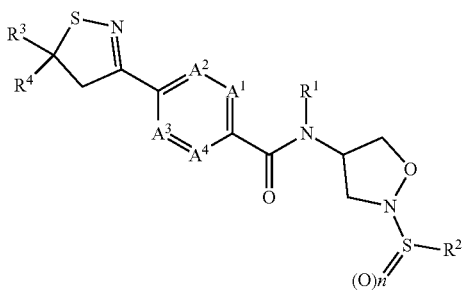

(ID)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IE)

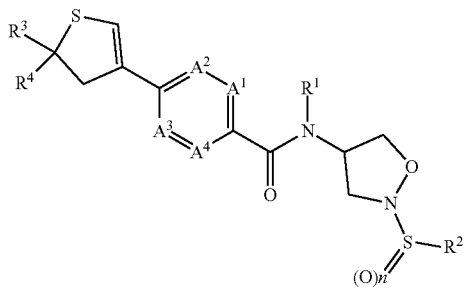

(IE)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IF)

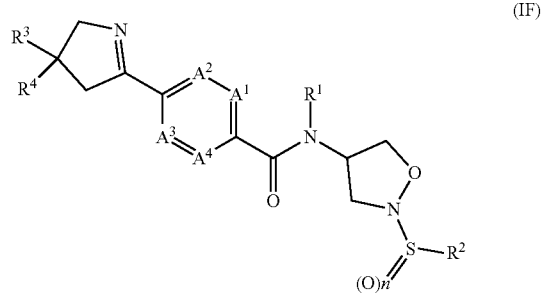

(IF)

wherein $A^1$, $A^2$, $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IG)

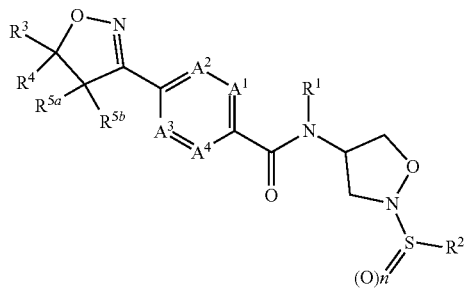

(IG)

wherein $A^1$, $A^2$, $A^3$, $A^4$, $R^1$, $R^2$, $R^3$, $R^4$, $R^{5a}$, $R^{5b}$ and n and their preferred values are as defined for a compound of formula (I); or a salt or N-oxide thereof. Further preferred in this embodiment are the embodiments E1 to E55. Preferably $R^{5a}$ is halogen, hydroxyl, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkyl, $C_2$-$C_8$alkenyl, $C_2$-$C_8$alkynyl, $C_1$-$C_8$haloalkyl, $C_2$-$C_8$haloalkenyl, most preferably halogen, $C_1$-$C_8$alkylthio- or $C_1$-$C_8$alkyl. Preferably $R^{5b}$ is halogen or hydrogen, most preferably hydrogen.

In a further embodiment the invention provides compounds of formula (IH)

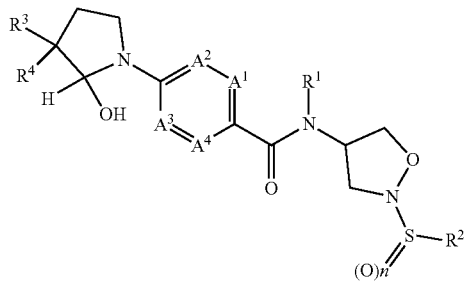

(IH)

wherein $A^1$, $A^2$, $A^3$, $A^4$, $R^1$, $R^2$, $R^3$, $R^4$, and n and their preferred values are as defined for a compound of formula (I); or a salt or N-oxide thereof. Further preferred in this embodiment are the embodiments E1 to E55.

In a further embodiment the invention provides compounds of formula (IJ)

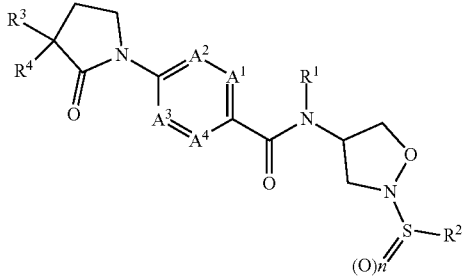

(IJ)

wherein $A^1$, $A^2$, $A^3$, $A^4$, $R^1$, $R^2$, $R^3$, $R^4$, and n and their preferred values are as defined for a compound of formula (I); or a salt or N-oxide thereof. Further preferred in this embodiment are the embodiments E1 to E55.

In a further embodiment the invention provides compounds of formula (IK)

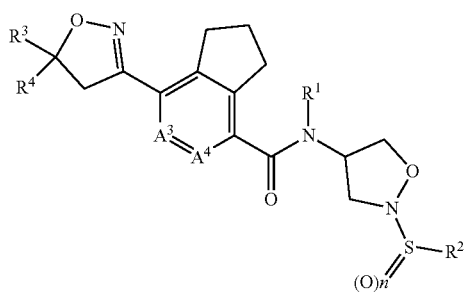

(IK)

wherein $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IL)

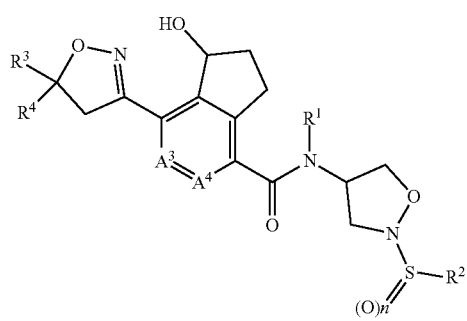

(IL)

wherein $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

In a further embodiment the invention provides compounds of formula (IM)

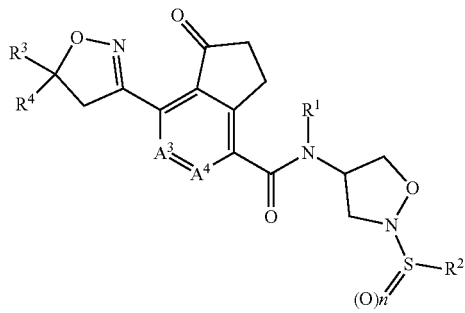

(IM)

wherein $A^3$, $A^4$, $R^1$, $R^2$, $R^3$, $R^4$ and n and their preferred values are as defined for a compound of formula (I); or a salt or N-oxide thereof. Further preferred in this embodiment are the embodiments E1 to E55.

The present invention also provides intermediates useful for the preparation of compounds of formula (I). Certain intermediates are novel and as such form a further aspect of the invention. One group of novel intermediates are compounds of formula (Int-I)

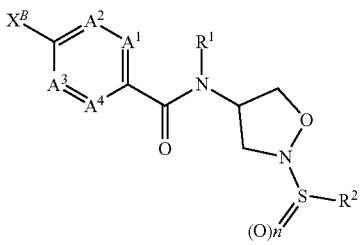

(Int-I)

wherein $A^1$, $A^2$, $A^3$, $A^4$, $R^1$, $R^2$ and n are as defined for a compound of formula (I) and $X^B$ is a halogen, such as bromo, or $X^B$ is cyano, formyl, CH=N—OH or acetyl; or a salt or N-oxide thereof. The preferences for $A^1$, $A^2$, $A^3$, $A^4$, $R^1$, $R^2$ and n are the same as the preferences set out for the corresponding substituents of a compound of formula (I).

Another group of novel intermediates are compounds of formula (Int-II)

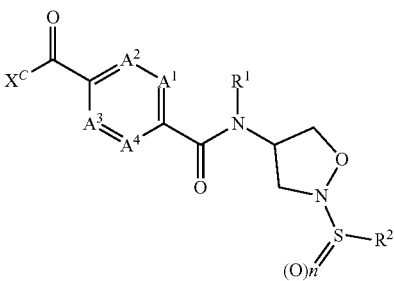

(Int-II)

wherein $A^1$, $A^2$, $A^3$, $A^4$, $R^1$, $R^2$ and n are as defined for a compound of formula (I); $X^C$ is $CH_2$-halogen, wherein halogen is preferably bromo or chloro, CH=C($R^3$)$R^4$ or $CH_2C(OH)(R^3)R^4$ wherein $R^3$ and $R^4$ are as defined for a compound of formula (I); or a salt or N-oxide thereof. The preferences for $A^1$, $A^2$, $A^3$, $A^4$, $R^1$, $R^2$ and n are the same as the preferences set out for the corresponding substituents of a compound of formula (I).

Another group of novel intermediates are compounds of formula (Int-III)

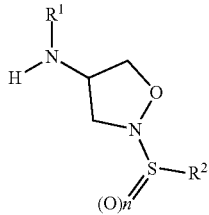

wherein $R^1$, $R^2$ and n are as defined for a compound of formula (I); or a salt or N-oxide thereof. The preferences for $R^1$, $R^2$ and n are the same as the preferences set out for the corresponding substituents of a compound of formula (I).

Another group of novel intermediates are compounds of formula (Int-IV)

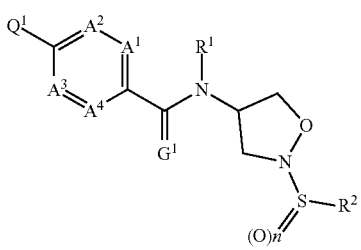

wherein $Q^1$ is $CO_2H$ or $NH_2$, and wherein $A^1$, $A^2$, $A^3$, $A^4$, $G^1$, $R^1$, n and $R^2$ are as defined for a compound of formula (I); or a salt or N-oxide thereof. The preferences for $A^1$, $A^2$, $A^3$, $A^4$, $G^1$, $R^1$, n and $R^2$ are the same as the preferences set out for the corresponding substituents of a compound of formula (I). For example, the preferences for $A^1$, $A^2$, $A^3$, $A^4$, $G^1$, $R^1$, and $R^2$ may be the same as for formula (IA), (IB), (IC), (ID), (IE), (IF), (IG), (IH), (IJ), (IK), (IL), (IM).

Another group of novel intermediates are compounds of formula (Int-V)

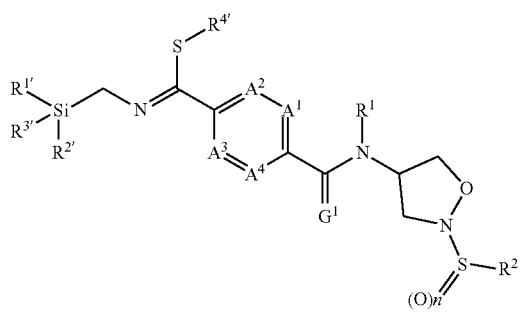

wherein $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for a compound of formula (I); or a salt or N-oxide thereof. The preferences for $A^1$, $A^2$, $A^3$, $A^4$, $G^1$, $R^1$, n and $R^2$ are the same as the preferences set out for the corresponding substituents of a compound of formula (I). For example, the preferences for $A^1$, $A^2$, $A^3$, $A^4$, $G^1$, $R^1$, n and $R^2$ may be the same as for formula (IA), (IB), (IC), (ID), (IE), (IF), (IG), (IH), (IJ), (IK), (IL), (IM). Preferably $R^{1'}$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-VI)

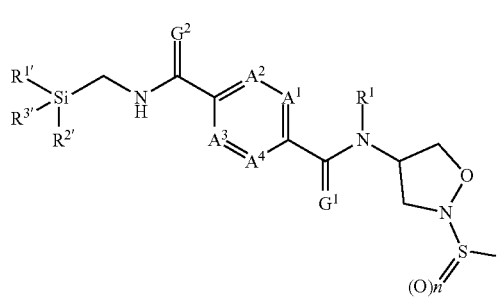

wherein $G^2$ is O or S, $R^{1'}$, $R^{2'}$ and $R^{3'}$ are independently of each other optionally substituted alkyl or optionally substituted phenyl, and $A^1$, $A^2$, $A^3$, $A^4$, $G^1$, $R^1$, n and $R^2$ are as defined for a compound of formula (I); or a salt or N-oxide thereof. The preferences for $A^1$, $A^2$, $A^3$, $A^4$, $G^1$, $R^1$, n and $R^2$ are the same as the preferences set out for the corresponding substituents of a compound of formula (I). For example, the preferences for $A^1$, $A^2$, $A^3$, $A^4$, $G^1$, $R^1$, n and $R^2$ may be the same as for formula (IA), (IB), (IC), (ID), (IE), (IF), (IG), (IH), (IJ), (IK), (IL), (IM). Preferably $R^{1'}$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-VII)

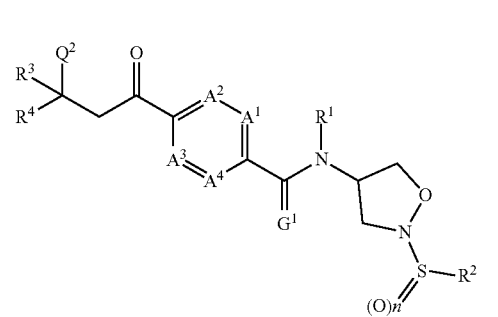

wherein $Q^2$ is $CH_2$—$NO_2$, CN or group Qa

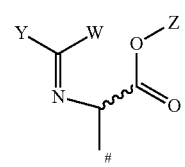

W is hydrogen or optionally substituted aryl, Y is optionally substituted aryl, and Z is optionally substituted alkyl or optionally substituted arylalkylene, and $A^1$, $A^2$, $A^3$, $A^4$, $G^1$, $R^1$, $R^2$, $R^3$, and n are as defined for a compound of formula (I); or a salt or N-oxide thereof. The preferences for $A^1$, $A^2$, $A^3$, $A^4$, $G^1$, $R^1$, $R^2$, $R^3$, $R^4$ and n are the same as the preferences set out for the corresponding substituents of a compound of formula (I). For example, the preferences for $A^1$, $A^2$, $A^3$, $A^4$, $G^1$, $R^1$, $R^2$, $R^3$, $R^4$ and n may be the same as for formula (IA), (IB), (IC), (ID), (IE), (IF), (IG), (IH), (IJ), (IK), (IL), (IM). Preferably W is hydrogen or phenyl. Preferably Y is phenyl. Preferably Z is $C_1$-$C_8$alkyl, or phenyl-$C_1$-$C_8$alkyl.

Another group of novel intermediates are compounds of formula (Int-VIII)

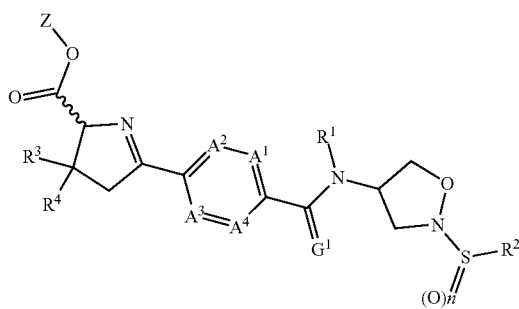

(Int-VIII)

wherein Z is optionally substituted alkyl or optionally substituted arylalkylene, and $A^1$, $A^2$, $A^3$, $A^4$, $G^1$, $R^1$, $R^2$, $R^3$, $R^4$ and n are as defined for a compound of formula (I); or a salt or N-oxide thereof. The preferences for $A^1$, $A^2$, $A^3$, $A^4$, $G^1$, $R^1$, $R^2$, $R^3$, $R^4$ and n are the same as the preferences set out for the corresponding substituents of a compound of formula (I). For example, the preferences for $A^1$, $A^2$, $A^3$, $A^4$, $G^1$, $R^1$, $R^2$, $R^3$, $R^4$ and n may be the same as for formula (IA), (IB), (IC), (ID), (IE), (IF), (IG), (IH), (IJ), (IK), (IL), (IM). Preferably Z is $C_1$-$C_8$alkyl, or phenyl-$C_1$-$C_8$alkyl.

Another group of novel intermediates are compounds of formula (Int-IX)

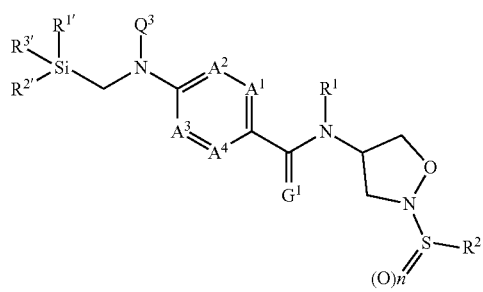

(Int-IX)

wherein $Q^3$ is $CH_2$—$OR^{4'}$ or $CH_2$—CN, $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for a compound of formula (I); or a salt or N-oxide thereof. The preferences for $A^1$, $A^2$, $A^3$, $A^4$, $G^1$, $R^1$, n and $R^2$ are the same as the preferences set out for the corresponding substituents of a compound of formula (I). For example, the preferences for $A^1$, $A^2$, $A^3$, $A^4$, $G^1$, $R^1$, n and $R^2$ may be the same as for formula (IA), (IB), (IC), (ID), (IE), (IF), (IG), (IH), (IJ), (IK), (IL), (IM). Preferably $R^{1'}$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-X)

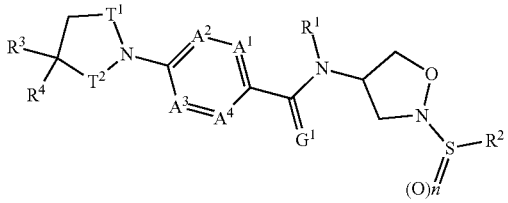

(Int-X)

wherein $T^1$ and $T^2$ are independently $CH_2$ or C=O or CHOH, providing that at least one of $T^1$ and $T^2$ is C=O or CHOH, and $A^1$, $A^2$, $A^3$, $A^4$, $G^1$, $R^1$, $R^2$, $R^3$, $R^4$ and n are as defined for a compound of formula (I); or a salt or N-oxide thereof. The preferences for $A^1$, $A^2$, $A^3$, $A^4$, $G^1$, $R^1$, $R^2$, $R^3$, $R^4$ and n are the same as the preferences set out for the corresponding substituents of a compound of formula (I). For example, the preferences for $A^1$, $A^2$, $A^3$, $A^4$, $G^1$, $R^1$, $R^2$, $R^3$, $R^4$ and n may be the same as for formula (IA), (IB), (IC), (ID), (IE), (IF), (IG), (IH), (IJ), (IK), (IL), (IM).

Compounds of formula (I) include at least one chiral centre and may exist as compounds of formula (I*) or compounds of formula (I**):

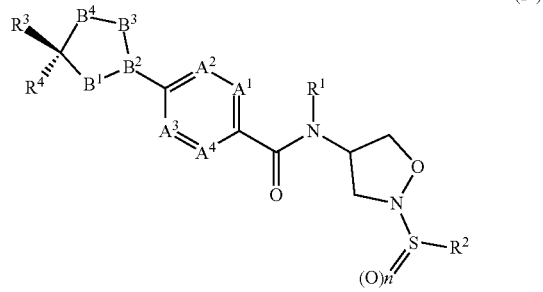

(I*)

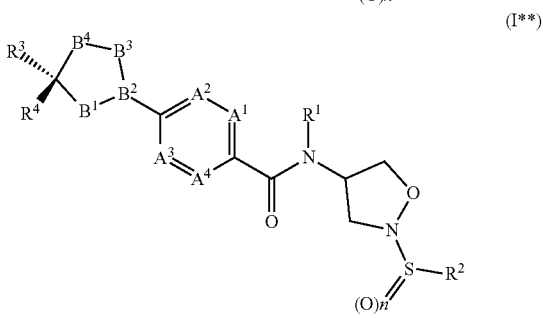

(I**)

Generally compounds of formula (I**) are more biologically active than compounds of formula (I*). The invention includes mixtures of compounds (I*) and (I) in any ratio e.g. in a molar ratio of 1:99 to 99:1, e.g. 10:1 to 1:10, e.g. a substantially 50:50 molar ratio. In an enantiomerically (or epimerically) enriched mixture of formula (I), the molar proportion of compound (I**) compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula (I*), the molar proportion of the compound of formula (I*) compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula (I**) are preferred.

Tables 1 to 128: Compounds of Formula (Ia)

The invention is further illustrated by making available the following individual compounds of formula (Ia) listed below in Tables 1 to 128.

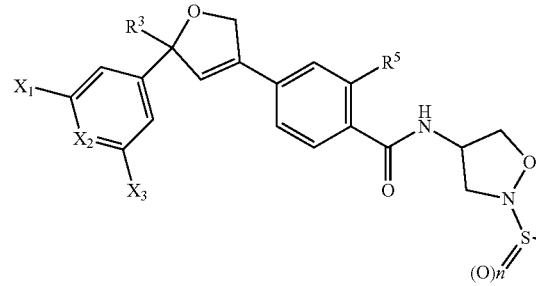

(Ia)

Each of Tables 1 to 128, which follow the Table P below, make available 1500 compounds of the formula (Ia) in which $X_2$, $X_3$, $R^3$, $X_1$ and $R^5$ are the substituents defined in Table P and $R^1$ and $R^2$ are the substituents defined in the relevant Table 1 to 128. Thus Table 1 individualises 1500 compounds of formula (Ia) wherein for each row of Table P, the $R^1$ and $R^2$ substituents are as defined in Table 1; similarly, Table 2 individualises 1500 compounds of formula (Ia) wherein for each row of Table P, the $R^1$ and $R^2$ substituents are as defined in Table 2; and so on for Tables 3 to 128.

Each compound disclosed in Tables 1 to 128 represents a disclosure of a compound according to the compound of formula (I*) in which $B^1$-$B^2$-$B^3$-$B^4$ is —CH=C—CH$_2$—O—, and a disclosure according to the compound of formula (I**) in which $B^1$-$B^2$-$B^3$-$B^4$ is —CH=C—CH$_2$—O— as well as mixtures thereof.

TABLE P

|    | $X_3$ | $R^3$ | $X_1$ | $R^5$ | $X_2$ |
|----|-------|-------|-------|-------|-------|
| 1  | H     | CF$_3$ | H    | Me    | N     |
| 2  | Cl    | CF$_3$ | H    | Me    | N     |
| 3  | Br    | CF$_3$ | H    | Me    | N     |
| 4  | F     | CF$_3$ | H    | Me    | N     |
| 5  | CF$_3$ | CF$_3$ | H   | Me    | N     |
| 6  | H     | CF$_2$Cl | H  | Me    | N     |
| 7  | Cl    | CF$_2$Cl | H  | Me    | N     |
| 8  | Br    | CF$_2$Cl | H  | Me    | N     |
| 9  | F     | CF$_2$Cl | H  | Me    | N     |
| 10 | CF$_3$ | CF$_2$Cl | H | Me    | N     |
| 11 | H     | CF$_3$ | Cl   | Me    | N     |
| 12 | Cl    | CF$_3$ | Cl   | Me    | N     |
| 13 | Br    | CF$_3$ | Cl   | Me    | N     |
| 14 | F     | CF$_3$ | Cl   | Me    | N     |
| 15 | CF$_3$ | CF$_3$ | Cl  | Me    | N     |
| 16 | H     | CF$_2$Cl | Cl | Me    | N     |
| 17 | Cl    | CF$_2$Cl | Cl | Me    | N     |
| 18 | Br    | CF$_2$Cl | Cl | Me    | N     |
| 19 | F     | CF$_2$Cl | Cl | Me    | N     |
| 20 | CF$_3$ | CF$_2$Cl | Cl| Me    | N     |
| 21 | H     | CF$_3$ | Br   | Me    | N     |
| 22 | Cl    | CF$_3$ | Br   | Me    | N     |
| 23 | Br    | CF$_3$ | Br   | Me    | N     |

TABLE P-continued

|    | $X_3$ | $R^3$ | $X_1$ | $R^5$ | $X_2$ |
|----|-------|-------|-------|-------|-------|
| 24 | F     | CF$_3$ | Br   | Me    | N     |
| 25 | CF$_3$ | CF$_3$ | Br  | Me    | N     |
| 26 | H     | CF$_2$Cl | Br | Me    | N     |
| 27 | Cl    | CF$_2$Cl | Br | Me    | N     |
| 28 | Br    | CF$_2$Cl | Br | Me    | N     |
| 29 | F     | CF$_2$Cl | Br | Me    | N     |
| 30 | CF$_3$ | CF$_2$Cl | Br| Me    | N     |
| 31 | H     | CF$_3$ | F    | Me    | N     |
| 32 | Cl    | CF$_3$ | F    | Me    | N     |
| 33 | Br    | CF$_3$ | F    | Me    | N     |
| 34 | F     | CF$_3$ | F    | Me    | N     |
| 35 | CF$_3$ | CF$_3$ | F   | Me    | N     |
| 36 | H     | CF$_2$Cl | F  | Me    | N     |
| 37 | Cl    | CF$_2$Cl | F  | Me    | N     |
| 38 | Br    | CF$_2$Cl | F  | Me    | N     |
| 39 | F     | CF$_2$Cl | F  | Me    | N     |
| 40 | CF$_3$ | CF$_2$Cl | F | Me    | N     |
| 41 | H     | CF$_3$ | CF$_3$ | Me | N     |
| 42 | Cl    | CF$_3$ | CF$_3$ | Me | N     |
| 43 | Br    | CF$_3$ | CF$_3$ | Me | N     |
| 44 | F     | CF$_3$ | CF$_3$ | Me | N     |
| 45 | CF$_3$ | CF$_3$ | CF$_3$ | Me| N     |
| 46 | H     | CF$_2$Cl | CF$_3$ | Me | N   |
| 47 | Cl    | CF$_2$Cl | CF$_3$ | Me | N   |
| 48 | Br    | CF$_2$Cl | CF$_3$ | Me | N   |
| 49 | F     | CF$_2$Cl | CF$_3$ | Me | N   |
| 50 | CF$_3$ | CF$_2$Cl | CF$_3$| Me | N   |
| 51 | H     | CF$_3$ | H    | Cl    | N     |
| 52 | Cl    | CF$_3$ | H    | Cl    | N     |
| 53 | Br    | CF$_3$ | H    | Cl    | N     |
| 54 | F     | CF$_3$ | H    | Cl    | N     |
| 55 | CF$_3$ | CF$_3$ | H   | Cl    | N     |
| 56 | H     | CF$_2$Cl | H  | Cl    | N     |
| 57 | Cl    | CF$_2$Cl | H  | Cl    | N     |
| 58 | Br    | CF$_2$Cl | H  | Cl    | N     |
| 59 | F     | CF$_2$Cl | H  | Cl    | N     |
| 60 | CF$_3$ | CF$_2$Cl | H | Cl    | N     |
| 61 | H     | CF$_3$ | Cl   | Cl    | N     |
| 62 | Cl    | CF$_3$ | Cl   | Cl    | N     |
| 63 | Br    | CF$_3$ | Cl   | Cl    | N     |
| 64 | F     | CF$_3$ | Cl   | Cl    | N     |
| 65 | CF$_3$ | CF$_3$ | Cl  | Cl    | N     |
| 66 | H     | CF$_2$Cl | Cl | Cl    | N     |
| 67 | Cl    | CF$_2$Cl | Cl | Cl    | N     |
| 68 | Br    | CF$_2$Cl | Cl | Cl    | N     |
| 69 | F     | CF$_2$Cl | Cl | Cl    | N     |
| 70 | CF$_3$ | CF$_2$Cl | Cl| Cl    | N     |
| 71 | H     | CF$_3$ | Br   | Cl    | N     |
| 72 | Cl    | CF$_3$ | Br   | Cl    | N     |
| 73 | Br    | CF$_3$ | Br   | Cl    | N     |
| 74 | F     | CF$_3$ | Br   | Cl    | N     |
| 75 | CF$_3$ | CF$_3$ | Br  | Cl    | N     |
| 76 | H     | CF$_2$Cl | Br | Cl    | N     |
| 77 | Cl    | CF$_2$Cl | Br | Cl    | N     |
| 78 | Br    | CF$_2$Cl | Br | Cl    | N     |
| 79 | F     | CF$_2$Cl | Br | Cl    | N     |
| 80 | CF$_3$ | CF$_2$Cl | Br| Cl    | N     |
| 81 | H     | CF$_3$ | F    | Cl    | N     |
| 82 | Cl    | CF$_3$ | F    | Cl    | N     |
| 83 | Br    | CF$_3$ | F    | Cl    | N     |
| 84 | F     | CF$_3$ | F    | Cl    | N     |
| 85 | CF$_3$ | CF$_3$ | F   | Cl    | N     |
| 86 | H     | CF$_2$Cl | F  | Cl    | N     |
| 87 | Cl    | CF$_2$Cl | F  | Cl    | N     |
| 88 | Br    | CF$_2$Cl | F  | Cl    | N     |
| 89 | F     | CF$_2$Cl | F  | Cl    | N     |
| 90 | CF$_3$ | CF$_2$Cl | F | Cl    | N     |
| 91 | H     | CF$_3$ | CF$_3$ | Cl | N    |
| 92 | Cl    | CF$_3$ | CF$_3$ | Cl | N    |
| 93 | Br    | CF$_3$ | CF$_3$ | Cl | N    |
| 94 | F     | CF$_3$ | CF$_3$ | Cl | N    |
| 95 | CF$_3$ | CF$_3$ | CF$_3$ | Cl| N    |
| 96 | H     | CF$_2$Cl | CF$_3$ | Cl | N  |
| 97 | Cl    | CF$_2$Cl | CF$_3$ | Cl | N  |
| 98 | Br    | CF$_2$Cl | CF$_3$ | Cl | N  |
| 99 | F     | CF$_2$Cl | CF$_3$ | Cl | N  |
| 100| CF$_3$ | CF$_2$Cl | CF$_3$| Cl | N  |
| 101| H     | CF$_3$ | H    | Br    | N     |

TABLE P-continued

|     | $X_3$ | $R^3$ | $X_1$ | $R^5$ | $X_2$ |
|-----|-------|-------|-------|-------|-------|
| 102 | Cl | $CF_3$ | H | Br | N |
| 103 | Br | $CF_3$ | H | Br | N |
| 104 | F | $CF_3$ | H | Br | N |
| 105 | $CF_3$ | $CF_3$ | H | Br | N |
| 106 | H | $CF_2Cl$ | H | Br | N |
| 107 | Cl | $CF_2Cl$ | H | Br | N |
| 108 | Br | $CF_2Cl$ | H | Br | N |
| 109 | F | $CF_2Cl$ | H | Br | N |
| 110 | $CF_3$ | $CF_2Cl$ | H | Br | N |
| 111 | H | $CF_3$ | Cl | Br | N |
| 112 | Cl | $CF_3$ | Cl | Br | N |
| 113 | Br | $CF_3$ | Cl | Br | N |
| 114 | F | $CF_3$ | Cl | Br | N |
| 115 | $CF_3$ | $CF_3$ | Cl | Br | N |
| 116 | H | $CF_2Cl$ | Cl | Br | N |
| 117 | Cl | $CF_2Cl$ | Cl | Br | N |
| 118 | Br | $CF_2Cl$ | Cl | Br | N |
| 119 | F | $CF_2Cl$ | Cl | Br | N |
| 120 | $CF_3$ | $CF_2Cl$ | Cl | Br | N |
| 121 | H | $CF_3$ | Br | Br | N |
| 122 | Cl | $CF_3$ | Br | Br | N |
| 123 | Br | $CF_3$ | Br | Br | N |
| 124 | F | $CF_3$ | Br | Br | N |
| 125 | $CF_3$ | $CF_3$ | Br | Br | N |
| 126 | H | $CF_2Cl$ | Br | Br | N |
| 127 | Cl | $CF_2Cl$ | Br | Br | N |
| 128 | Br | $CF_2Cl$ | Br | Br | N |
| 129 | F | $CF_2Cl$ | Br | Br | N |
| 130 | $CF_3$ | $CF_2Cl$ | Br | Br | N |
| 131 | H | $CF_3$ | F | Br | N |
| 132 | Cl | $CF_3$ | F | Br | N |
| 133 | Br | $CF_3$ | F | Br | N |
| 134 | F | $CF_3$ | F | Br | N |
| 135 | $CF_3$ | $CF_3$ | F | Br | N |
| 136 | H | $CF_2Cl$ | F | Br | N |
| 137 | Cl | $CF_2Cl$ | F | Br | N |
| 138 | Br | $CF_2Cl$ | F | Br | N |
| 139 | F | $CF_2Cl$ | F | Br | N |
| 140 | $CF_3$ | $CF_2Cl$ | F | Br | N |
| 141 | H | $CF_3$ | $CF_3$ | Br | N |
| 142 | Cl | $CF_3$ | $CF_3$ | Br | N |
| 143 | Br | $CF_3$ | $CF_3$ | Br | N |
| 144 | F | $CF_3$ | $CF_3$ | Br | N |
| 145 | $CF_3$ | $CF_3$ | $CF_3$ | Br | N |
| 146 | H | $CF_2Cl$ | $CF_3$ | Br | N |
| 147 | Cl | $CF_2Cl$ | $CF_3$ | Br | N |
| 148 | Br | $CF_2Cl$ | $CF_3$ | Br | N |
| 149 | F | $CF_2Cl$ | $CF_3$ | Br | N |
| 150 | $CF_3$ | $CF_2Cl$ | $CF_3$ | Br | N |
| 151 | H | $CF_3$ | H | $CF_3$ | N |
| 152 | Cl | $CF_3$ | H | $CF_3$ | N |
| 153 | Br | $CF_3$ | H | $CF_3$ | N |
| 154 | F | $CF_3$ | H | $CF_3$ | N |
| 155 | $CF_3$ | $CF_3$ | H | $CF_3$ | N |
| 156 | H | $CF_2Cl$ | H | $CF_3$ | N |
| 157 | Cl | $CF_2Cl$ | H | $CF_3$ | N |
| 158 | Br | $CF_2Cl$ | H | $CF_3$ | N |
| 159 | F | $CF_2Cl$ | H | $CF_3$ | N |
| 160 | $CF_3$ | $CF_2Cl$ | H | $CF_3$ | N |
| 161 | H | $CF_3$ | Cl | $CF_3$ | N |
| 162 | Cl | $CF_3$ | Cl | $CF_3$ | N |
| 163 | Br | $CF_3$ | Cl | $CF_3$ | N |
| 164 | F | $CF_3$ | Cl | $CF_3$ | N |
| 165 | $CF_3$ | $CF_3$ | Cl | $CF_3$ | N |
| 166 | H | $CF_2Cl$ | Cl | $CF_3$ | N |
| 167 | Cl | $CF_2Cl$ | Cl | $CF_3$ | N |
| 168 | Br | $CF_2Cl$ | Cl | $CF_3$ | N |
| 169 | F | $CF_2Cl$ | Cl | $CF_3$ | N |
| 170 | $CF_3$ | $CF_2Cl$ | Cl | $CF_3$ | N |
| 171 | H | $CF_3$ | Br | $CF_3$ | N |
| 172 | Cl | $CF_3$ | Br | $CF_3$ | N |
| 173 | Br | $CF_3$ | Br | $CF_3$ | N |
| 174 | F | $CF_3$ | Br | $CF_3$ | N |
| 175 | $CF_3$ | $CF_3$ | Br | $CF_3$ | N |
| 176 | H | $CF_2Cl$ | Br | $CF_3$ | N |
| 177 | Cl | $CF_2Cl$ | Br | $CF_3$ | N |
| 178 | Br | $CF_2Cl$ | Br | $CF_3$ | N |
| 179 | F | $CF_2Cl$ | Br | $CF_3$ | N |
| 180 | $CF_3$ | $CF_2Cl$ | Br | $CF_3$ | N |
| 181 | H | $CF_3$ | F | $CF_3$ | N |
| 182 | Cl | $CF_3$ | F | $CF_3$ | N |
| 183 | Br | $CF_3$ | F | $CF_3$ | N |
| 184 | F | $CF_3$ | F | $CF_3$ | N |
| 185 | $CF_3$ | $CF_3$ | F | $CF_3$ | N |
| 186 | H | $CF_2Cl$ | F | $CF_3$ | N |
| 187 | Cl | $CF_2Cl$ | F | $CF_3$ | N |
| 188 | Br | $CF_2Cl$ | F | $CF_3$ | N |
| 189 | F | $CF_2Cl$ | F | $CF_3$ | N |
| 190 | $CF_3$ | $CF_2Cl$ | F | $CF_3$ | N |
| 191 | H | $CF_3$ | $CF_3$ | $CF_3$ | N |
| 192 | Cl | $CF_3$ | $CF_3$ | $CF_3$ | N |
| 193 | Br | $CF_3$ | $CF_3$ | $CF_3$ | N |
| 194 | F | $CF_3$ | $CF_3$ | $CF_3$ | N |
| 195 | $CF_3$ | $CF_3$ | $CF_3$ | $CF_3$ | N |
| 196 | H | $CF_2Cl$ | $CF_3$ | $CF_3$ | N |
| 197 | Cl | $CF_2Cl$ | $CF_3$ | $CF_3$ | N |
| 198 | Br | $CF_2Cl$ | $CF_3$ | $CF_3$ | N |
| 199 | F | $CF_2Cl$ | $CF_3$ | $CF_3$ | N |
| 200 | $CF_3$ | $CF_2Cl$ | $CF_3$ | $CF_3$ | N |
| 201 | H | $CF_3$ | H | F | N |
| 202 | Cl | $CF_3$ | H | F | N |
| 203 | Br | $CF_3$ | H | F | N |
| 204 | F | $CF_3$ | H | F | N |
| 205 | $CF_3$ | $CF_3$ | H | F | N |
| 206 | H | $CF_2Cl$ | H | F | N |
| 207 | Cl | $CF_2Cl$ | H | F | N |
| 208 | Br | $CF_2Cl$ | H | F | N |
| 209 | F | $CF_2Cl$ | H | F | N |
| 210 | $CF_3$ | $CF_2Cl$ | H | F | N |
| 211 | H | $CF_3$ | Cl | F | N |
| 212 | Cl | $CF_3$ | Cl | F | N |
| 213 | Br | $CF_3$ | Cl | F | N |
| 214 | F | $CF_3$ | Cl | F | N |
| 215 | $CF_3$ | $CF_3$ | Cl | F | N |
| 216 | H | $CF_2Cl$ | Cl | F | N |
| 217 | Cl | $CF_2Cl$ | Cl | F | N |
| 218 | Br | $CF_2Cl$ | Cl | F | N |
| 219 | F | $CF_2Cl$ | Cl | F | N |
| 220 | $CF_3$ | $CF_2Cl$ | Cl | F | N |
| 221 | H | $CF_3$ | Br | F | N |
| 222 | Cl | $CF_3$ | Br | F | N |
| 223 | Br | $CF_3$ | Br | F | N |
| 224 | F | $CF_3$ | Br | F | N |
| 225 | $CF_3$ | $CF_3$ | Br | F | N |
| 226 | H | $CF_2Cl$ | Br | F | N |
| 227 | Cl | $CF_2Cl$ | Br | F | N |
| 228 | Br | $CF_2Cl$ | Br | F | N |
| 229 | F | $CF_2Cl$ | Br | F | N |
| 230 | $CF_3$ | $CF_2Cl$ | Br | F | N |
| 231 | H | $CF_3$ | F | F | N |
| 232 | Cl | $CF_3$ | F | F | N |
| 233 | Br | $CF_3$ | F | F | N |
| 234 | F | $CF_3$ | F | F | N |
| 235 | $CF_3$ | $CF_3$ | F | F | N |
| 236 | H | $CF_2Cl$ | F | F | N |
| 237 | Cl | $CF_2Cl$ | F | F | N |
| 238 | Br | $CF_2Cl$ | F | F | N |
| 239 | F | $CF_2Cl$ | F | F | N |
| 240 | $CF_3$ | $CF_2Cl$ | F | F | N |
| 241 | H | $CF_3$ | $CF_3$ | F | N |
| 242 | Cl | $CF_3$ | $CF_3$ | F | N |
| 243 | Br | $CF_3$ | $CF_3$ | F | N |
| 244 | F | $CF_3$ | $CF_3$ | F | N |
| 245 | $CF_3$ | $CF_3$ | $CF_3$ | F | N |
| 246 | H | $CF_2Cl$ | $CF_3$ | F | N |
| 247 | Cl | $CF_2Cl$ | $CF_3$ | F | N |
| 248 | Br | $CF_2Cl$ | $CF_3$ | F | N |
| 249 | F | $CF_2Cl$ | $CF_3$ | F | N |
| 250 | $CF_3$ | $CF_2Cl$ | $CF_3$ | F | N |
| 251 | H | $CF_3$ | H | Me | CH |
| 252 | Cl | $CF_3$ | H | Me | CH |
| 253 | Br | $CF_3$ | H | Me | CH |
| 254 | F | $CF_3$ | H | Me | CH |
| 255 | $CF_3$ | $CF_3$ | H | Me | CH |
| 256 | H | $CF_2Cl$ | H | Me | CH |
| 257 | Cl | $CF_2Cl$ | H | Me | CH |

TABLE P-continued

| | $X_3$ | $R^3$ | $X_1$ | $R^5$ | $X_2$ |
|---|---|---|---|---|---|
| 258 | Br | $CF_2Cl$ | H | Me | CH |
| 259 | F | $CF_2Cl$ | H | Me | CH |
| 260 | $CF_3$ | $CF_2Cl$ | H | Me | CH |
| 261 | H | $CF_3$ | Cl | Me | CH |
| 262 | Cl | $CF_3$ | Cl | Me | CH |
| 263 | Br | $CF_3$ | Cl | Me | CH |
| 264 | F | $CF_3$ | Cl | Me | CH |
| 265 | $CF_3$ | $CF_3$ | Cl | Me | CH |
| 266 | H | $CF_2Cl$ | Cl | Me | CH |
| 267 | Cl | $CF_2Cl$ | Cl | Me | CH |
| 268 | Br | $CF_2Cl$ | Cl | Me | CH |
| 269 | F | $CF_2Cl$ | Cl | Me | CH |
| 270 | $CF_3$ | $CF_2Cl$ | Cl | Me | CH |
| 271 | H | $CF_3$ | Br | Me | CH |
| 272 | Cl | $CF_3$ | Br | Me | CH |
| 273 | Br | $CF_3$ | Br | Me | CH |
| 274 | F | $CF_3$ | Br | Me | CH |
| 275 | $CF_3$ | $CF_3$ | Br | Me | CH |
| 276 | H | $CF_2Cl$ | Br | Me | CH |
| 277 | Cl | $CF_2Cl$ | Br | Me | CH |
| 278 | Br | $CF_2Cl$ | Br | Me | CH |
| 279 | F | $CF_2Cl$ | Br | Me | CH |
| 280 | $CF_3$ | $CF_2Cl$ | Br | Me | CH |
| 281 | H | $CF_3$ | F | Me | CH |
| 282 | Cl | $CF_3$ | F | Me | CH |
| 283 | Br | $CF_3$ | F | Me | CH |
| 284 | F | $CF_3$ | F | Me | CH |
| 285 | $CF_3$ | $CF_3$ | F | Me | CH |
| 286 | H | $CF_2Cl$ | F | Me | CH |
| 287 | Cl | $CF_2Cl$ | F | Me | CH |
| 288 | Br | $CF_2Cl$ | F | Me | CH |
| 289 | F | $CF_2Cl$ | F | Me | CH |
| 290 | $CF_3$ | $CF_2Cl$ | F | Me | CH |
| 291 | H | $CF_3$ | $CF_3$ | Me | CH |
| 292 | Cl | $CF_3$ | $CF_3$ | Me | CH |
| 293 | Br | $CF_3$ | $CF_3$ | Me | CH |
| 294 | F | $CF_3$ | $CF_3$ | Me | CH |
| 295 | $CF_3$ | $CF_3$ | $CF_3$ | Me | CH |
| 296 | H | $CF_2Cl$ | $CF_3$ | Me | CH |
| 297 | Cl | $CF_2Cl$ | $CF_3$ | Me | CH |
| 298 | Br | $CF_2Cl$ | $CF_3$ | Me | CH |
| 299 | F | $CF_2Cl$ | $CF_3$ | Me | CH |
| 300 | $CF_3$ | $CF_2Cl$ | $CF_3$ | Me | CH |
| 301 | H | $CF_3$ | H | Cl | CH |
| 302 | Cl | $CF_3$ | H | Cl | CH |
| 303 | Br | $CF_3$ | H | Cl | CH |
| 304 | F | $CF_3$ | H | Cl | CH |
| 305 | $CF_3$ | $CF_3$ | H | Cl | CH |
| 306 | H | $CF_2Cl$ | H | Cl | CH |
| 307 | Cl | $CF_2Cl$ | H | Cl | CH |
| 308 | Br | $CF_2Cl$ | H | Cl | CH |
| 309 | F | $CF_2Cl$ | H | Cl | CH |
| 310 | $CF_3$ | $CF_2Cl$ | H | Cl | CH |
| 311 | H | $CF_3$ | Cl | Cl | CH |
| 312 | Cl | $CF_3$ | Cl | Cl | CH |
| 313 | Br | $CF_3$ | Cl | Cl | CH |
| 314 | F | $CF_3$ | Cl | Cl | CH |
| 315 | $CF_3$ | $CF_3$ | Cl | Cl | CH |
| 316 | H | $CF_2Cl$ | Cl | Cl | CH |
| 317 | Cl | $CF_2Cl$ | Cl | Cl | CH |
| 318 | Br | $CF_2Cl$ | Cl | Cl | CH |
| 319 | F | $CF_2Cl$ | Cl | Cl | CH |
| 320 | $CF_3$ | $CF_2Cl$ | Cl | Cl | CH |
| 321 | H | $CF_3$ | Br | Cl | CH |
| 322 | Cl | $CF_3$ | Br | Cl | CH |
| 323 | Br | $CF_3$ | Br | Cl | CH |
| 324 | F | $CF_3$ | Br | Cl | CH |
| 325 | $CF_3$ | $CF_3$ | Br | Cl | CH |
| 326 | H | $CF_2Cl$ | Br | Cl | CH |
| 327 | Cl | $CF_2Cl$ | Br | Cl | CH |
| 328 | Br | $CF_2Cl$ | Br | Cl | CH |
| 329 | F | $CF_2Cl$ | Br | Cl | CH |
| 330 | $CF_3$ | $CF_2Cl$ | Br | Cl | CH |
| 331 | H | $CF_3$ | F | Cl | CH |
| 332 | Cl | $CF_3$ | F | Cl | CH |
| 333 | Br | $CF_3$ | F | Cl | CH |
| 334 | F | $CF_3$ | F | Cl | CH |
| 335 | $CF_3$ | $CF_3$ | F | Cl | CH |
| 336 | H | $CF_2Cl$ | F | Cl | CH |
| 337 | Cl | $CF_2Cl$ | F | Cl | CH |
| 338 | Br | $CF_2Cl$ | F | Cl | CH |
| 339 | F | $CF_2Cl$ | F | Cl | CH |
| 340 | $CF_3$ | $CF_2Cl$ | F | Cl | CH |
| 341 | H | $CF_3$ | $CF_3$ | Cl | CH |
| 342 | Cl | $CF_3$ | $CF_3$ | Cl | CH |
| 343 | Br | $CF_3$ | $CF_3$ | Cl | CH |
| 344 | F | $CF_3$ | $CF_3$ | Cl | CH |
| 345 | $CF_3$ | $CF_3$ | $CF_3$ | Cl | CH |
| 346 | H | $CF_2Cl$ | $CF_3$ | Cl | CH |
| 347 | Cl | $CF_2Cl$ | $CF_3$ | Cl | CH |
| 348 | Br | $CF_2Cl$ | $CF_3$ | Cl | CH |
| 349 | F | $CF_2Cl$ | $CF_3$ | Cl | CH |
| 350 | $CF_3$ | $CF_2Cl$ | $CF_3$ | Cl | CH |
| 351 | H | $CF_3$ | H | Br | CH |
| 352 | Cl | $CF_3$ | H | Br | CH |
| 353 | Br | $CF_3$ | H | Br | CH |
| 354 | F | $CF_3$ | H | Br | CH |
| 355 | $CF_3$ | $CF_3$ | H | Br | CH |
| 356 | H | $CF_2Cl$ | H | Br | CH |
| 357 | Cl | $CF_2Cl$ | H | Br | CH |
| 358 | Br | $CF_2Cl$ | H | Br | CH |
| 359 | F | $CF_2Cl$ | H | Br | CH |
| 360 | $CF_3$ | $CF_2Cl$ | H | Br | CH |
| 361 | H | $CF_3$ | Cl | Br | CH |
| 362 | Cl | $CF_3$ | Cl | Br | CH |
| 363 | Br | $CF_3$ | Cl | Br | CH |
| 364 | F | $CF_3$ | Cl | Br | CH |
| 365 | $CF_3$ | $CF_3$ | Cl | Br | CH |
| 366 | H | $CF_2Cl$ | Cl | Br | CH |
| 367 | Cl | $CF_2Cl$ | Cl | Br | CH |
| 368 | Br | $CF_2Cl$ | Cl | Br | CH |
| 369 | F | $CF_2Cl$ | Cl | Br | CH |
| 370 | $CF_3$ | $CF_2Cl$ | Cl | Br | CH |
| 371 | H | $CF_3$ | Br | Br | CH |
| 372 | Cl | $CF_3$ | Br | Br | CH |
| 373 | Br | $CF_3$ | Br | Br | CH |
| 374 | F | $CF_3$ | Br | Br | CH |
| 375 | $CF_3$ | $CF_3$ | Br | Br | CH |
| 376 | H | $CF_2Cl$ | Br | Br | CH |
| 377 | Cl | $CF_2Cl$ | Br | Br | CH |
| 378 | Br | $CF_2Cl$ | Br | Br | CH |
| 379 | F | $CF_2Cl$ | Br | Br | CH |
| 380 | $CF_3$ | $CF_2Cl$ | Br | Br | CH |
| 381 | H | $CF_3$ | F | Br | CH |
| 382 | Cl | $CF_3$ | F | Br | CH |
| 383 | Br | $CF_3$ | F | Br | CH |
| 384 | F | $CF_3$ | F | Br | CH |
| 385 | $CF_3$ | $CF_3$ | F | Br | CH |
| 386 | H | $CF_2Cl$ | F | Br | CH |
| 387 | Cl | $CF_2Cl$ | F | Br | CH |
| 388 | Br | $CF_2Cl$ | F | Br | CH |
| 389 | F | $CF_2Cl$ | F | Br | CH |
| 390 | $CF_3$ | $CF_2Cl$ | F | Br | CH |
| 391 | H | $CF_3$ | $CF_3$ | Br | CH |
| 392 | Cl | $CF_3$ | $CF_3$ | Br | CH |
| 393 | Br | $CF_3$ | $CF_3$ | Br | CH |
| 394 | F | $CF_3$ | $CF_3$ | Br | CH |
| 395 | $CF_3$ | $CF_3$ | $CF_3$ | Br | CH |
| 396 | H | $CF_2Cl$ | $CF_3$ | Br | CH |
| 397 | Cl | $CF_2Cl$ | $CF_3$ | Br | CH |
| 398 | Br | $CF_2Cl$ | $CF_3$ | Br | CH |
| 399 | F | $CF_2Cl$ | $CF_3$ | Br | CH |
| 400 | $CF_3$ | $CF_2Cl$ | $CF_3$ | Br | CH |
| 401 | H | $CF_3$ | H | $CF_3$ | CH |
| 402 | Cl | $CF_3$ | H | $CF_3$ | CH |
| 403 | Br | $CF_3$ | H | $CF_3$ | CH |
| 404 | F | $CF_3$ | H | $CF_3$ | CH |
| 405 | $CF_3$ | $CF_3$ | H | $CF_3$ | CH |
| 406 | H | $CF_2Cl$ | H | $CF_3$ | CH |
| 407 | Cl | $CF_2Cl$ | H | $CF_3$ | CH |
| 408 | Br | $CF_2Cl$ | H | $CF_3$ | CH |
| 409 | F | $CF_2Cl$ | H | $CF_3$ | CH |
| 410 | $CF_3$ | $CF_2Cl$ | H | $CF_3$ | CH |
| 411 | H | $CF_3$ | Cl | $CF_3$ | CH |
| 412 | Cl | $CF_3$ | Cl | $CF_3$ | CH |
| 413 | Br | $CF_3$ | Cl | $CF_3$ | CH |

TABLE P-continued

| | X₃ | R³ | X₁ | R⁵ | X₂ |
|---|---|---|---|---|---|
| 414 | F | CF₃ | Cl | CF₃ | CH |
| 415 | CF₃ | CF₃ | Cl | CF₃ | CH |
| 416 | H | CF₂Cl | Cl | CF₃ | CH |
| 417 | Cl | CF₂Cl | Cl | CF₃ | CH |
| 418 | Br | CF₂Cl | Cl | CF₃ | CH |
| 419 | F | CF₂Cl | Cl | CF₃ | CH |
| 420 | CF₃ | CF₂Cl | Cl | CF₃ | CH |
| 421 | H | CF₃ | Br | CF₃ | CH |
| 422 | Cl | CF₃ | Br | CF₃ | CH |
| 423 | Br | CF₃ | Br | CF₃ | CH |
| 424 | F | CF₃ | Br | CF₃ | CH |
| 425 | CF₃ | CF₃ | Br | CF₃ | CH |
| 426 | H | CF₂Cl | Br | CF₃ | CH |
| 427 | Cl | CF₂Cl | Br | CF₃ | CH |
| 428 | Br | CF₂Cl | Br | CF₃ | CH |
| 429 | F | CF₂Cl | Br | CF₃ | CH |
| 430 | CF₃ | CF₂Cl | Br | CF₃ | CH |
| 431 | H | CF₃ | F | CF₃ | CH |
| 432 | Cl | CF₃ | F | CF₃ | CH |
| 433 | Br | CF₃ | F | CF₃ | CH |
| 434 | F | CF₃ | F | CF₃ | CH |
| 435 | CF₃ | CF₃ | F | CF₃ | CH |
| 436 | H | CF₂Cl | F | CF₃ | CH |
| 437 | Cl | CF₂Cl | F | CF₃ | CH |
| 438 | Br | CF₂Cl | F | CF₃ | CH |
| 439 | F | CF₂Cl | F | CF₃ | CH |
| 440 | CF₃ | CF₂Cl | F | CF₃ | CH |
| 441 | H | CF₃ | CF₃ | CF₃ | CH |
| 442 | Cl | CF₃ | CF₃ | CF₃ | CH |
| 443 | Br | CF₃ | CF₃ | CF₃ | CH |
| 444 | F | CF₃ | CF₃ | CF₃ | CH |
| 445 | CF₃ | CF₃ | CF₃ | CF₃ | CH |
| 446 | H | CF₂Cl | CF₃ | CF₃ | CH |
| 447 | Cl | CF₂Cl | CF₃ | CF₃ | CH |
| 448 | Br | CF₂Cl | CF₃ | CF₃ | CH |
| 449 | F | CF₂Cl | CF₃ | CF₃ | CH |
| 450 | CF₃ | CF₂Cl | CF₃ | CF₃ | CH |
| 451 | H | CF₃ | H | F | CH |
| 452 | Cl | CF₃ | H | F | CH |
| 453 | Br | CF₃ | H | F | CH |
| 454 | F | CF₃ | H | F | CH |
| 455 | CF₃ | CF₃ | H | F | CH |
| 456 | H | CF₂Cl | H | F | CH |
| 457 | Cl | CF₂Cl | H | F | CH |
| 458 | Br | CF₂Cl | H | F | CH |
| 459 | F | CF₂Cl | H | F | CH |
| 460 | CF₃ | CF₂Cl | H | F | CH |
| 461 | H | CF₃ | Cl | F | CH |
| 462 | Cl | CF₃ | Cl | F | CH |
| 463 | Br | CF₃ | Cl | F | CH |
| 464 | F | CF₃ | Cl | F | CH |
| 465 | CF₃ | CF₃ | Cl | F | CH |
| 466 | H | CF₂Cl | Cl | F | CH |
| 467 | Cl | CF₂Cl | Cl | F | CH |
| 468 | Br | CF₂Cl | Cl | F | CH |
| 469 | F | CF₂Cl | Cl | F | CH |
| 470 | CF₃ | CF₂Cl | Cl | F | CH |
| 471 | H | CF₃ | Br | F | CH |
| 472 | Cl | CF₃ | Br | F | CH |
| 473 | Br | CF₃ | Br | F | CH |
| 474 | F | CF₃ | Br | F | CH |
| 475 | CF₃ | CF₃ | Br | F | CH |
| 476 | H | CF₂Cl | Br | F | CH |
| 477 | Cl | CF₂Cl | Br | F | CH |
| 478 | Br | CF₂Cl | Br | F | CH |
| 479 | F | CF₂Cl | Br | F | CH |
| 480 | CF₃ | CF₂Cl | Br | F | CH |
| 481 | H | CF₃ | F | F | CH |
| 482 | Cl | CF₃ | F | F | CH |
| 483 | Br | CF₃ | F | F | CH |
| 484 | F | CF₃ | F | F | CH |
| 485 | CF₃ | CF₃ | F | F | CH |
| 486 | H | CF₂Cl | F | F | CH |
| 487 | Cl | CF₂Cl | F | F | CH |
| 488 | Br | CF₂Cl | F | F | CH |
| 489 | F | CF₂Cl | F | F | CH |
| 490 | CF₃ | CF₂Cl | F | F | CH |
| 491 | H | CF₃ | CF₃ | F | CH |
| 492 | Cl | CF₃ | CF₃ | F | CH |
| 493 | Br | CF₃ | CF₃ | F | CH |
| 494 | F | CF₃ | CF₃ | F | CH |
| 495 | CF₃ | CF₃ | CF₃ | F | CH |
| 496 | H | CF₂Cl | CF₃ | F | CH |
| 497 | Cl | CF₂Cl | CF₃ | F | CH |
| 498 | Br | CF₂Cl | CF₃ | F | CH |
| 499 | F | CF₂Cl | CF₃ | F | CH |
| 500 | CF₃ | CF₂Cl | CF₃ | F | CH |
| 501 | H | CF₃ | H | Me | CF |
| 502 | Cl | CF₃ | H | Me | CF |
| 503 | Br | CF₃ | H | Me | CF |
| 504 | F | CF₃ | H | Me | CF |
| 505 | CF₃ | CF₃ | H | Me | CF |
| 506 | H | CF₂Cl | H | Me | CF |
| 507 | Cl | CF₂Cl | H | Me | CF |
| 508 | Br | CF₂Cl | H | Me | CF |
| 509 | F | CF₂Cl | H | Me | CF |
| 510 | CF₃ | CF₂Cl | H | Me | CF |
| 511 | H | CF₃ | Cl | Me | CF |
| 512 | Cl | CF₃ | Cl | Me | CF |
| 513 | Br | CF₃ | Cl | Me | CF |
| 514 | F | CF₃ | Cl | Me | CF |
| 515 | CF₃ | CF₃ | Cl | Me | CF |
| 516 | H | CF₂Cl | Cl | Me | CF |
| 517 | Cl | CF₂Cl | Cl | Me | CF |
| 518 | Br | CF₂Cl | Cl | Me | CF |
| 519 | F | CF₂Cl | Cl | Me | CF |
| 520 | CF₃ | CF₂Cl | Cl | Me | CF |
| 521 | H | CF₃ | Br | Me | CF |
| 522 | Cl | CF₃ | Br | Me | CF |
| 523 | Br | CF₃ | Br | Me | CF |
| 524 | F | CF₃ | Br | Me | CF |
| 525 | CF₃ | CF₃ | Br | Me | CF |
| 526 | H | CF₂Cl | Br | Me | CF |
| 527 | Cl | CF₂Cl | Br | Me | CF |
| 528 | Br | CF₂Cl | Br | Me | CF |
| 529 | F | CF₂Cl | Br | Me | CF |
| 530 | CF₃ | CF₂Cl | Br | Me | CF |
| 531 | H | CF₃ | F | Me | CF |
| 532 | Cl | CF₃ | F | Me | CF |
| 533 | Br | CF₃ | F | Me | CF |
| 534 | F | CF₃ | F | Me | CF |
| 535 | CF₃ | CF₃ | F | Me | CF |
| 536 | H | CF₂Cl | F | Me | CF |
| 537 | Cl | CF₂Cl | F | Me | CF |
| 538 | Br | CF₂Cl | F | Me | CF |
| 539 | F | CF₂Cl | F | Me | CF |
| 540 | CF₃ | CF₂Cl | F | Me | CF |
| 541 | H | CF₃ | CF₃ | Me | CF |
| 542 | Cl | CF₃ | CF₃ | Me | CF |
| 543 | Br | CF₃ | CF₃ | Me | CF |
| 544 | F | CF₃ | CF₃ | Me | CF |
| 545 | CF₃ | CF₃ | CF₃ | Me | CF |
| 546 | H | CF₂Cl | CF₃ | Me | CF |
| 547 | Cl | CF₂Cl | CF₃ | Me | CF |
| 548 | Br | CF₂Cl | CF₃ | Me | CF |
| 549 | F | CF₂Cl | CF₃ | Me | CF |
| 550 | CF₃ | CF₂Cl | CF₃ | Me | CF |
| 551 | H | CF₃ | H | Cl | CF |
| 552 | Cl | CF₃ | H | Cl | CF |
| 553 | Br | CF₃ | H | Cl | CF |
| 554 | F | CF₃ | H | Cl | CF |
| 555 | CF₃ | CF₃ | H | Cl | CF |
| 556 | H | CF₂Cl | H | Cl | CF |
| 557 | Cl | CF₂Cl | H | Cl | CF |
| 558 | Br | CF₂Cl | H | Cl | CF |
| 559 | F | CF₂Cl | H | Cl | CF |
| 560 | CF₃ | CF₂Cl | H | Cl | CF |
| 561 | H | CF₃ | Cl | Cl | CF |
| 562 | Cl | CF₃ | Cl | Cl | CF |
| 563 | Br | CF₃ | Cl | Cl | CF |
| 564 | F | CF₃ | Cl | Cl | CF |
| 565 | CF₃ | CF₃ | Cl | Cl | CF |
| 566 | H | CF₂Cl | Cl | Cl | CF |
| 567 | Cl | CF₂Cl | Cl | Cl | CF |
| 568 | Br | CF₂Cl | Cl | Cl | CF |
| 569 | F | CF₂Cl | Cl | Cl | CF |

TABLE P-continued

| | X₃ | R³ | X₁ | R⁵ | X₂ |
|---|---|---|---|---|---|
| 570 | CF₃ | CF₂Cl | Cl | Cl | CF |
| 571 | H | CF₃ | Br | Cl | CF |
| 572 | Cl | CF₃ | Br | Cl | CF |
| 573 | Br | CF₃ | Br | Cl | CF |
| 574 | F | CF₃ | Br | Cl | CF |
| 575 | CF₃ | CF₃ | Br | Cl | CF |
| 576 | H | CF₂Cl | Br | Cl | CF |
| 577 | Cl | CF₂Cl | Br | Cl | CF |
| 578 | Br | CF₂Cl | Br | Cl | CF |
| 579 | F | CF₂Cl | Br | Cl | CF |
| 580 | CF₃ | CF₂Cl | Br | Cl | CF |
| 581 | H | CF₃ | F | Cl | CF |
| 582 | Cl | CF₃ | F | Cl | CF |
| 583 | Br | CF₃ | F | Cl | CF |
| 584 | F | CF₃ | F | Cl | CF |
| 585 | CF₃ | CF₃ | F | Cl | CF |
| 586 | H | CF₂Cl | F | Cl | CF |
| 587 | Cl | CF₂Cl | F | Cl | CF |
| 588 | Br | CF₂Cl | F | Cl | CF |
| 589 | F | CF₂Cl | F | Cl | CF |
| 590 | CF₃ | CF₂Cl | F | Cl | CF |
| 591 | H | CF₃ | CF₃ | Cl | CF |
| 592 | Cl | CF₃ | CF₃ | Cl | CF |
| 593 | Br | CF₃ | CF₃ | Cl | CF |
| 594 | F | CF₃ | CF₃ | Cl | CF |
| 595 | CF₃ | CF₃ | CF₃ | Cl | CF |
| 596 | H | CF₂Cl | CF₃ | Cl | CF |
| 597 | Cl | CF₂Cl | CF₃ | Cl | CF |
| 598 | Br | CF₂Cl | CF₃ | Cl | CF |
| 599 | F | CF₂Cl | CF₃ | Cl | CF |
| 600 | CF₃ | CF₂Cl | CF₃ | Cl | CF |
| 601 | H | CF₃ | H | Br | CF |
| 602 | Cl | CF₃ | H | Br | CF |
| 603 | Br | CF₃ | H | Br | CF |
| 604 | F | CF₃ | H | Br | CF |
| 605 | CF₃ | CF₃ | H | Br | CF |
| 606 | H | CF₂Cl | H | Br | CF |
| 607 | Cl | CF₂Cl | H | Br | CF |
| 608 | Br | CF₂Cl | H | Br | CF |
| 609 | F | CF₂Cl | H | Br | CF |
| 610 | CF₃ | CF₂Cl | H | Br | CF |
| 611 | H | CF₃ | Cl | Br | CF |
| 612 | Cl | CF₃ | Cl | Br | CF |
| 613 | Br | CF₃ | Cl | Br | CF |
| 614 | F | CF₃ | Cl | Br | CF |
| 615 | CF₃ | CF₃ | Cl | Br | CF |
| 616 | H | CF₂Cl | Cl | Br | CF |
| 617 | Cl | CF₂Cl | Cl | Br | CF |
| 618 | Br | CF₂Cl | Cl | Br | CF |
| 619 | F | CF₂Cl | Cl | Br | CF |
| 620 | CF₃ | CF₂Cl | Cl | Br | CF |
| 621 | H | CF₃ | Br | Br | CF |
| 622 | Cl | CF₃ | Br | Br | CF |
| 623 | Br | CF₃ | Br | Br | CF |
| 624 | F | CF₃ | Br | Br | CF |
| 625 | CF₃ | CF₃ | Br | Br | CF |
| 626 | H | CF₂Cl | Br | Br | CF |
| 627 | Cl | CF₂Cl | Br | Br | CF |
| 628 | Br | CF₂Cl | Br | Br | CF |
| 629 | F | CF₂Cl | Br | Br | CF |
| 630 | CF₃ | CF₂Cl | Br | Br | CF |
| 631 | H | CF₃ | F | Br | CF |
| 632 | Cl | CF₃ | F | Br | CF |
| 633 | Br | CF₃ | F | Br | CF |
| 634 | F | CF₃ | F | Br | CF |
| 635 | CF₃ | CF₃ | F | Br | CF |
| 636 | H | CF₂Cl | F | Br | CF |
| 637 | Cl | CF₂Cl | F | Br | CF |
| 638 | Br | CF₂Cl | F | Br | CF |
| 639 | F | CF₂Cl | F | Br | CF |
| 640 | CF₃ | CF₂Cl | F | Br | CF |
| 641 | H | CF₃ | CF₃ | Br | CF |
| 642 | Cl | CF₃ | CF₃ | Br | CF |
| 643 | Br | CF₃ | CF₃ | Br | CF |
| 644 | F | CF₃ | CF₃ | Br | CF |
| 645 | CF₃ | CF₃ | CF₃ | Br | CF |
| 646 | H | CF₂Cl | CF₃ | Br | CF |
| 647 | Cl | CF₂Cl | CF₃ | Br | CF |
| 648 | Br | CF₂Cl | CF₃ | Br | CF |
| 649 | F | CF₂Cl | CF₃ | Br | CF |
| 650 | CF₃ | CF₂Cl | CF₃ | Br | CF |
| 651 | H | CF₃ | H | CF₃ | CF |
| 652 | Cl | CF₃ | H | CF₃ | CF |
| 653 | Br | CF₃ | H | CF₃ | CF |
| 654 | F | CF₃ | H | CF₃ | CF |
| 655 | CF₃ | CF₃ | H | CF₃ | CF |
| 656 | H | CF₂Cl | H | CF₃ | CF |
| 657 | Cl | CF₂Cl | H | CF₃ | CF |
| 658 | Br | CF₂Cl | H | CF₃ | CF |
| 659 | F | CF₂Cl | H | CF₃ | CF |
| 660 | CF₃ | CF₂Cl | H | CF₃ | CF |
| 661 | H | CF₃ | Cl | CF₃ | CF |
| 662 | Cl | CF₃ | Cl | CF₃ | CF |
| 663 | Br | CF₃ | Cl | CF₃ | CF |
| 664 | F | CF₃ | Cl | CF₃ | CF |
| 665 | CF₃ | CF₃ | Cl | CF₃ | CF |
| 666 | H | CF₂Cl | Cl | CF₃ | CF |
| 667 | Cl | CF₂Cl | Cl | CF₃ | CF |
| 668 | Br | CF₂Cl | Cl | CF₃ | CF |
| 669 | F | CF₂Cl | Cl | CF₃ | CF |
| 670 | CF₃ | CF₂Cl | Cl | CF₃ | CF |
| 671 | H | CF₃ | Br | CF₃ | CF |
| 672 | Cl | CF₃ | Br | CF₃ | CF |
| 673 | Br | CF₃ | Br | CF₃ | CF |
| 674 | F | CF₃ | Br | CF₃ | CF |
| 675 | CF₃ | CF₃ | Br | CF₃ | CF |
| 676 | H | CF₂Cl | Br | CF₃ | CF |
| 677 | Cl | CF₂Cl | Br | CF₃ | CF |
| 678 | Br | CF₂Cl | Br | CF₃ | CF |
| 679 | F | CF₂Cl | Br | CF₃ | CF |
| 680 | CF₃ | CF₂Cl | Br | CF₃ | CF |
| 681 | H | CF₃ | F | CF₃ | CF |
| 682 | Cl | CF₃ | F | CF₃ | CF |
| 683 | Br | CF₃ | F | CF₃ | CF |
| 684 | F | CF₃ | F | CF₃ | CF |
| 685 | CF₃ | CF₃ | F | CF₃ | CF |
| 686 | H | CF₂Cl | F | CF₃ | CF |
| 687 | Cl | CF₂Cl | F | CF₃ | CF |
| 688 | Br | CF₂Cl | F | CF₃ | CF |
| 689 | F | CF₂Cl | F | CF₃ | CF |
| 690 | CF₃ | CF₂Cl | F | CF₃ | CF |
| 691 | H | CF₃ | CF₃ | CF₃ | CF |
| 692 | Cl | CF₃ | CF₃ | CF₃ | CF |
| 693 | Br | CF₃ | CF₃ | CF₃ | CF |
| 694 | F | CF₃ | CF₃ | CF₃ | CF |
| 695 | CF₃ | CF₃ | CF₃ | CF₃ | CF |
| 696 | H | CF₂Cl | CF₃ | CF₃ | CF |
| 697 | Cl | CF₂Cl | CF₃ | CF₃ | CF |
| 698 | Br | CF₂Cl | CF₃ | CF₃ | CF |
| 699 | F | CF₂Cl | CF₃ | CF₃ | CF |
| 700 | CF₃ | CF₂Cl | CF₃ | CF₃ | CF |
| 701 | H | CF₃ | H | F | CF |
| 702 | Cl | CF₃ | H | F | CF |
| 703 | Br | CF₃ | H | F | CF |
| 704 | F | CF₃ | H | F | CF |
| 705 | CF₃ | CF₃ | H | F | CF |
| 706 | H | CF₂Cl | H | F | CF |
| 707 | Cl | CF₂Cl | H | F | CF |
| 708 | Br | CF₂Cl | H | F | CF |
| 709 | F | CF₂Cl | H | F | CF |
| 710 | CF₃ | CF₂Cl | H | F | CF |
| 711 | H | CF₃ | Cl | F | CF |
| 712 | Cl | CF₃ | Cl | F | CF |
| 713 | Br | CF₃ | Cl | F | CF |
| 714 | F | CF₃ | Cl | F | CF |
| 715 | CF₃ | CF₃ | Cl | F | CF |
| 716 | H | CF₂Cl | Cl | F | CF |
| 717 | Cl | CF₂Cl | Cl | F | CF |
| 718 | Br | CF₂Cl | Cl | F | CF |
| 719 | F | CF₂Cl | Cl | F | CF |
| 720 | CF₃ | CF₂Cl | Cl | F | CF |
| 721 | H | CF₃ | Br | F | CF |
| 722 | Cl | CF₃ | Br | F | CF |
| 723 | Br | CF₃ | Br | F | CF |
| 724 | F | CF₃ | Br | F | CF |
| 725 | CF₃ | CF₃ | Br | F | CF |

TABLE P-continued

| | $X_3$ | $R^3$ | $X_1$ | $R^5$ | $X_2$ |
|---|---|---|---|---|---|
| 726 | H | $CF_2Cl$ | Br | F | CF |
| 727 | Cl | $CF_2Cl$ | Br | F | CF |
| 728 | Br | $CF_2Cl$ | Br | F | CF |
| 729 | F | $CF_2Cl$ | Br | F | CF |
| 730 | $CF_3$ | $CF_2Cl$ | Br | F | CF |
| 731 | H | $CF_3$ | F | F | CF |
| 732 | Cl | $CF_3$ | F | F | CF |
| 733 | Br | $CF_3$ | F | F | CF |
| 734 | F | $CF_3$ | F | F | CF |
| 735 | $CF_3$ | $CF_3$ | F | F | CF |
| 736 | H | $CF_2Cl$ | F | F | CF |
| 737 | Cl | $CF_2Cl$ | F | F | CF |
| 738 | Br | $CF_2Cl$ | F | F | CF |
| 739 | F | $CF_2Cl$ | F | F | CF |
| 740 | $CF_3$ | $CF_2Cl$ | F | F | CF |
| 741 | H | $CF_3$ | $CF_3$ | F | CF |
| 742 | Cl | $CF_3$ | $CF_3$ | F | CF |
| 743 | Br | $CF_3$ | $CF_3$ | F | CF |
| 744 | F | $CF_3$ | $CF_3$ | F | CF |
| 745 | $CF_3$ | $CF_3$ | $CF_3$ | F | CF |
| 746 | H | $CF_2Cl$ | $CF_3$ | F | CF |
| 747 | Cl | $CF_2Cl$ | $CF_3$ | F | CF |
| 748 | Br | $CF_2Cl$ | $CF_3$ | F | CF |
| 749 | F | $CF_2Cl$ | $CF_3$ | F | CF |
| 750 | $CF_3$ | $CF_2Cl$ | $CF_3$ | F | CF |
| 751 | H | $CF_3$ | H | Me | CBr |
| 752 | Cl | $CF_3$ | H | Me | CBr |
| 753 | Br | $CF_3$ | H | Me | CBr |
| 754 | F | $CF_3$ | H | Me | CBr |
| 755 | $CF_3$ | $CF_3$ | H | Me | CBr |
| 756 | H | $CF_2Cl$ | H | Me | CBr |
| 757 | Cl | $CF_2Cl$ | H | Me | CBr |
| 758 | Br | $CF_2Cl$ | H | Me | CBr |
| 759 | F | $CF_2Cl$ | H | Me | CBr |
| 760 | $CF_3$ | $CF_2Cl$ | H | Me | CBr |
| 761 | H | $CF_3$ | Cl | Me | CBr |
| 762 | Cl | $CF_3$ | Cl | Me | CBr |
| 763 | Br | $CF_3$ | Cl | Me | CBr |
| 764 | F | $CF_3$ | Cl | Me | CBr |
| 765 | $CF_3$ | $CF_3$ | Cl | Me | CBr |
| 766 | H | $CF_2Cl$ | Cl | Me | CBr |
| 767 | Cl | $CF_2Cl$ | Cl | Me | CBr |
| 768 | Br | $CF_2Cl$ | Cl | Me | CBr |
| 769 | F | $CF_2Cl$ | Cl | Me | CBr |
| 770 | $CF_3$ | $CF_2Cl$ | Cl | Me | CBr |
| 771 | H | $CF_3$ | Br | Me | CBr |
| 772 | Cl | $CF_3$ | Br | Me | CBr |
| 773 | Br | $CF_3$ | Br | Me | CBr |
| 774 | F | $CF_3$ | Br | Me | CBr |
| 775 | $CF_3$ | $CF_3$ | Br | Me | CBr |
| 776 | H | $CF_2Cl$ | Br | Me | CBr |
| 777 | Cl | $CF_2Cl$ | Br | Me | CBr |
| 778 | Br | $CF_2Cl$ | Br | Me | CBr |
| 779 | F | $CF_2Cl$ | Br | Me | CBr |
| 780 | $CF_3$ | $CF_2Cl$ | Br | Me | CBr |
| 781 | H | $CF_3$ | F | Me | CBr |
| 782 | Cl | $CF_3$ | F | Me | CBr |
| 783 | Br | $CF_3$ | F | Me | CBr |
| 784 | F | $CF_3$ | F | Me | CBr |
| 785 | $CF_3$ | $CF_3$ | F | Me | CBr |
| 786 | H | $CF_2Cl$ | F | Me | CBr |
| 787 | Cl | $CF_2Cl$ | F | Me | CBr |
| 788 | Br | $CF_2Cl$ | F | Me | CBr |
| 789 | F | $CF_2Cl$ | F | Me | CBr |
| 790 | $CF_3$ | $CF_2Cl$ | F | Me | CBr |
| 791 | H | $CF_3$ | $CF_3$ | Me | CBr |
| 792 | Cl | $CF_3$ | $CF_3$ | Me | CBr |
| 793 | Br | $CF_3$ | $CF_3$ | Me | CBr |
| 794 | F | $CF_3$ | $CF_3$ | Me | CBr |
| 795 | $CF_3$ | $CF_3$ | $CF_3$ | Me | CBr |
| 796 | H | $CF_2Cl$ | $CF_3$ | Me | CBr |
| 797 | Cl | $CF_2Cl$ | $CF_3$ | Me | CBr |
| 798 | Br | $CF_2Cl$ | $CF_3$ | Me | CBr |
| 799 | F | $CF_2Cl$ | $CF_3$ | Me | CBr |
| 800 | $CF_3$ | $CF_2Cl$ | $CF_3$ | Me | CBr |
| 801 | H | $CF_3$ | H | Cl | CBr |
| 802 | Cl | $CF_3$ | H | Cl | CBr |
| 803 | Br | $CF_3$ | H | Cl | CBr |
| 804 | F | $CF_3$ | H | Cl | CBr |
| 805 | $CF_3$ | $CF_3$ | H | Cl | CBr |
| 806 | H | $CF_2Cl$ | H | Cl | CBr |
| 807 | Cl | $CF_2Cl$ | H | Cl | CBr |
| 808 | Br | $CF_2Cl$ | H | Cl | CBr |
| 809 | F | $CF_2Cl$ | H | Cl | CBr |
| 810 | $CF_3$ | $CF_2Cl$ | H | Cl | CBr |
| 811 | H | $CF_3$ | Cl | Cl | CBr |
| 812 | Cl | $CF_3$ | Cl | Cl | CBr |
| 813 | Br | $CF_3$ | Cl | Cl | CBr |
| 814 | F | $CF_3$ | Cl | Cl | CBr |
| 815 | $CF_3$ | $CF_3$ | Cl | Cl | CBr |
| 816 | H | $CF_2Cl$ | Cl | Cl | CBr |
| 817 | Cl | $CF_2Cl$ | Cl | Cl | CBr |
| 818 | Br | $CF_2Cl$ | Cl | Cl | CBr |
| 819 | F | $CF_2Cl$ | Cl | Cl | CBr |
| 820 | $CF_3$ | $CF_2Cl$ | Cl | Cl | CBr |
| 821 | H | $CF_3$ | Br | Cl | CBr |
| 822 | Cl | $CF_3$ | Br | Cl | CBr |
| 823 | Br | $CF_3$ | Br | Cl | CBr |
| 824 | F | $CF_3$ | Br | Cl | CBr |
| 825 | $CF_3$ | $CF_3$ | Br | Cl | CBr |
| 826 | H | $CF_2Cl$ | Br | Cl | CBr |
| 827 | Cl | $CF_2Cl$ | Br | Cl | CBr |
| 828 | Br | $CF_2Cl$ | Br | Cl | CBr |
| 829 | F | $CF_2Cl$ | Br | Cl | CBr |
| 830 | $CF_3$ | $CF_2Cl$ | Br | Cl | CBr |
| 831 | H | $CF_3$ | F | Cl | CBr |
| 832 | Cl | $CF_3$ | F | Cl | CBr |
| 833 | Br | $CF_3$ | F | Cl | CBr |
| 834 | F | $CF_3$ | F | Cl | CBr |
| 835 | $CF_3$ | $CF_3$ | F | Cl | CBr |
| 836 | H | $CF_2Cl$ | F | Cl | CBr |
| 837 | Cl | $CF_2Cl$ | F | Cl | CBr |
| 838 | Br | $CF_2Cl$ | F | Cl | CBr |
| 839 | F | $CF_2Cl$ | F | Cl | CBr |
| 840 | $CF_3$ | $CF_2Cl$ | F | Cl | CBr |
| 841 | H | $CF_3$ | $CF_3$ | Cl | CBr |
| 842 | Cl | $CF_3$ | $CF_3$ | Cl | CBr |
| 843 | Br | $CF_3$ | $CF_3$ | Cl | CBr |
| 844 | F | $CF_3$ | $CF_3$ | Cl | CBr |
| 845 | $CF_3$ | $CF_3$ | $CF_3$ | Cl | CBr |
| 846 | H | $CF_2Cl$ | $CF_3$ | Cl | CBr |
| 847 | Cl | $CF_2Cl$ | $CF_3$ | Cl | CBr |
| 848 | Br | $CF_2Cl$ | $CF_3$ | Cl | CBr |
| 849 | F | $CF_2Cl$ | $CF_3$ | Cl | CBr |
| 850 | $CF_3$ | $CF_2Cl$ | $CF_3$ | Cl | CBr |
| 851 | H | $CF_3$ | H | Br | CBr |
| 852 | Cl | $CF_3$ | H | Br | CBr |
| 853 | Br | $CF_3$ | H | Br | CBr |
| 854 | F | $CF_3$ | H | Br | CBr |
| 855 | $CF_3$ | $CF_3$ | H | Br | CBr |
| 886 | H | $CF_2Cl$ | H | Br | CBr |
| 857 | Cl | $CF_2Cl$ | H | Br | CBr |
| 858 | Br | $CF_2Cl$ | H | Br | CBr |
| 859 | F | $CF_2Cl$ | H | Br | CBr |
| 860 | $CF_3$ | $CF_2Cl$ | H | Br | CBr |
| 861 | H | $CF_3$ | Cl | Br | CBr |
| 862 | Cl | $CF_3$ | Cl | Br | CBr |
| 863 | Br | $CF_3$ | Cl | Br | CBr |
| 864 | F | $CF_3$ | Cl | Br | CBr |
| 865 | $CF_3$ | $CF_3$ | Cl | Br | CBr |
| 866 | H | $CF_2Cl$ | Cl | Br | CBr |
| 867 | Cl | $CF_2Cl$ | Cl | Br | CBr |
| 868 | Br | $CF_2Cl$ | Cl | Br | CBr |
| 869 | F | $CF_2Cl$ | Cl | Br | CBr |
| 870 | $CF_3$ | $CF_2Cl$ | Cl | Br | CBr |
| 871 | H | $CF_3$ | Br | Br | CBr |
| 872 | Cl | $CF_3$ | Br | Br | CBr |
| 873 | Br | $CF_3$ | Br | Br | CBr |
| 874 | F | $CF_3$ | Br | Br | CBr |
| 875 | $CF_3$ | $CF_3$ | Br | Br | CBr |
| 876 | H | $CF_2Cl$ | Br | Br | CBr |
| 877 | Cl | $CF_2Cl$ | Br | Br | CBr |
| 878 | Br | $CF_2Cl$ | Br | Br | CBr |
| 879 | F | $CF_2Cl$ | Br | Br | CBr |
| 880 | $CF_3$ | $CF_2Cl$ | Br | Br | CBr |
| 881 | H | $CF_3$ | F | Br | CBr |

TABLE P-continued

| | X₃ | R³ | X₁ | R⁵ | X₂ |
|---|---|---|---|---|---|
| 882 | Cl | CF₃ | F | Br | CBr |
| 883 | Br | CF₃ | F | Br | CBr |
| 884 | F | CF₃ | F | Br | CBr |
| 885 | CF₃ | CF₃ | F | Br | CBr |
| 886 | H | CF₂Cl | F | Br | CBr |
| 887 | Cl | CF₂Cl | F | Br | CBr |
| 888 | Br | CF₂Cl | F | Br | CBr |
| 889 | F | CF₂Cl | F | Br | CBr |
| 890 | CF₃ | CF₂Cl | F | Br | CBr |
| 891 | H | CF₃ | CF₃ | Br | CBr |
| 892 | Cl | CF₃ | CF₃ | Br | CBr |
| 893 | Br | CF₃ | CF₃ | Br | CBr |
| 894 | F | CF₃ | CF₃ | Br | CBr |
| 895 | CF₃ | CF₃ | CF₃ | Br | CBr |
| 896 | H | CF₂Cl | CF₃ | Br | CBr |
| 897 | Cl | CF₂Cl | CF₃ | Br | CBr |
| 898 | Br | CF₂Cl | CF₃ | Br | CBr |
| 899 | F | CF₂Cl | CF₃ | Br | CBr |
| 900 | CF₃ | CF₂Cl | CF₃ | Br | CBr |
| 901 | H | CF₃ | H | CF₃ | CBr |
| 902 | Cl | CF₃ | H | CF₃ | CBr |
| 903 | Br | CF₃ | H | CF₃ | CBr |
| 904 | F | CF₃ | H | CF₃ | CBr |
| 905 | CF₃ | CF₃ | H | CF₃ | CBr |
| 906 | H | CF₂Cl | H | CF₃ | CBr |
| 907 | Cl | CF₂Cl | H | CF₃ | CBr |
| 908 | Br | CF₂Cl | H | CF₃ | CBr |
| 909 | F | CF₂Cl | H | CF₃ | CBr |
| 910 | CF₃ | CF₂Cl | H | CF₃ | CBr |
| 911 | H | CF₃ | Cl | CF₃ | CBr |
| 912 | Cl | CF₃ | Cl | CF₃ | CBr |
| 913 | Br | CF₃ | Cl | CF₃ | CBr |
| 914 | F | CF₃ | Cl | CF₃ | CBr |
| 915 | CF₃ | CF₃ | Cl | CF₃ | CBr |
| 916 | H | CF₂Cl | Cl | CF₃ | CBr |
| 917 | Cl | CF₂Cl | Cl | CF₃ | CBr |
| 918 | Br | CF₂Cl | Cl | CF₃ | CBr |
| 919 | F | CF₂Cl | Cl | CF₃ | CBr |
| 920 | CF₃ | CF₂Cl | Cl | CF₃ | CBr |
| 921 | H | CF₃ | Br | CF₃ | CBr |
| 922 | Cl | CF₃ | Br | CF₃ | CBr |
| 923 | Br | CF₃ | Br | CF₃ | CBr |
| 924 | F | CF₃ | Br | CF₃ | CBr |
| 925 | CF₃ | CF₃ | Br | CF₃ | CBr |
| 926 | H | CF₂Cl | Br | CF₃ | CBr |
| 927 | Cl | CF₂Cl | Br | CF₃ | CBr |
| 928 | Br | CF₂Cl | Br | CF₃ | CBr |
| 929 | F | CF₂Cl | Br | CF₃ | CBr |
| 930 | CF₃ | CF₂Cl | Br | CF₃ | CBr |
| 931 | H | CF₃ | F | CF₃ | CBr |
| 932 | Cl | CF₃ | F | CF₃ | CBr |
| 933 | Br | CF₃ | F | CF₃ | CBr |
| 934 | F | CF₃ | F | CF₃ | CBr |
| 935 | CF₃ | CF₃ | F | CF₃ | CBr |
| 936 | H | CF₂Cl | F | CF₃ | CBr |
| 937 | Cl | CF₂Cl | F | CF₃ | CBr |
| 938 | Br | CF₂Cl | F | CF₃ | CBr |
| 939 | F | CF₂Cl | F | CF₃ | CBr |
| 940 | CF₃ | CF₂Cl | F | CF₃ | CBr |
| 941 | H | CF₃ | CF₃ | CF₃ | CBr |
| 942 | Cl | CF₃ | CF₃ | CF₃ | CBr |
| 943 | Br | CF₃ | CF₃ | CF₃ | CBr |
| 944 | F | CF₃ | CF₃ | CF₃ | CBr |
| 945 | CF₃ | CF₃ | CF₃ | CF₃ | CBr |
| 946 | H | CF₂Cl | CF₃ | CF₃ | CBr |
| 947 | Cl | CF₂Cl | CF₃ | CF₃ | CBr |
| 948 | Br | CF₂Cl | CF₃ | CF₃ | CBr |
| 949 | F | CF₂Cl | CF₃ | CF₃ | CBr |
| 950 | CF₃ | CF₂Cl | CF₃ | CF₃ | CBr |
| 951 | H | CF₃ | H | F | CBr |
| 952 | Cl | CF₃ | H | F | CBr |
| 953 | Br | CF₃ | H | F | CBr |
| 954 | F | CF₃ | H | F | CBr |
| 955 | CF₃ | CF₃ | H | F | CBr |
| 956 | H | CF₂Cl | H | F | CBr |
| 957 | Cl | CF₂Cl | H | F | CBr |
| 958 | Br | CF₂Cl | H | F | CBr |
| 959 | F | CF₂Cl | H | F | CBr |
| 960 | CF₃ | CF₂Cl | H | F | CBr |
| 961 | H | CF₃ | Cl | F | CBr |
| 962 | Cl | CF₃ | Cl | F | CBr |
| 963 | Br | CF₃ | Cl | F | CBr |
| 964 | F | CF₃ | Cl | F | CBr |
| 965 | CF₃ | CF₃ | Cl | F | CBr |
| 966 | H | CF₂Cl | Cl | F | CBr |
| 967 | Cl | CF₂Cl | Cl | F | CBr |
| 968 | Br | CF₂Cl | Cl | F | CBr |
| 969 | F | CF₂Cl | Cl | F | CBr |
| 970 | CF₃ | CF₂Cl | Cl | F | CBr |
| 971 | H | CF₃ | Br | F | CBr |
| 972 | Cl | CF₃ | Br | F | CBr |
| 973 | Br | CF₃ | Br | F | CBr |
| 974 | F | CF₃ | Br | F | CBr |
| 975 | CF₃ | CF₃ | Br | F | CBr |
| 976 | H | CF₂Cl | Br | F | CBr |
| 977 | Cl | CF₂Cl | Br | F | CBr |
| 978 | Br | CF₂Cl | Br | F | CBr |
| 979 | F | CF₂Cl | Br | F | CBr |
| 980 | CF₃ | CF₂Cl | Br | F | CBr |
| 981 | H | CF₃ | F | F | CBr |
| 982 | Cl | CF₃ | F | F | CBr |
| 983 | Br | CF₃ | F | F | CBr |
| 984 | F | CF₃ | F | F | CBr |
| 985 | CF₃ | CF₃ | F | F | CBr |
| 986 | H | CF₂Cl | F | F | CBr |
| 987 | Cl | CF₂Cl | F | F | CBr |
| 988 | Br | CF₂Cl | F | F | CBr |
| 989 | F | CF₂Cl | F | F | CBr |
| 990 | CF₃ | CF₂Cl | F | F | CBr |
| 991 | H | CF₃ | CF₃ | F | CBr |
| 992 | Cl | CF₃ | CF₃ | F | CBr |
| 993 | Br | CF₃ | CF₃ | F | CBr |
| 994 | F | CF₃ | CF₃ | F | CBr |
| 995 | CF₃ | CF₃ | CF₃ | F | CBr |
| 996 | H | CF₂Cl | CF₃ | F | CBr |
| 997 | Cl | CF₂Cl | CF₃ | F | CBr |
| 998 | Br | CF₂Cl | CF₃ | F | CBr |
| 999 | F | CF₂Cl | CF₃ | F | CBr |
| 1000 | CF₃ | CF₂Cl | CF₃ | F | CBr |
| 1001 | H | CF₃ | H | Me | CCl |
| 1002 | Cl | CF₃ | H | Me | CCl |
| 1003 | Br | CF₃ | H | Me | CCl |
| 1004 | F | CF₃ | H | Me | CCl |
| 1005 | CF₃ | CF₃ | H | Me | CCl |
| 1006 | H | CF₂Cl | H | Me | CCl |
| 1007 | Cl | CF₂Cl | H | Me | CCl |
| 1008 | Br | CF₂Cl | H | Me | CCl |
| 1009 | F | CF₂Cl | H | Me | CCl |
| 1010 | CF₃ | CF₂Cl | H | Me | CCl |
| 1011 | H | CF₃ | Cl | Me | CCl |
| 1012 | Cl | CF₃ | Cl | Me | CCl |
| 1013 | Br | CF₃ | Cl | Me | CCl |
| 1014 | F | CF₃ | Cl | Me | CCl |
| 1015 | CF₃ | CF₃ | Cl | Me | CCl |
| 1016 | H | CF₂Cl | Cl | Me | CCl |
| 1017 | Cl | CF₂Cl | Cl | Me | CCl |
| 1018 | Br | CF₂Cl | Cl | Me | CCl |
| 1019 | F | CF₂Cl | Cl | Me | CCl |
| 1020 | CF₃ | CF₂Cl | Cl | Me | CCl |
| 1021 | H | CF₃ | Br | Me | CCl |
| 1022 | Cl | CF₃ | Br | Me | CCl |
| 1023 | Br | CF₃ | Br | Me | CCl |
| 1024 | F | CF₃ | Br | Me | CCl |
| 1025 | CF₃ | CF₃ | Br | Me | CCl |
| 1026 | H | CF₂Cl | Br | Me | CCl |
| 1027 | Cl | CF₂Cl | Br | Me | CCl |
| 1028 | Br | CF₂Cl | Br | Me | CCl |
| 1029 | F | CF₂Cl | Br | Me | CCl |
| 1030 | CF₃ | CF₂Cl | Br | Me | CCl |
| 1031 | H | CF₃ | F | Me | CCl |
| 1032 | Cl | CF₃ | F | Me | CCl |
| 1033 | Br | CF₃ | F | Me | CCl |
| 1034 | F | CF₃ | F | Me | CCl |
| 1035 | CF₃ | CF₃ | F | Me | CCl |
| 1036 | H | CF₂Cl | F | Me | CCl |
| 1037 | Cl | CF₂Cl | F | Me | CCl |

TABLE P-continued

| | $X_3$ | $R^3$ | $X_1$ | $R^5$ | $X_2$ |
|---|---|---|---|---|---|
| 1038 | Br | $CF_2Cl$ | F | Me | CCl |
| 1039 | F | $CF_2Cl$ | F | Me | CCl |
| 1040 | $CF_3$ | $CF_2Cl$ | F | Me | CCl |
| 1041 | H | $CF_3$ | $CF_3$ | Me | CCl |
| 1042 | Cl | $CF_3$ | $CF_3$ | Me | CCl |
| 1043 | Br | $CF_3$ | $CF_3$ | Me | CCl |
| 1044 | F | $CF_3$ | $CF_3$ | Me | CCl |
| 1045 | $CF_3$ | $CF_3$ | $CF_3$ | Me | CCl |
| 1046 | H | $CF_2Cl$ | $CF_3$ | Me | CCl |
| 1047 | Cl | $CF_2Cl$ | $CF_3$ | Me | CCl |
| 1048 | Br | $CF_2Cl$ | $CF_3$ | Me | CCl |
| 1049 | F | $CF_2Cl$ | $CF_3$ | Me | CCl |
| 1050 | $CF_3$ | $CF_2Cl$ | $CF_3$ | Me | CCl |
| 1051 | H | $CF_3$ | H | Cl | CCl |
| 1052 | Cl | $CF_3$ | H | Cl | CCl |
| 1053 | Br | $CF_3$ | H | Cl | CCl |
| 1054 | F | $CF_3$ | H | Cl | CCl |
| 1055 | $CF_3$ | $CF_3$ | H | Cl | CCl |
| 1056 | H | $CF_2Cl$ | H | Cl | CCl |
| 1057 | Cl | $CF_2Cl$ | H | Cl | CCl |
| 1058 | Br | $CF_2Cl$ | H | Cl | CCl |
| 1059 | F | $CF_2Cl$ | H | Cl | CCl |
| 1060 | $CF_3$ | $CF_2Cl$ | H | Cl | CCl |
| 1061 | H | $CF_3$ | Cl | Cl | CCl |
| 1062 | Cl | $CF_3$ | Cl | Cl | CCl |
| 1063 | Br | $CF_3$ | Cl | Cl | CCl |
| 1064 | F | $CF_3$ | Cl | Cl | CCl |
| 1065 | $CF_3$ | $CF_3$ | Cl | Cl | CCl |
| 1066 | H | $CF_2Cl$ | Cl | Cl | CCl |
| 1067 | Cl | $CF_2Cl$ | Cl | Cl | CCl |
| 1068 | Br | $CF_2Cl$ | Cl | Cl | CCl |
| 1069 | F | $CF_2Cl$ | Cl | Cl | CCl |
| 1070 | $CF_3$ | $CF_2Cl$ | Cl | Cl | CCl |
| 1071 | H | $CF_3$ | Br | Cl | CCl |
| 1072 | Cl | $CF_3$ | Br | Cl | CCl |
| 1073 | Br | $CF_3$ | Br | Cl | CCl |
| 1074 | F | $CF_3$ | Br | Cl | CCl |
| 1075 | $CF_3$ | $CF_3$ | Br | Cl | CCl |
| 1076 | H | $CF_2Cl$ | Br | Cl | CCl |
| 1077 | Cl | $CF_2Cl$ | Br | Cl | CCl |
| 1078 | Br | $CF_2Cl$ | Br | Cl | CCl |
| 1079 | F | $CF_2Cl$ | Br | Cl | CCl |
| 1080 | $CF_3$ | $CF_2Cl$ | Br | Cl | CCl |
| 1081 | H | $CF_3$ | F | Cl | CCl |
| 1082 | Cl | $CF_3$ | F | Cl | CCl |
| 1083 | Br | $CF_3$ | F | Cl | CCl |
| 1084 | F | $CF_3$ | F | Cl | CCl |
| 1085 | $CF_3$ | $CF_3$ | F | Cl | CCl |
| 1086 | H | $CF_2Cl$ | F | Cl | CCl |
| 1087 | Cl | $CF_2Cl$ | F | Cl | CCl |
| 1088 | Br | $CF_2Cl$ | F | Cl | CCl |
| 1089 | F | $CF_2Cl$ | F | Cl | CCl |
| 1090 | $CF_3$ | $CF_2Cl$ | F | Cl | CCl |
| 1091 | H | $CF_3$ | $CF_3$ | Cl | CCl |
| 1092 | Cl | $CF_3$ | $CF_3$ | Cl | CCl |
| 1093 | Br | $CF_3$ | $CF_3$ | Cl | CCl |
| 1094 | F | $CF_3$ | $CF_3$ | Cl | CCl |
| 1095 | $CF_3$ | $CF_3$ | $CF_3$ | Cl | CCl |
| 1096 | H | $CF_2Cl$ | $CF_3$ | Cl | CCl |
| 1097 | Cl | $CF_2Cl$ | $CF_3$ | Cl | CCl |
| 1098 | Br | $CF_2Cl$ | $CF_3$ | Cl | CCl |
| 1099 | F | $CF_2Cl$ | $CF_3$ | Cl | CCl |
| 1100 | $CF_3$ | $CF_2Cl$ | $CF_3$ | Cl | CCl |
| 1101 | H | $CF_3$ | H | Br | CCl |
| 1102 | Cl | $CF_3$ | H | Br | CCl |
| 1103 | Br | $CF_3$ | H | Br | CCl |
| 1104 | F | $CF_3$ | H | Br | CCl |
| 1105 | $CF_3$ | $CF_3$ | H | Br | CCl |
| 1106 | H | $CF_2Cl$ | H | Br | CCl |
| 1107 | Cl | $CF_2Cl$ | H | Br | CCl |
| 1108 | Br | $CF_2Cl$ | H | Br | CCl |
| 1109 | F | $CF_2Cl$ | H | Br | CCl |
| 1110 | $CF_3$ | $CF_2Cl$ | H | Br | CCl |
| 1111 | H | $CF_3$ | Cl | Br | CCl |
| 1112 | Cl | $CF_3$ | Cl | Br | CCl |
| 1113 | Br | $CF_3$ | Cl | Br | CCl |
| 1114 | F | $CF_3$ | Cl | Br | CCl |
| 1115 | $CF_3$ | $CF_3$ | Cl | Br | CCl |
| 1116 | H | $CF_2Cl$ | Cl | Br | CCl |
| 1117 | Cl | $CF_2Cl$ | Cl | Br | CCl |
| 1118 | Br | $CF_2Cl$ | Cl | Br | CCl |
| 1119 | F | $CF_2Cl$ | Cl | Br | CCl |
| 1120 | $CF_3$ | $CF_2Cl$ | Cl | Br | CCl |
| 1121 | H | $CF_3$ | Br | Br | CCl |
| 1122 | Cl | $CF_3$ | Br | Br | CCl |
| 1123 | Br | $CF_3$ | Br | Br | CCl |
| 1124 | F | $CF_3$ | Br | Br | CCl |
| 1125 | $CF_3$ | $CF_3$ | Br | Br | CCl |
| 1126 | H | $CF_2Cl$ | Br | Br | CCl |
| 1127 | Cl | $CF_2Cl$ | Br | Br | CCl |
| 1128 | Br | $CF_2Cl$ | Br | Br | CCl |
| 1129 | F | $CF_2Cl$ | Br | Br | CCl |
| 1130 | $CF_3$ | $CF_2Cl$ | Br | Br | CCl |
| 1131 | H | $CF_3$ | F | Br | CCl |
| 1132 | Cl | $CF_3$ | F | Br | CCl |
| 1133 | Br | $CF_3$ | F | Br | CCl |
| 1134 | F | $CF_3$ | F | Br | CCl |
| 1135 | $CF_3$ | $CF_3$ | F | Br | CCl |
| 1136 | H | $CF_2Cl$ | F | Br | CCl |
| 1137 | Cl | $CF_2Cl$ | F | Br | CCl |
| 1138 | Br | $CF_2Cl$ | F | Br | CCl |
| 1139 | F | $CF_2Cl$ | F | Br | CCl |
| 1140 | $CF_3$ | $CF_2Cl$ | F | Br | CCl |
| 1141 | H | $CF_3$ | $CF_3$ | Br | CCl |
| 1142 | Cl | $CF_3$ | $CF_3$ | Br | CCl |
| 1143 | Br | $CF_3$ | $CF_3$ | Br | CCl |
| 1144 | F | $CF_3$ | $CF_3$ | Br | CCl |
| 1145 | $CF_3$ | $CF_3$ | $CF_3$ | Br | CCl |
| 1146 | H | $CF_2Cl$ | $CF_3$ | Br | CCl |
| 1147 | Cl | $CF_2Cl$ | $CF_3$ | Br | CCl |
| 1148 | Br | $CF_2Cl$ | $CF_3$ | Br | CCl |
| 1149 | F | $CF_2Cl$ | $CF_3$ | Br | CCl |
| 1150 | $CF_3$ | $CF_2Cl$ | $CF_3$ | Br | CCl |
| 1151 | H | $CF_3$ | H | $CF_3$ | CCl |
| 1152 | Cl | $CF_3$ | H | $CF_3$ | CCl |
| 1153 | Br | $CF_3$ | H | $CF_3$ | CCl |
| 1154 | F | $CF_3$ | H | $CF_3$ | CCl |
| 1155 | $CF_3$ | $CF_3$ | H | $CF_3$ | CCl |
| 1156 | H | $CF_2Cl$ | H | $CF_3$ | CCl |
| 1157 | Cl | $CF_2Cl$ | H | $CF_3$ | CCl |
| 1158 | Br | $CF_2Cl$ | H | $CF_3$ | CCl |
| 1159 | F | $CF_2Cl$ | H | $CF_3$ | CCl |
| 1160 | $CF_3$ | $CF_2Cl$ | H | $CF_3$ | CCl |
| 1161 | H | $CF_3$ | Cl | $CF_3$ | CCl |
| 1162 | Cl | $CF_3$ | Cl | $CF_3$ | CCl |
| 1163 | Br | $CF_3$ | Cl | $CF_3$ | CCl |
| 1164 | F | $CF_3$ | Cl | $CF_3$ | CCl |
| 1165 | $CF_3$ | $CF_3$ | Cl | $CF_3$ | CCl |
| 1166 | H | $CF_2Cl$ | Cl | $CF_3$ | CCl |
| 1167 | Cl | $CF_2Cl$ | Cl | $CF_3$ | CCl |
| 1168 | Br | $CF_2Cl$ | Cl | $CF_3$ | CCl |
| 1169 | F | $CF_2Cl$ | Cl | $CF_3$ | CCl |
| 1170 | $CF_3$ | $CF_2Cl$ | Cl | $CF_3$ | CCl |
| 1171 | H | $CF_3$ | Br | $CF_3$ | CCl |
| 1172 | Cl | $CF_3$ | Br | $CF_3$ | CCl |
| 1173 | Br | $CF_3$ | Br | $CF_3$ | CCl |
| 1174 | F | $CF_3$ | Br | $CF_3$ | CCl |
| 1175 | $CF_3$ | $CF_3$ | Br | $CF_3$ | CCl |
| 1176 | H | $CF_2Cl$ | Br | $CF_3$ | CCl |
| 1177 | Cl | $CF_2Cl$ | Br | $CF_3$ | CCl |
| 1178 | Br | $CF_2Cl$ | Br | $CF_3$ | CCl |
| 1179 | F | $CF_2Cl$ | Br | $CF_3$ | CCl |
| 1180 | $CF_3$ | $CF_2Cl$ | Br | $CF_3$ | CCl |
| 1181 | H | $CF_3$ | F | $CF_3$ | CCl |
| 1182 | Cl | $CF_3$ | F | $CF_3$ | CCl |
| 1183 | Br | $CF_3$ | F | $CF_3$ | CCl |
| 1184 | F | $CF_3$ | F | $CF_3$ | CCl |
| 1185 | $CF_3$ | $CF_3$ | F | $CF_3$ | CCl |
| 1186 | H | $CF_2Cl$ | F | $CF_3$ | CCl |
| 1187 | Cl | $CF_2Cl$ | F | $CF_3$ | CCl |
| 1188 | Br | $CF_2Cl$ | F | $CF_3$ | CCl |
| 1189 | F | $CF_2Cl$ | F | $CF_3$ | CCl |
| 1190 | $CF_3$ | $CF_2Cl$ | F | $CF_3$ | CCl |
| 1191 | H | $CF_3$ | $CF_3$ | $CF_3$ | CCl |
| 1192 | Cl | $CF_3$ | $CF_3$ | $CF_3$ | CCl |
| 1193 | Br | $CF_3$ | $CF_3$ | $CF_3$ | CCl |

TABLE P-continued

| | X₃ | R³ | X₁ | R⁵ | X₂ |
|---|---|---|---|---|---|
| 1194 | F | CF₃ | CF₃ | CF₃ | CCl |
| 1195 | CF₃ | CF₃ | CF₃ | CF₃ | CCl |
| 1196 | H | CF₂Cl | CF₃ | CF₃ | CCl |
| 1197 | Cl | CF₂Cl | CF₃ | CF₃ | CCl |
| 1198 | Br | CF₂Cl | CF₃ | CF₃ | CCl |
| 1199 | F | CF₂Cl | CF₃ | CF₃ | CCl |
| 1200 | CF₃ | CF₂Cl | CF₃ | CF₃ | CCl |
| 1201 | H | CF₃ | H | F | CCl |
| 1202 | Cl | CF₃ | H | F | CCl |
| 1203 | Br | CF₃ | H | F | CCl |
| 1204 | F | CF₃ | H | F | CCl |
| 1205 | CF₃ | CF₃ | H | F | CCl |
| 1206 | H | CF₂Cl | H | F | CCl |
| 1207 | Cl | CF₂Cl | H | F | CCl |
| 1208 | Br | CF₂Cl | H | F | CCl |
| 1209 | F | CF₂Cl | H | F | CCl |
| 1210 | CF₃ | CF₂Cl | H | F | CCl |
| 1211 | H | CF₃ | Cl | F | CCl |
| 1212 | Cl | CF₃ | Cl | F | CCl |
| 1213 | Br | CF₃ | Cl | F | CCl |
| 1214 | F | CF₃ | Cl | F | CCl |
| 1215 | CF₃ | CF₃ | Cl | F | CCl |
| 1216 | H | CF₂Cl | Cl | F | CCl |
| 1217 | Cl | CF₂Cl | Cl | F | CCl |
| 1218 | Br | CF₂Cl | Cl | F | CCl |
| 1219 | F | CF₂Cl | Cl | F | CCl |
| 1220 | CF₃ | CF₂Cl | Cl | F | CCl |
| 1221 | H | CF₃ | Br | F | CCl |
| 1222 | Cl | CF₃ | Br | F | CCl |
| 1223 | Br | CF₃ | Br | F | CCl |
| 1224 | F | CF₃ | Br | F | CCl |
| 1225 | CF₃ | CF₃ | Br | F | CCl |
| 1226 | H | CF₂Cl | Br | F | CCl |
| 1227 | Cl | CF₂Cl | Br | F | CCl |
| 1228 | Br | CF₂Cl | Br | F | CCl |
| 1229 | F | CF₂Cl | Br | F | CCl |
| 1230 | CF₃ | CF₂Cl | Br | F | CCl |
| 1231 | H | CF₃ | F | F | CCl |
| 1232 | Cl | CF₃ | F | F | CCl |
| 1233 | Br | CF₃ | F | F | CCl |
| 1234 | F | CF₃ | F | F | CCl |
| 1235 | CF₃ | CF₃ | F | F | CCl |
| 1236 | H | CF₂Cl | F | F | CCl |
| 1237 | Cl | CF₂Cl | F | F | CCl |
| 1238 | Br | CF₂Cl | F | F | CCl |
| 1239 | F | CF₂Cl | F | F | CCl |
| 1240 | CF₃ | CF₂Cl | F | F | CCl |
| 1241 | H | CF₃ | CF₃ | F | CCl |
| 1242 | Cl | CF₃ | CF₃ | F | CCl |
| 1243 | Br | CF₃ | CF₃ | F | CCl |
| 1244 | F | CF₃ | CF₃ | F | CCl |
| 1245 | CF₃ | CF₃ | CF₃ | F | CCl |
| 1246 | H | CF₂Cl | CF₃ | F | CCl |
| 1247 | Cl | CF₂Cl | CF₃ | F | CCl |
| 1248 | Br | CF₂Cl | CF₃ | F | CCl |
| 1249 | F | CF₂Cl | CF₃ | F | CCl |
| 1250 | CF₃ | CF₂Cl | CF₃ | F | CCl |
| 1251 | H | CF₃ | H | Me | CF₃ |
| 1252 | Cl | CF₃ | H | Me | CF₃ |
| 1253 | Br | CF₃ | H | Me | CF₃ |
| 1254 | F | CF₃ | H | Me | CF₃ |
| 1255 | CF₃ | CF₃ | H | Me | CF₃ |
| 1256 | H | CF₂Cl | H | Me | CF₃ |
| 1257 | Cl | CF₂Cl | H | Me | CF₃ |
| 1258 | Br | CF₂Cl | H | Me | CF₃ |
| 1259 | F | CF₂Cl | H | Me | CF₃ |
| 1260 | CF₃ | CF₂Cl | H | Me | CF₃ |
| 1261 | H | CF₃ | Cl | Me | CF₃ |
| 1262 | Cl | CF₃ | Cl | Me | CF₃ |
| 1263 | Br | CF₃ | Cl | Me | CF₃ |
| 1264 | F | CF₃ | Cl | Me | CF₃ |
| 1265 | CF₃ | CF₃ | Cl | Me | CF₃ |
| 1266 | H | CF₂Cl | Cl | Me | CF₃ |
| 1267 | Cl | CF₂Cl | Cl | Me | CF₃ |
| 1268 | Br | CF₂Cl | Cl | Me | CF₃ |
| 1269 | F | CF₂Cl | Cl | Me | CF₃ |
| 1270 | CF₃ | CF₂Cl | Cl | Me | CF₃ |
| 1271 | H | CF₃ | Br | Me | CF₃ |
| 1272 | Cl | CF₃ | Br | Me | CF₃ |
| 1273 | Br | CF₃ | Br | Me | CF₃ |
| 1274 | F | CF₃ | Br | Me | CF₃ |
| 1275 | CF₃ | CF₃ | Br | Me | CF₃ |
| 1276 | H | CF₂Cl | Br | Me | CF₃ |
| 1277 | Cl | CF₂Cl | Br | Me | CF₃ |
| 1278 | Br | CF₂Cl | Br | Me | CF₃ |
| 1279 | F | CF₂Cl | Br | Me | CF₃ |
| 1280 | CF₃ | CF₂Cl | Br | Me | CF₃ |
| 1281 | H | CF₃ | F | Me | CF₃ |
| 1282 | Cl | CF₃ | F | Me | CF₃ |
| 1283 | Br | CF₃ | F | Me | CF₃ |
| 1284 | F | CF₃ | F | Me | CF₃ |
| 1285 | CF₃ | CF₃ | F | Me | CF₃ |
| 1286 | H | CF₂Cl | F | Me | CF₃ |
| 1287 | Cl | CF₂Cl | F | Me | CF₃ |
| 1288 | Br | CF₂Cl | F | Me | CF₃ |
| 1289 | F | CF₂Cl | F | Me | CF₃ |
| 1290 | CF₃ | CF₂Cl | F | Me | CF₃ |
| 1291 | H | CF₃ | CF₃ | Me | CF₃ |
| 1292 | Cl | CF₃ | CF₃ | Me | CF₃ |
| 1293 | Br | CF₃ | CF₃ | Me | CF₃ |
| 1294 | F | CF₃ | CF₃ | Me | CF₃ |
| 1295 | CF₃ | CF₃ | CF₃ | Me | CF₃ |
| 1296 | H | CF₂Cl | CF₃ | Me | CF₃ |
| 1297 | Cl | CF₂Cl | CF₃ | Me | CF₃ |
| 1298 | Br | CF₂Cl | CF₃ | Me | CF₃ |
| 1299 | F | CF₂Cl | CF₃ | Me | CF₃ |
| 1300 | CF₃ | CF₂Cl | CF₃ | Me | CF₃ |
| 1301 | H | CF₃ | H | Cl | CF₃ |
| 1302 | Cl | CF₃ | H | Cl | CF₃ |
| 1303 | Br | CF₃ | H | Cl | CF₃ |
| 1304 | F | CF₃ | H | Cl | CF₃ |
| 1305 | CF₃ | CF₃ | H | Cl | CF₃ |
| 1306 | H | CF₂Cl | H | Cl | CF₃ |
| 1307 | Cl | CF₂Cl | H | Cl | CF₃ |
| 1308 | Br | CF₂Cl | H | Cl | CF₃ |
| 1309 | F | CF₂Cl | H | Cl | CF₃ |
| 1310 | CF₃ | CF₂Cl | H | Cl | CF₃ |
| 1311 | H | CF₃ | Cl | Cl | CF₃ |
| 1312 | Cl | CF₃ | Cl | Cl | CF₃ |
| 1313 | Br | CF₃ | Cl | Cl | CF₃ |
| 1314 | F | CF₃ | Cl | Cl | CF₃ |
| 1315 | CF₃ | CF₃ | Cl | Cl | CF₃ |
| 1316 | H | CF₂Cl | Cl | Cl | CF₃ |
| 1317 | Cl | CF₂Cl | Cl | Cl | CF₃ |
| 1318 | Br | CF₂Cl | Cl | Cl | CF₃ |
| 1319 | F | CF₂Cl | Cl | Cl | CF₃ |
| 1320 | CF₃ | CF₂Cl | Cl | Cl | CF₃ |
| 1321 | H | CF₃ | Br | Cl | CF₃ |
| 1322 | Cl | CF₃ | Br | Cl | CF₃ |
| 1323 | Br | CF₃ | Br | Cl | CF₃ |
| 1324 | F | CF₃ | Br | Cl | CF₃ |
| 1325 | CF₃ | CF₃ | Br | Cl | CF₃ |
| 1326 | H | CF₂Cl | Br | Cl | CF₃ |
| 1327 | Cl | CF₂Cl | Br | Cl | CF₃ |
| 1328 | Br | CF₂Cl | Br | Cl | CF₃ |
| 1329 | F | CF₂Cl | Br | Cl | CF₃ |
| 1330 | CF₃ | CF₂Cl | Br | Cl | CF₃ |
| 1331 | H | CF₃ | F | Cl | CF₃ |
| 1332 | Cl | CF₃ | F | Cl | CF₃ |
| 1333 | Br | CF₃ | F | Cl | CF₃ |
| 1334 | F | CF₃ | F | Cl | CF₃ |
| 1335 | CF₃ | CF₃ | F | Cl | CF₃ |
| 1336 | H | CF₂Cl | F | Cl | CF₃ |
| 1337 | Cl | CF₂Cl | F | Cl | CF₃ |
| 1338 | Br | CF₂Cl | F | Cl | CF₃ |
| 1339 | F | CF₂Cl | F | Cl | CF₃ |
| 1340 | CF₃ | CF₂Cl | F | Cl | CF₃ |
| 1341 | H | CF₃ | CF₃ | Cl | CF₃ |
| 1342 | Cl | CF₃ | CF₃ | Cl | CF₃ |
| 1343 | Br | CF₃ | CF₃ | Cl | CF₃ |
| 1344 | F | CF₃ | CF₃ | Cl | CF₃ |
| 1345 | CF₃ | CF₃ | CF₃ | Cl | CF₃ |
| 1346 | H | CF₂Cl | CF₃ | Cl | CF₃ |
| 1347 | Cl | CF₂Cl | CF₃ | Cl | CF₃ |
| 1348 | Br | CF₂Cl | CF₃ | Cl | CF₃ |
| 1349 | F | CF₂Cl | CF₃ | Cl | CF₃ |

TABLE P-continued

| | $X_3$ | $R^3$ | $X_1$ | $R^5$ | $X_2$ |
|---|---|---|---|---|---|
| 1350 | $CF_3$ | $CF_2Cl$ | $CF_3$ | Cl | $CF_3$ |
| 1351 | H | $CF_3$ | H | Br | $CF_3$ |
| 1352 | Cl | $CF_3$ | H | Br | $CF_3$ |
| 1353 | Br | $CF_3$ | H | Br | $CF_3$ |
| 1354 | F | $CF_3$ | H | Br | $CF_3$ |
| 1355 | $CF_3$ | $CF_3$ | H | Br | $CF_3$ |
| 1356 | H | $CF_2Cl$ | H | Br | $CF_3$ |
| 1357 | Cl | $CF_2Cl$ | H | Br | $CF_3$ |
| 1358 | Br | $CF_2Cl$ | H | Br | $CF_3$ |
| 1359 | F | $CF_2Cl$ | H | Br | $CF_3$ |
| 1360 | $CF_3$ | $CF_2Cl$ | H | Br | $CF_3$ |
| 1361 | H | $CF_3$ | Cl | Br | $CF_3$ |
| 1362 | Cl | $CF_3$ | Cl | Br | $CF_3$ |
| 1363 | Br | $CF_3$ | Cl | Br | $CF_3$ |
| 1364 | F | $CF_3$ | Cl | Br | $CF_3$ |
| 1365 | $CF_3$ | $CF_3$ | Cl | Br | $CF_3$ |
| 1366 | H | $CF_2Cl$ | Cl | Br | $CF_3$ |
| 1367 | Cl | $CF_2Cl$ | Cl | Br | $CF_3$ |
| 1368 | Br | $CF_2Cl$ | Cl | Br | $CF_3$ |
| 1369 | F | $CF_2Cl$ | Cl | Br | $CF_3$ |
| 1370 | $CF_3$ | $CF_2Cl$ | Cl | Br | $CF_3$ |
| 1371 | H | $CF_3$ | Br | Br | $CF_3$ |
| 1372 | Cl | $CF_3$ | Br | Br | $CF_3$ |
| 1373 | Br | $CF_3$ | Br | Br | $CF_3$ |
| 1374 | F | $CF_3$ | Br | Br | $CF_3$ |
| 1375 | $CF_3$ | $CF_3$ | Br | Br | $CF_3$ |
| 1376 | H | $CF_2Cl$ | Br | Br | $CF_3$ |
| 1377 | Cl | $CF_2Cl$ | Br | Br | $CF_3$ |
| 1378 | Br | $CF_2Cl$ | Br | Br | $CF_3$ |
| 1379 | F | $CF_2Cl$ | Br | Br | $CF_3$ |
| 1380 | $CF_3$ | $CF_2Cl$ | Br | Br | $CF_3$ |
| 1381 | H | $CF_3$ | F | Br | $CF_3$ |
| 1382 | Cl | $CF_3$ | F | Br | $CF_3$ |
| 1383 | Br | $CF_3$ | F | Br | $CF_3$ |
| 1384 | F | $CF_3$ | F | Br | $CF_3$ |
| 1385 | $CF_3$ | $CF_3$ | F | Br | $CF_3$ |
| 1386 | H | $CF_2Cl$ | F | Br | $CF_3$ |
| 1387 | Cl | $CF_2Cl$ | F | Br | $CF_3$ |
| 1388 | Br | $CF_2Cl$ | F | Br | $CF_3$ |
| 1389 | F | $CF_2Cl$ | F | Br | $CF_3$ |
| 1390 | $CF_3$ | $CF_2Cl$ | F | Br | $CF_3$ |
| 1391 | H | $CF_3$ | $CF_3$ | Br | $CF_3$ |
| 1392 | Cl | $CF_3$ | $CF_3$ | Br | $CF_3$ |
| 1393 | Br | $CF_3$ | $CF_3$ | Br | $CF_3$ |
| 1394 | F | $CF_3$ | $CF_3$ | Br | $CF_3$ |
| 1395 | $CF_3$ | $CF_3$ | $CF_3$ | Br | $CF_3$ |
| 1396 | H | $CF_2Cl$ | $CF_3$ | Br | $CF_3$ |
| 1397 | Cl | $CF_2Cl$ | $CF_3$ | Br | $CF_3$ |
| 1398 | Br | $CF_2Cl$ | $CF_3$ | Br | $CF_3$ |
| 1399 | F | $CF_2Cl$ | $CF_3$ | Br | $CF_3$ |
| 1400 | $CF_3$ | $CF_2Cl$ | $CF_3$ | Br | $CF_3$ |
| 1401 | H | $CF_3$ | H | $CF_3$ | $CF_3$ |
| 1402 | Cl | $CF_3$ | H | $CF_3$ | $CF_3$ |
| 1403 | Br | $CF_3$ | H | $CF_3$ | $CF_3$ |
| 1404 | F | $CF_3$ | H | $CF_3$ | $CF_3$ |
| 1405 | $CF_3$ | $CF_3$ | H | $CF_3$ | $CF_3$ |
| 1406 | H | $CF_2Cl$ | H | $CF_3$ | $CF_3$ |
| 1407 | Cl | $CF_2Cl$ | H | $CF_3$ | $CF_3$ |
| 1408 | Br | $CF_2Cl$ | H | $CF_3$ | $CF_3$ |
| 1409 | F | $CF_2Cl$ | H | $CF_3$ | $CF_3$ |
| 1410 | $CF_3$ | $CF_2Cl$ | H | $CF_3$ | $CF_3$ |
| 1411 | H | $CF_3$ | Cl | $CF_3$ | $CF_3$ |
| 1412 | Cl | $CF_3$ | Cl | $CF_3$ | $CF_3$ |
| 1413 | Br | $CF_3$ | Cl | $CF_3$ | $CF_3$ |
| 1414 | F | $CF_3$ | Cl | $CF_3$ | $CF_3$ |
| 1415 | $CF_3$ | $CF_3$ | Cl | $CF_3$ | $CF_3$ |
| 1416 | H | $CF_2Cl$ | Cl | $CF_3$ | $CF_3$ |
| 1417 | Cl | $CF_2Cl$ | Cl | $CF_3$ | $CF_3$ |
| 1418 | Br | $CF_2Cl$ | Cl | $CF_3$ | $CF_3$ |
| 1419 | F | $CF_2Cl$ | Cl | $CF_3$ | $CF_3$ |
| 1420 | $CF_3$ | $CF_2Cl$ | Cl | $CF_3$ | $CF_3$ |
| 1421 | H | $CF_3$ | Br | $CF_3$ | $CF_3$ |
| 1422 | Cl | $CF_3$ | Br | $CF_3$ | $CF_3$ |
| 1423 | Br | $CF_3$ | Br | $CF_3$ | $CF_3$ |
| 1424 | F | $CF_3$ | Br | $CF_3$ | $CF_3$ |
| 1425 | $CF_3$ | $CF_3$ | Br | $CF_3$ | $CF_3$ |
| 1426 | H | $CF_2Cl$ | Br | $CF_3$ | $CF_3$ |
| 1427 | Cl | $CF_2Cl$ | Br | $CF_3$ | $CF_3$ |
| 1428 | Br | $CF_2Cl$ | Br | $CF_3$ | $CF_3$ |
| 1429 | F | $CF_2Cl$ | Br | $CF_3$ | $CF_3$ |
| 1430 | $CF_3$ | $CF_2Cl$ | Br | $CF_3$ | $CF_3$ |
| 1431 | H | $CF_3$ | F | $CF_3$ | $CF_3$ |
| 1432 | Cl | $CF_3$ | F | $CF_3$ | $CF_3$ |
| 1433 | Br | $CF_3$ | F | $CF_3$ | $CF_3$ |
| 1434 | F | $CF_3$ | F | $CF_3$ | $CF_3$ |
| 1435 | $CF_3$ | $CF_3$ | F | $CF_3$ | $CF_3$ |
| 1436 | H | $CF_2Cl$ | F | $CF_3$ | $CF_3$ |
| 1437 | Cl | $CF_2Cl$ | F | $CF_3$ | $CF_3$ |
| 1438 | Br | $CF_2Cl$ | F | $CF_3$ | $CF_3$ |
| 1439 | F | $CF_2Cl$ | F | $CF_3$ | $CF_3$ |
| 1440 | $CF_3$ | $CF_2Cl$ | F | $CF_3$ | $CF_3$ |
| 1441 | H | $CF_3$ | $CF_3$ | $CF_3$ | $CF_3$ |
| 1442 | Cl | $CF_3$ | $CF_3$ | $CF_3$ | $CF_3$ |
| 1443 | Br | $CF_3$ | $CF_3$ | $CF_3$ | $CF_3$ |
| 1444 | F | $CF_3$ | $CF_3$ | $CF_3$ | $CF_3$ |
| 1445 | $CF_3$ | $CF_3$ | $CF_3$ | $CF_3$ | $CF_3$ |
| 1446 | H | $CF_2Cl$ | $CF_3$ | $CF_3$ | $CF_3$ |
| 1447 | Cl | $CF_2Cl$ | $CF_3$ | $CF_3$ | $CF_3$ |
| 1458 | Br | $CF_2Cl$ | $CF_3$ | $CF_3$ | $CF_3$ |
| 1449 | F | $CF_2Cl$ | $CF_3$ | $CF_3$ | $CF_3$ |
| 1450 | $CF_3$ | $CF_2Cl$ | $CF_3$ | $CF_3$ | $CF_3$ |
| 1451 | H | $CF_3$ | H | F | $CF_3$ |
| 1452 | Cl | $CF_3$ | H | F | $CF_3$ |
| 1453 | Br | $CF_3$ | H | F | $CF_3$ |
| 1454 | F | $CF_3$ | H | F | $CF_3$ |
| 1455 | $CF_3$ | $CF_3$ | H | F | $CF_3$ |
| 1456 | H | $CF_2Cl$ | H | F | $CF_3$ |
| 1457 | Cl | $CF_2Cl$ | H | F | $CF_3$ |
| 1458 | Br | $CF_2Cl$ | H | F | $CF_3$ |
| 1459 | F | $CF_2Cl$ | H | F | $CF_3$ |
| 1460 | $CF_3$ | $CF_2Cl$ | H | F | $CF_3$ |
| 1461 | H | $CF_3$ | Cl | F | $CF_3$ |
| 1462 | Cl | $CF_3$ | Cl | F | $CF_3$ |
| 1463 | Br | $CF_3$ | Cl | F | $CF_3$ |
| 1464 | F | $CF_3$ | Cl | F | $CF_3$ |
| 1465 | $CF_3$ | $CF_3$ | Cl | F | $CF_3$ |
| 1466 | H | $CF_2Cl$ | Cl | F | $CF_3$ |
| 1467 | Cl | $CF_2Cl$ | Cl | F | $CF_3$ |
| 1468 | Br | $CF_2Cl$ | Cl | F | $CF_3$ |
| 1469 | F | $CF_2Cl$ | Cl | F | $CF_3$ |
| 1470 | $CF_3$ | $CF_2Cl$ | Cl | F | $CF_3$ |
| 1471 | H | $CF_3$ | Br | F | $CF_3$ |
| 1472 | Cl | $CF_3$ | Br | F | $CF_3$ |
| 1473 | Br | $CF_3$ | Br | F | $CF_3$ |
| 1474 | F | $CF_3$ | Br | F | $CF_3$ |
| 1475 | $CF_3$ | $CF_3$ | Br | F | $CF_3$ |
| 1476 | H | $CF_2Cl$ | Br | F | $CF_3$ |
| 1477 | Cl | $CF_2Cl$ | Br | F | $CF_3$ |
| 1478 | Br | $CF_2Cl$ | Br | F | $CF_3$ |
| 1479 | F | $CF_2Cl$ | Br | F | $CF_3$ |
| 1480 | $CF_3$ | $CF_2Cl$ | Br | F | $CF_3$ |
| 1481 | H | $CF_3$ | F | F | $CF_3$ |
| 1482 | Cl | $CF_3$ | F | F | $CF_3$ |
| 1483 | Br | $CF_3$ | F | F | $CF_3$ |
| 1484 | F | $CF_3$ | F | F | $CF_3$ |
| 1485 | $CF_3$ | $CF_3$ | F | F | $CF_3$ |
| 1486 | H | $CF_2Cl$ | F | F | $CF_3$ |
| 1487 | Cl | $CF_2Cl$ | F | F | $CF_3$ |
| 1488 | Br | $CF_2Cl$ | F | F | $CF_3$ |
| 1489 | F | $CF_2Cl$ | F | F | $CF_3$ |
| 1490 | $CF_3$ | $CF_2Cl$ | F | F | $CF_3$ |
| 1491 | H | $CF_3$ | $CF_3$ | F | $CF_3$ |
| 1492 | Cl | $CF_3$ | $CF_3$ | F | $CF_3$ |
| 1493 | Br | $CF_3$ | $CF_3$ | F | $CF_3$ |
| 1494 | F | $CF_3$ | $CF_3$ | F | $CF_3$ |
| 1495 | $CF_3$ | $CF_3$ | $CF_3$ | F | $CF_3$ |
| 1496 | H | $CF_2Cl$ | $CF_3$ | F | $CF_3$ |
| 1497 | Cl | $CF_2Cl$ | $CF_3$ | F | $CF_3$ |
| 1498 | Br | $CF_2Cl$ | $CF_3$ | F | $CF_3$ |
| 1499 | F | $CF_2Cl$ | $CF_3$ | F | $CF_3$ |
| 1500 | $CF_3$ | $CF_2Cl$ | $CF_3$ | F | $CF_3$ |

Table 1

Table 1 provides 1500 compounds of formula (Ia) wherein $R^1$ is hydrogen, $R^2$ is Me, and $X_2$, $X_3$, $R^3$, $X_1$, $R^5$ are as defined in Table P.

Table 2

Table 2 provides 1500 compounds of formula (Ia) wherein $R^1$ is hydrogen, $R^2$ is Et, and $X_2$, $X_3$, $R^3$, $X_1$, $R^5$ are as defined in Table P.

Table 3

Table 3 provides 1500 compounds of formula (Ia) wherein $R^1$ is hydrogen, $R^2$ is Pr, and $X_2$, $X_3$, $R^3$, $X_1$, $R^5$ are as defined in Table P.

Table 4

Table 4 provides 1500 compounds of formula (Ia) wherein $R^1$ is hydrogen, $R^2$ is $N(Et)_2$, and $X_2$, $X_3$, $R^3$, $X_1$, $R^5$ are as defined in Table P.

Table 5

Table 5 provides 1500 compounds of formula (Ia) wherein $R^1$ is hydrogen, $R^2$ is iPr, and $X_2$, $X_3$, $R^3$, $X_1$, $R^5$ are as defined in Table P.

Table 6

Table 6 provides 1500 compounds of formula (Ia) wherein $R^1$ is hydrogen, $R^2$ is $N(Me)_2$, and $X_2$, $X_3$, $R^3$, $X_1$, $R^5$ are as defined in Table P.

Table 7

Table 7 provides 1500 compounds of formula (Ia) wherein $R^1$ is hydrogen, $R^2$ is cBu, and $X_2$, $X_3$, $R^3$, $X_1$, $R^5$ are as defined in Table P.

Table 8

Table 8 provides 1500 compounds of formula (Ia) wherein $R^1$ is hydrogen, $R^2$ is NHEt, and $X_2$, $X_3$, $R^3$, $X_1$, $R^5$ are as defined in Table P.

Table 9

Table 9 provides 1500 compounds of formula (Ia) wherein $R^1$ is hydrogen, $R^2$ is $CH_2CF_3$, and $X_2$, $X_3$, $R^3$, $X_1$, $R^5$ are as defined in Table P.

Table 10

Table 10 provides 1500 compounds of formula (Ia) wherein $R^1$ is hydrogen, $R^2$ is NHMe, and $X_2$, $X_3$, $R^3$, $X_1$, $R^5$ are as defined in Table P.

Table 11

Table 11 provides 1500 compounds of formula (Ia) wherein $R^1$ is hydrogen, $R^2$ is NMeEt, and $X_2$, $X_3$, $R^3$, $X_1$, $R^5$ are as defined in Table P.

Table 12

Table 12 provides 1500 compounds of formula (Ia) wherein $R^1$ is hydrogen, $R^2$ is cPr, and $X_2$, $X_3$, $R^3$, $X_1$, $R^5$ are as defined in Table P.

Table 13

Table 13 provides 1500 compounds of formula (Ia) wherein $R^1$ is hydrogen, $R^2$ is $CH_2Cl$, and $X_2$, $X_3$, $R^3$, $X_1$, $R^5$ are as defined in Table P.

Table 14

Table 14 provides 1500 compounds of formula (Ia) wherein $R^1$ is hydrogen, $R^2$ is $CH_2F$, and $X_2$, $X_3$, $R^3$, $X_1$, $R^5$ are as defined in Table P.

Table 15

Table 15 provides 1500 compounds of formula (Ia) wherein $R^1$ is hydrogen, $R^2$ is $CHF_2$, and $X_2$, $X_3$, $R^3$, $X_1$, $R^5$ are as defined in Table P.

Table 16

Table 16 provides 1500 compounds of formula (Ia) wherein $R^1$ is hydrogen, $R^2$ is F, and $X_2$, $X_3$, $R^3$, $X_1$, $R^5$ are as defined in Table P.

Table 17

Table 17 provides 1500 compounds of formula (Ia) wherein $R^1$ is $CH_2CN$, $R^2$ is Me, and $X_2$, $X_3$, $R^3$, $X_1$, $R^5$ are as defined in Table P.

Table 18

Table 18 provides 1500 compounds of formula (Ia) wherein $R^1$ is $CH_2CN$, $R^2$ is Et, and $X_2$, $X_3$, $R^3$, $X_1$, $R^5$ are as defined in Table P.

Table 19

Table 19 provides 1500 compounds of formula (Ia) wherein $R^1$ is $CH_2CN$, $R^2$ is Pr, and $X_2$, $X_3$, $R^3$, $X_1$, $R^5$ are as defined in Table P.

Table 20

Table 20 provides 1500 compounds of formula (Ia) wherein $R^1$ is $CH_2CN$, $R^2$ is $N(Et)_2$, and $X_2$, $X_3$, $R^3$, $X_1$, $R^5$ are as defined in Table P.

Table 21

Table 21 provides 1500 compounds of formula (Ia) wherein $R^1$ is $CH_2CN$, $R^2$ is iPr, and $X_2$, $X_3$, $R^3$, $X_1$, $R^5$ are as defined in Table P.

Table 22

Table 22 provides 1500 compounds of formula (Ia) wherein $R^1$ is $CH_2CN$, $R^2$ is $N(Me)_2$, and $X_2$, $X_3$, $R^3$, $X_1$, $R^5$ are as defined in Table P.

Table 23

Table 23 provides 1500 compounds of formula (Ia) wherein $R^1$ is $CH_2CN$, $R^2$ is cBu, and $X_2$, $X_3$, $R^3$, $X_1$, $R^5$ are as defined in Table P.

Table 24

Table 24 provides 1500 compounds of formula (Ia) wherein $R^1$ is $CH_2CN$, $R^2$ is NHEt, and $X_2$, $X_3$, $R^3$, $X_1$, $R^5$ are as defined in Table P.

Table 25

Table 25 provides 1500 compounds of formula (Ia) wherein $R^1$ is $CH_2CN$, $R^2$ is $CH_2CF_3$, and $X_2$, $X_3$, $R^3$, $X_1$, $R^5$ are as defined in Table P.

Table 26

Table 26 provides 1500 compounds of formula (Ia) wherein $R^1$ is $CH_2CN$, $R^2$ is NHMe, and $X_2$, $X_3$, $R^3$, $X_1$, $R^5$ are as defined in Table P.

Table 27

Table 27 provides 1500 compounds of formula (Ia) wherein $R^1$ is $CH_2CN$, $R^2$ is NMeEt, and $X_2$, $X_3$, $R^3$, $X_1$, $R^5$ are as defined in Table P.

Table 28

Table 28 provides 1500 compounds of formula (Ia) wherein $R^1$ is $CH_2CN$, $R^2$ is cPr, and $X_2$, $X_3$, $R^3$, $X_1$, $R^5$ are as defined in Table P.

Table 29

Table 29 provides 1500 compounds of formula (Ia) wherein $R^1$ is $CH_2CN$, $R^2$ is $CH_2Cl$, and $X_2$, $X_3$, $R^3$, $X_1$, $R^5$ are as defined in Table P.

Table 30

Table 30 provides 1500 compounds of formula (Ia) wherein $R^1$ is $CH_2CN$, $R^2$ is $CH_2F$, and $X_2$, $X_3$, $R^3$, $X_1$, $R^5$ are as defined in Table P.

Table 31

Table 31 provides 1500 compounds of formula (Ia) wherein $R^1$ is $CH_2CN$, $R^2$ is $CHF_2$, and $X_2$, $X_3$, $R^3$, $X_1$, $R^5$ are as defined in Table P.

Table 32

Table 32 provides 1500 compounds of formula (Ia) wherein $R^1$ is $CH_2CN$, $R^2$ is F, and $X_2$, $X_3$, $R^3$, $X_1$, $R^5$ are as defined in Table P.

Table 33

Table 33 provides 1500 compounds of formula (Ia) wherein $R^1$ is $CH_2OCH_3$, $R^2$ is Me, and $X_2$, $X_3$, $R^3$, $X_1$, $R^5$ are as defined in Table P.

Table 34

Table 34 provides 1500 compounds of formula (Ia) wherein $R^1$ is $CH_2OCH_3$, $R^2$ is Et, and $X_2$, $X_3$, $R^3$, $X_1$, $R^5$ are as defined in Table P.

Table 35

Table 35 provides 1500 compounds of formula (Ia) wherein $R^1$ is $CH_2OCH_3$, $R^2$ is Pr, and $X_2$, $X_3$, $R^3$, $X_1$, $R^5$ are as defined in Table P.

Table 36

Table 36 provides 1500 compounds of formula (Ia) wherein $R^1$ is $CH_2OCH_3$, $R^2$ is $N(Et)_2$, and $X_2$, $X_3$, $R^3$, $X_1$, $R^5$ are as defined in Table P.

Table 37

Table 37 provides 1500 compounds of formula (Ia) wherein $R^1$ is $CH_2OCH_3$, $R^2$ is iPr, and $X_2$, $X_3$, $R^3$, $X_1$, $R^5$ are as defined in Table P.

Table 38

Table 38 provides 1500 compounds of formula (Ia) wherein $R^1$ is $CH_2OCH_3$, $R^2$ is $N(Me)_2$, and $X_2$, $X_3$, $R^3$, $X_1$, $R^5$ are as defined in Table P.

Table 39

Table 39 provides 1500 compounds of formula (Ia) wherein $R^1$ is $CH_2OCH_3$, $R^2$ is cBu, and $X_2$, $X_3$, $R^3$, $X_1$, $R^5$ are as defined in Table P.

Table 40

Table 40 provides 1500 compounds of formula (Ia) wherein $R^1$ is $CH_2OCH_3$, $R^2$ is NHEt, and $X_2$, $X_3$, $R^3$, $X_1$, $R^5$ are as defined in Table P.

Table 41

Table 41 provides 1500 compounds of formula (Ia) wherein $R^1$ is $CH_2OCH_3$, $R^2$ is $CH_2CF_3$, and $X_2$, $X_3$, $R^3$, $X_1$, $R^5$ are as defined in Table P.

Table 42

Table 42 provides 1500 compounds of formula (Ia) wherein $R^1$ is $CH_2OCH_3$, $R^2$ is NHMe, and $X_2$, $X_3$, $R^3$, $X_1$, $R^5$ are as defined in Table P.

Table 43

Table 43 provides 1500 compounds of formula (Ia) wherein $R^1$ is $CH_2OCH_3$, $R^2$ is NMeEt, and $X_2$, $X_3$, $R^3$, $X_1$, $R^5$ are as defined in Table P.

Table 44

Table 44 provides 1500 compounds of formula (Ia) wherein $R^1$ is $CH_2OCH_3$, $R^2$ is cPr, and $X_2$, $X_3$, $R^3$, $X_1$, $R^5$ are as defined in Table P.

Table 45

Table 45 provides 1500 compounds of formula (Ia) wherein $R^1$ is $CH_2OCH_3$, $R^2$ is $CH_2Cl$, and $X_2$, $X_3$, $R^3$, $X_1$, $R^5$ are as defined in Table P.

Table 46

Table 46 provides 1500 compounds of formula (Ia) wherein $R^1$ is $CH_2OCH_3$, $R^2$ is $CH_2F$, and $X_2$, $X_3$, $R^3$, $X_1$, $R^5$ are as defined in Table P.

Table 47

Table 47 provides 1500 compounds of formula (Ia) wherein $R^1$ is $CH_2OCH_3$, $R^2$ is $CHF_2$, and $X_2$, $X_3$, $R^3$, $X_1$, $R^5$ are as defined in Table P.

Table 48

Table 48 provides 1500 compounds of formula (Ia) wherein $R^1$ is $CH_2OCH_3$, $R^2$ is F, and $X_2$, $X_3$, $R^3$, $X_1$, $R^5$ are as defined in Table P.

Table 49

Table 49 provides 1500 compounds of formula (Ia) wherein $R^1$ is $CH_2OCH_2CH_3$, $R^2$ is Me, and $X_2$, $X_3$, $R^3$, $X_1$, $R^5$ are as defined in Table P.

Table 50

Table 50 provides 1500 compounds of formula (Ia) wherein $R^1$ is $CH_2OCH_2CH_3$, $R^2$ is Et, and $X_2$, $X_3$, $R^3$, $X_1$, $R^5$ are as defined in Table P.

Table 51

Table 51 provides 1500 compounds of formula (Ia) wherein $R^1$ is $CH_2OCH_2CH_3$, $R^2$ is Pr, and $X_2$, $X_3$, $R^3$, $X_1$, $R^5$ are as defined in Table P.

Table 52

Table 52 provides 1500 compounds of formula (Ia) wherein $R^1$ is $CH_2OCH_2CH_3$, $R^2$ is $N(Et)_2$, and $X_2$, $X_3$, $R^3$, $X_1$, $R^5$ are as defined in Table P.

Table 53

Table 53 provides 1500 compounds of formula (Ia) wherein $R^1$ is $CH_2OCH_2CH_3$, $R^2$ is iPr, and $X_2$, $X_3$, $R^3$, $X_1$, $R^5$ are as defined in Table P.

Table 54

Table 54 provides 1500 compounds of formula (Ia) wherein $R^1$ is $CH_2OCH_2CH_3$, $R^2$ is $N(Me)_2$, and $X_2$, $X_3$, $R^3$, $X_1$, $R^5$ are as defined in Table P.

Table 55

Table 55 provides 1500 compounds of formula (Ia) wherein $R^1$ is $CH_2OCH_2CH_3$, $R^2$ is cBu, and $X_2$, $X_3$, $R^3$, $X_1$, $R^5$ are as defined in Table P.

Table 56

Table 56 provides 1500 compounds of formula (Ia) wherein $R^1$ is $CH_2OCH_2CH_3$, $R^2$ is NHEt, and $X_2$, $X_3$, $R^3$, $X_1$, $R^5$ are as defined in Table P.

Table 57

Table 57 provides 1500 compounds of formula (Ia) wherein $R^1$ is $CH_2OCH_2CH_3$, $R^2$ is $CH_2CF_3$, and $X_2$, $X_3$, $R^3$, $X_1$, $R^5$ are as defined in Table P.

Table 58

Table 58 provides 1500 compounds of formula (Ia) wherein $R^1$ is $CH_2OCH_2CH_3$, $R^2$ is NHMe, and $X_2$, $X_3$, $R^3$, $X_1$, $R^5$ are as defined in Table P.

Table 59

Table 59 provides 1500 compounds of formula (Ia) wherein $R^1$ is $CH_2OCH_2CH_3$, $R^2$ is NMeEt, and $X_2$, $X_3$, $R^3$, $X_1$, $R^5$ are as defined in Table P.

Table 60

Table 60 provides 1500 compounds of formula (Ia) wherein $R^1$ is $CH_2OCH_2CH_3$, $R^2$ is cPr, and $X_2$, $X_3$, $R^3$, $X_1$, $R^5$ are as defined in Table P.

Table 61

Table 61 provides 1500 compounds of formula (Ia) wherein $R^1$ is $CH_2OCH_2CH_3$, $R^2$ is $CH_2Cl$, and $X_2$, $X_3$, $R^3$, $X_1$, $R^5$ are as defined in Table P.

Table 62

Table 62 provides 1500 compounds of formula (Ia) wherein $R^1$ is $CH_2OCH_2CH_3$, $R^2$ is $CH_2F$, and $X_2$, $X_3$, $R^3$, $X_1$, $R^5$ are as defined in Table P.

Table 63

Table 63 provides 1500 compounds of formula (Ia) wherein $R^1$ is $CH_2OCH_2CH_3$, $R^2$ is $CHF_2$, and $X_2$, $X_3$, $R^3$, $X_1$, $R^5$ are as defined in Table P.

Table 64

Table 64 provides 1500 compounds of formula (Ia) wherein $R^1$ is $CH_2OCH_2CH_3$, $R^2$ is F, and $X_2$, $X_3$, $R^3$, $X_1$, $R^5$ are as defined in Table P.

Table 65

Table 65 provides 1500 compounds of formula (Ia) wherein $R^1$ is $C(O)OCH_3$, $R^2$ is Me, and $X_2$, $X_3$, $R^3$, $X_1$, $R^5$ are as defined in Table P.

Table 66

Table 66 provides 1500 compounds of formula (Ia) wherein $R^1$ is $C(O)OCH_3$, $R^2$ is Et, and $X_2$, $X_3$, $R^3$, $X_1$, $R^5$ are as defined in Table P.

Table 67

Table 67 provides 1500 compounds of formula (Ia) wherein $R^1$ is $C(O)OCH_3$, $R^2$ is Pr, and $X_2$, $X_3$, $R^3$, $X_1$, $R^5$ are as defined in Table P.

Table 68

Table 68 provides 1500 compounds of formula (Ia) wherein $R^1$ is $C(O)OCH_3$, $R^2$ is $N(Et)_2$, and $X_2$, $X_3$, $R^3$, $X_1$, $R^5$ are as defined in Table P.

Table 69

Table 69 provides 1500 compounds of formula (Ia) wherein $R^1$ is $C(O)OCH_3$, $R^2$ is iPr, and $X_2$, $X_3$, $R^3$, $X_1$, $R^5$ are as defined in Table P.

Table 70

Table 70 provides 1500 compounds of formula (Ia) wherein $R^1$ is $C(O)OCH_3$, $R^2$ is $N(Me)_2$, and $X_2$, $X_3$, $R^3$, $X_1$, $R^5$ are as defined in Table P.

Table 71

Table 71 provides 1500 compounds of formula (Ia) wherein $R^1$ is $C(O)OCH_3$, $R^2$ is cBu, and $X_2$, $X_3$, $R^3$, $X_1$, $R^5$ are as defined in Table P.

Table 72

Table 72 provides 1500 compounds of formula (Ia) wherein $R^1$ is $C(O)OCH_3$, $R^2$ is NHEt, and $X_2$, $X_3$, $R^3$, $X_1$, $R^5$ are as defined in Table P.

Table 73

Table 73 provides 1500 compounds of formula (Ia) wherein $R^1$ is $C(O)OCH_3$, $R^2$ is $CH_2CF_3$, and $X_2$, $X_3$, $R^3$, $X_1$, $R^5$ are as defined in Table P.

Table 74

Table 74 provides 1500 compounds of formula (Ia) wherein $R^1$ is $C(O)OCH_3$, $R^2$ is NHMe, and $X_2$, $X_3$, $R^3$, $X_1$, $R^5$ are as defined in Table P.

Table 75

Table 75 provides 1500 compounds of formula (Ia) wherein $R^1$ is $C(O)OCH_3$, $R^2$ is NMeEt, and $X_2$, $X_3$, $R^3$, $X_1$, $R^5$ are as defined in Table P.

Table 76

Table 76 provides 1500 compounds of formula (Ia) wherein $R^1$ is $C(O)OCH_3$, $R^2$ is cPr, and $X_2$, $X_3$, $R^3$, $X_1$, $R^5$ are as defined in Table P.

Table 77

Table 77 provides 1500 compounds of formula (Ia) wherein $R^1$ is $C(O)OCH_3$, $R^2$ is $CH_2Cl$, and $X_2$, $X_3$, $R^3$, $X_1$, $R^5$ are as defined in Table P.

Table 78

Table 78 provides 1500 compounds of formula (Ia) wherein $R^1$ is $C(O)OCH_3$, $R^2$ is $CH_2F$, and $X_2$, $X_3$, $R^3$, $X_1$, $R^5$ are as defined in Table P.

Table 79

Table 79 provides 1500 compounds of formula (Ia) wherein $R^1$ is $C(O)OCH_3$, $R^2$ is $CHF_2$, and $X_2$, $X_3$, $R^3$, $X_1$, $R^5$ are as defined in Table P.

Table 80

Table 80 provides 1500 compounds of formula (Ia) wherein $R^1$ is $C(O)OCH_3$, $R^2$ is F, and $X_2$, $X_3$, $R^3$, $X_1$, $R^5$ are as defined in Table P.

Table 81

Table 81 provides 1500 compounds of formula (Ia) wherein $R^1$ is $C(O)OCH_2CH_3$, $R^2$ is Me, and $X_2$, $X_3$, $R^3$, $X_1$, $R^5$ are as defined in Table P.

Table 82

Table 82 provides 1500 compounds of formula (Ia) wherein $R^1$ is $C(O)OCH_2CH_3$, $R^2$ is Et, and $X_2$, $X_3$, $R^3$, $X_1$, $R^5$ are as defined in Table P.

Table 83

Table 83 provides 1500 compounds of formula (Ia) wherein $R^1$ is $C(O)OCH_2CH_3$, $R^2$ is Pr, and $X_2$, $X_3$, $R^3$, $X_1$, $R^5$ are as defined in Table P.

Table 84

Table 84 provides 1500 compounds of formula (Ia) wherein $R^1$ is $C(O)OCH_2CH_3$, $R^2$ is $N(Et)_2$, and $X_2$, $X_3$, $R^3$, $X_1$, $R^5$ are as defined in Table P.

Table 85

Table 85 provides 1500 compounds of formula (Ia) wherein $R^1$ is $C(O)OCH_2CH_3$, $R^2$ is iPr, and $X_2$, $X_3$, $R^3$, $X_1$, $R^5$ are as defined in Table P.

Table 86

Table 86 provides 1500 compounds of formula (Ia) wherein $R^1$ is $C(O)OCH_2CH_3$, $R^2$ is $N(Me)_2$, and $X_2$, $X_3$, $R^3$, $X_1$, $R^5$ are as defined in Table P.

Table 87

Table 87 provides 1500 compounds of formula (Ia) wherein $R^1$ is $C(O)OCH_2CH_3$, $R^2$ is cBu, and $X_2$, $X_3$, $R^3$, $X_1$, $R^5$ are as defined in Table P.

Table 88

Table 88 provides 1500 compounds of formula (Ia) wherein $R^1$ is $C(O)OCH_2CH_3$, $R^2$ is NHEt, and $X_2$, $X_3$, $R^3$, $X_1$, $R^5$ are as defined in Table P.

Table 89

Table 89 provides 1500 compounds of formula (Ia) wherein $R^1$ is $C(O)OCH_2CH_3$, $R^2$ is $CH_2CF_3$, and $X_2$, $X_3$, $R^3$, $X_1$, $R^5$ are as defined in Table P.

Table 90

Table 90 provides 1500 compounds of formula (Ia) wherein $R^1$ is $C(O)OCH_2CH_3$, $R^2$ is NHMe, and $X_2$, $X_3$, $R^3$, $X_1$, $R^5$ are as defined in Table P.

Table 91

Table 91 provides 1500 compounds of formula (Ia) wherein $R^1$ is $C(O)OCH_2CH_3$, $R^2$ is NMeEt, and $X_2$, $X_3$, $R^3$, $X_1$, $R^5$ are as defined in Table P.

Table 92

Table 92 provides 1500 compounds of formula (Ia) wherein $R^1$ is $C(O)OCH_2CH_3$, $R^2$ is cPr, and $X_2$, $X_3$, $R^3$, $X_1$, $R^5$ are as defined in Table P.

Table 93

Table 93 provides 1500 compounds of formula (Ia) wherein $R^1$ is $C(O)OCH_2CH_3$, $R^2$ is $CH_2Cl$, and $X_2$, $X_3$, $R^3$, $X_1$, $R^5$ are as defined in Table P.

Table 94

Table 94 provides 1500 compounds of formula (Ia) wherein $R^1$ is $C(O)OCH_2CH_3$, $R^2$ is $CH_2F$, and $X_2$, $X_3$, $R^3$, $X_1$, $R^5$ are as defined in Table P.

Table 95

Table 95 provides 1500 compounds of formula (Ia) wherein $R^1$ is $C(O)OCH_2CH_3$, $R^2$ is $CHF_2$, and $X_2$, $X_3$, $R^3$, $X_1$, $R^5$ are as defined in Table P.

Table 96

Table 96 provides 1500 compounds of formula (Ia) wherein $R^1$ is $C(O)OCH_2CH_3$, $R^2$ is F, and $X_2$, $X_3$, $R^3$, $X_1$, $R^5$ are as defined in Table P.

Table 97

Table 97 provides 1500 compounds of formula (Ia) wherein $R^1$ is $CH_2OC(O)CH_3$, $R^2$ is Me, and $X_2$, $X_3$, $R^3$, $X_1$, $R^5$ are as defined in Table P.

Table 98

Table 98 provides 1500 compounds of formula (Ia) wherein $R^1$ is $CH_2OC(O)CH_3$, $R^2$ is Et, and $X_2$, $X_3$, $R^3$, $X_1$, $R^5$ are as defined in Table P.

Table 99

Table 99 provides 1500 compounds of formula (Ia) wherein $R^1$ is $CH_2OC(O)CH_3$, $R^2$ is Pr, and $X_2$, $X_3$, $R^3$, $X_1$, $R^5$ are as defined in Table P.

Table 100

Table 100 provides 1500 compounds of formula (Ia) wherein $R^1$ is $CH_2OC(O)CH_3$, $R^2$ is $N(Et)_2$, and $X_2$, $X_3$, $R^3$, $X_1$, $R^5$ are as defined in Table P.

Table 101

Table 101 provides 1500 compounds of formula (Ia) wherein $R^1$ is $CH_2OC(O)CH_3$, $R^2$ is iPr, and $X_2$, $X_3$, $R^3$, $X_1$, $R^5$ are as defined in Table P.

Table 102

Table 102 provides 1500 compounds of formula (Ia) wherein $R^1$ is $CH_2OC(O)CH_3$, $R^2$ is $N(Me)_2$, and $X_2$, $X_3$, $R^3$, $X_1$, $R^5$ are as defined in Table P.

Table 103

Table 103 provides 1500 compounds of formula (Ia) wherein $R^1$ is $CH_2OC(O)CH_3$, $R^2$ is cBu, and $X_2$, $X_3$, $R^3$, $X_1$, $R^5$ are as defined in Table P.

Table 104

Table 104 provides 1500 compounds of formula (Ia) wherein $R^1$ is $CH_2OC(O)CH_3$, $R^2$ is NHEt, and $X_2$, $X_3$, $R^3$, $X_1$, $R^5$ are as defined in Table P.

Table 105

Table 105 provides 1500 compounds of formula (Ia) wherein $R^1$ is $CH_2OC(O)CH_3$, $R^2$ is $CH_2CF_3$, and $X_2$, $X_3$, $R^3$, $X_1$, $R^5$ are as defined in Table P.

Table 106

Table 106 provides 1500 compounds of formula (Ia) wherein $R^1$ is $CH_2OC(O)CH_3$, $R^2$ is NHMe, and $X_2$, $X_3$, $R^3$, $X_1$, $R^5$ are as defined in Table P.

Table 107

Table 107 provides 1500 compounds of formula (Ia) wherein $R^1$ is $CH_2OC(O)CH_3$, $R^2$ is NMeEt, and $X_2$, $X_3$, $R^3$, $X_1$, $R^5$ are as defined in Table P.

Table 108

Table 108 provides 1500 compounds of formula (Ia) wherein $R^1$ is $CH_2OC(O)CH_3$, $R^2$ is cPr, and $X_2$, $X_3$, $R^3$, $X_1$, $R^5$ are as defined in Table P.

Table 109

Table 109 provides 1500 compounds of formula (Ia) wherein $R^1$ is $CH_2OC(O)CH_3$, $R^2$ is $CH_2Cl$, and $X_2$, $X_3$, $R^3$, $X_1$, $R^5$ are as defined in Table P.

Table 110

Table 110 provides 1500 compounds of formula (Ia) wherein $R^1$ is $CH_2OC(O)CH_3$, $R^2$ is $CH_2F$, and $X_2$, $X_3$, $R^3$, $X_1$, $R^5$ are as defined in Table P.

Table 111

Table 111 provides 1500 compounds of formula (Ia) wherein $R^1$ is $CH_2OC(O)CH_3$, $R^2$ is $CHF_2$, and $X_2$, $X_3$, $R^3$, $X_1$, $R^5$ are as defined in Table P.

Table 112

Table 112 provides 1500 compounds of formula (Ia) wherein $R^1$ is $CH_2OC(O)CH_3$, $R^2$ is F, and $X_2$, $X_3$, $R^3$, $X_1$, $R^5$ are as defined in Table P.

Table 113

Table 113 provides 1500 compounds of formula (Ia) wherein $R^1$ is $CH_2OC(O)CH(CH_3)_2$, $R^2$ is Me, and $X_2$, $X_3$, $R^3$, $X_1$, $R^5$ are as defined in Table P.

Table 114

Table 114 provides 1500 compounds of formula (Ia) wherein $R^1$ is $CH_2OC(O)CH(CH_3)_2$, $R^2$ is Et, and $X_2$, $X_3$, $R^3$, $X_1$, $R^5$ are as defined in Table P.

Table 115

Table 115 provides 1500 compounds of formula (Ia) wherein $R^1$ is $CH_2OC(O)CH(CH_3)_2$, $R^2$ is Pr, and $X_2$, $X_3$, $R^3$, $X_1$, $R^5$ are as defined in Table P.

Table 116

Table 116 provides 1500 compounds of formula (Ia) wherein $R^1$ is $CH_2OC(O)CH(CH_3)_2$, $R^2$ is $N(Et)_2$, and $X_2$, $X_3$, $R^3$, $X_1$, $R^5$ are as defined in Table P.

Table 117

Table 117 provides 1500 compounds of formula (Ia) wherein $R^1$ is $CH_2OC(O)CH(CH_3)_2$, $R^2$ is iPr, and $X_2$, $X_3$, $R^3$, $X_1$, $R^5$ are as defined in Table P.

Table 118

Table 118 provides 1500 compounds of formula (Ia) wherein $R^1$ is $CH_2OC(O)CH(CH_3)_2$, $R^2$ is $N(Me)_2$, and $X_2$, $X_3$, $R^3$, $X_1$, $R^5$ are as defined in Table P.

Table 119

Table 119 provides 1500 compounds of formula (Ia) wherein $R^1$ is $CH_2OC(O)CH(CH_3)_2$, $R^2$ is cBu, and $X_2$, $X_3$, $R^3$, $X_1$, $R^5$ are as defined in Table P.

Table 120

Table 120 provides 1500 compounds of formula (Ia) wherein $R^1$ is $CH_2OC(O)CH(CH_3)_2$, $R^2$ is NHEt, and $X_2$, $X_3$, $R^3$, $X_1$, $R^5$ are as defined in Table P.

Table 121

Table 121 provides 1500 compounds of formula (Ia) wherein $R^1$ is $CH_2OC(O)CH(CH_3)_2$, $R^2$ is $CH_2CF_3$, and $X_2$, $X_3$, $R^3$, $X_1$, $R^5$ are as defined in Table P.

Table 122

Table 122 provides 1500 compounds of formula (Ia) wherein $R^1$ is $CH_2OC(O)CH(CH_3)_2$, $R^2$ is NHMe, and $X_2$, $X_3$, $R^3$, $X_1$, $R^5$ are as defined in Table P.

Table 123

Table 123 provides 1500 compounds of formula (Ia) wherein $R^1$ is $CH_2OC(O)CH(CH_3)_2$, $R^2$ is NMeEt, and $X_2$, $X_3$, $R^3$, $X_1$, $R^5$ are as defined in Table P.

Table 124

Table 124 provides 1500 compounds of formula (Ia) wherein $R^1$ is $CH_2OC(O)CH(CH_3)_2$, $R^2$ is cPr, and $X_2$, $X_3$, $R^3$, $X_1$, $R^5$ are as defined in Table P.

Table 125

Table 125 provides 1500 compounds of formula (Ia) wherein $R^1$ is $CH_2OC(O)CH(CH_3)_2$, $R^2$ is $CH_2Cl$, and $X_2$, $X_3$, $R^3$, $X_1$, $R^5$ are as defined in Table P.

Table 126

Table 126 provides 1500 compounds of formula (Ia) wherein $R^1$ is $CH_2OC(O)CH(CH_3)_2$, $R^2$ is $CH_2F$, and $X_2$, $X_3$, $R^3$, $X_1$, $R^5$ are as defined in Table P.

Table 127

Table 127 provides 1500 compounds of formula (Ia) wherein $R^1$ is $CH_2OC(O)CH(CH_3)_2$, $R^2$ is $CHF_2$, and $X_2$, $X_3$, $R^3$, $X_1$, $R^5$ are as defined in Table P.

Table 128

Table 128 provides 1500 compounds of formula (Ia) wherein $R^1$ is $CH_2OC(O)CH(CH_3)_2$, $R^2$ is F, and $X_2$, $X_3$, $R^3$, $X_1$, $R^5$ are as defined in Table P.

Tables 1b to 128b: Compounds of Formula (Ib)

The invention is further illustrated by making available the following individual compounds of formula (Ib) in Tables 1b to 128b.

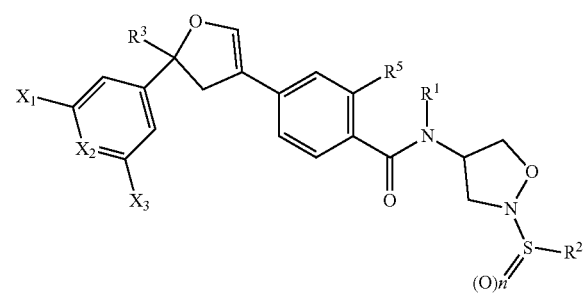

(Ib)

Each of Tables 1b to 128b make available 1500 compounds of the formula (Ib) in which $X_2$, $X_3$, $R^3$, $X_1$ and $R^5$ are the substituents defined in Table P and $R^1$ and $R^2$ are the substituents defined in the relevant Table 1 to 128. Thus Table 1 b individualises 1500 compounds of formula (Ib) wherein for each row of Table P, the $R^1$ and $R^2$ substituents are as defined in Table 1; similarly, Table 2b individualises 1500 compounds of formula (Ib) wherein for each row of Table P, the $R^1$ and $R^2$ substituents are as defined in Table 2; and so on for Tables 3b to 128b.

Each compound disclosed in Tables 1b to 128b represents a disclosure of a compound according to the compound of formula (I*) in which $B^1$-$B^2$-$B^3$-$B^4$ is —$CH_2$—C=CH—O—, and a disclosure according to the compound of formula (I**) in which $B^1$-$B^2$-$B^3$-$B^4$ is —$CH_2$—C=CH—O— as well as mixtures thereof.

Tables 1c to 128c: Compounds of Formula (Ic)

The invention is further illustrated by making available the following individual compounds of formula (Ic) in Tables 1c to 128c.

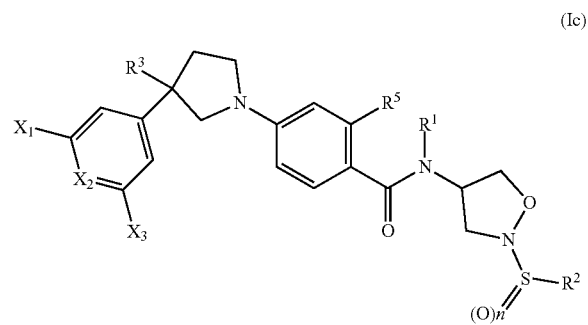

(Ic)

Each of Tables 1c to 128c make available 1500 compounds of the formula (Ic) in which $X_2$, $X_3$, $R^3$, $X_1$ and $R^5$ are the substituents defined in Table P and $R^1$ and $R^2$ are the substituents defined in the relevant Table 1 to 128. Thus Table 1c individualises 1500 compounds of formula (Ic) wherein for each row of Table P, the $R^1$ and $R^2$ and $X_2$ substituents are as defined in Table 1; similarly, Table 2c individualises 1500 compounds of formula (Ic) wherein for each row of Table P, the $R^1$ and $R^2$ and $X_2$ substituents are as defined in Table 2; and so on for Tables 3c to 128c.

Each compound disclosed in Tables 1c to 128c represents a disclosure of a compound according to the compound of formula (I*) in which $B^1$-$B^2$-$B^3$-$B^4$ is —$CH_2$—N—$CH_2$—$CH_2$—, and a disclosure according to the compound of formula (I**) in which $B^1$-$B^2$-$B^3$-$B^4$ is —$CH_2$—N—$CH_2$—$CH_2$— as well as mixtures thereof.

Tables 1d to 128d: Compounds of Formula (Id)

The invention is further illustrated by making available the following individual compounds of formula (Id) in Tables 1d to 128d.

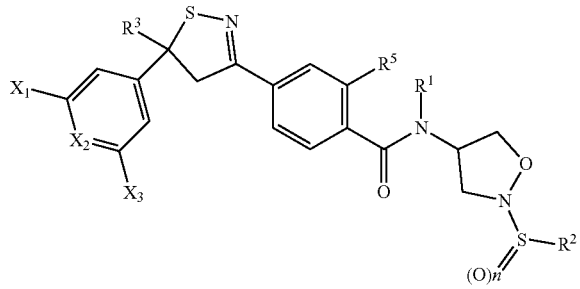

(Id)

Each of Tables 1d to 128d make available 1500 compounds of the formula (Id) in which $X_2$, $X_3$, $R^3$, $X_1$ and $R^5$ are the substituents defined in Table P and $R^1$ and $R^2$ are the substituents defined in the relevant Table 1 to 128. Thus Table 1d individualises 1500 compounds of formula (Id) wherein for each row of Table P, the $R^1$ and $R^2$ substituents are as defined in Table 1; similarly, Table 2d individualises 1500 compounds of formula (Id) wherein for each row of Table P, the $R^1$ and $R^2$ substituents are as defined in Table 2; and so on for Tables 3d to 128d.

Each compound disclosed in Tables 1d to 128d represents a disclosure of a compound according to the compound of formula (I*) in which $B^1$-$B^2$-$B^3$-$B^4$ is —$CH_2$—C=N—S—, and a disclosure according to the compound of formula (I**) in which $B^1$-$B^2$-$B^3$-$B^4$ is —$CH_2$—C=N—S— as well as mixtures thereof.

Tables 1e to 128e: Compounds of Formula (Ie)

The invention is further illustrated by making available the following individual compounds of formula (Ie) in Tables 1e to 128e.

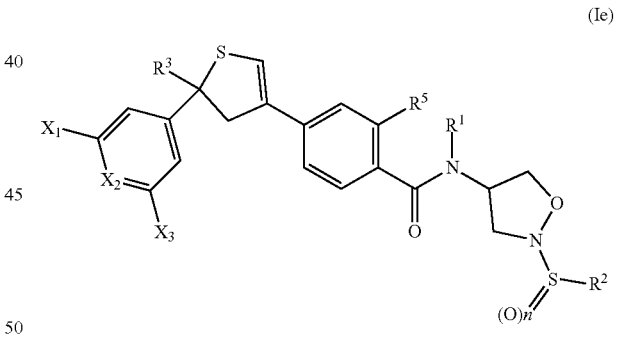

(Ie)

Each of Tables 1e to 128e make available 1500 compounds of the formula (Ie) in which $X_2$, $X_3$, $R^3$, $X_1$ and $R^5$ are the substituents defined in Table P and $R^1$ and $R^2$ 2 are the substituents defined in the relevant Table 1 to 128. Thus Table 1e individualises 1500 compounds of formula (Ie) wherein for each row of Table P, the $R^1$ and $R^2$ substituents are as defined in Table 1; similarly, Table 2e individualises 1500 compounds of formula (Ie) wherein for each row of Table P, the $R^1$ and $R^2$ substituents are as defined in Table 2; and so on for Tables 3e to 128e.

Each compound disclosed in Tables 1e to 128e represents a disclosure of a compound according to the compound of formula (I*) in which $B^1$-$B^2$-$B^3$-$B^4$ is —$CH_2$—C=CH—S—, and a disclosure according to the compound of formula (I**) in which $B^1$-$B^2$-$B^3$-$B^4$ is —$CH_2$—C=CH—S— as well as mixtures thereof.

Tables 1f to 128f: Compounds of Formula (If)

The invention is further illustrated by making available the following individual compounds of formula (If) in Tables 1f to 128f.

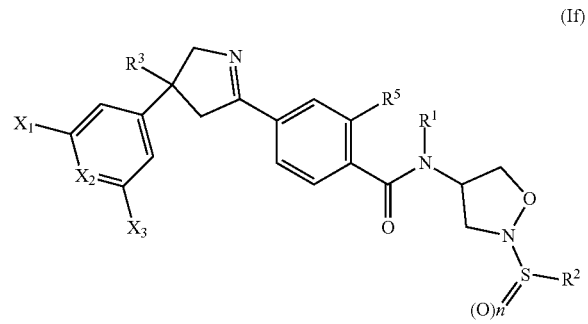

(If)

Each of Tables 1f to 128f make available 1500 compounds of the formula (If) in which $X_2$, $X_3$, $R^3$, $X_1$ and $R^5$ are the substituents defined in Table P and $R^1$ and $R^2$ are the substituents defined in the relevant Table 1 to 128. Thus Table 1f individualises 1500 compounds of formula (If) wherein for each row of Table P, the $R^1$ and $R^2$ substituents are as defined in Table 1; similarly, Table 2f individualises 1500 compounds of formula (If) wherein for each row of Table P, the $R^1$ and $R^2$ substituents are as defined in Table 2; and so on for Tables 3f to 128f.

Each compound disclosed in Tables 1f to 128f represents a disclosure of a compound according to the compound of formula (I*) in which $B^1$-$B^2$-$B^3$-$B^4$ is —$CH_2$—C=N—$CH_2$— and a disclosure according to the compound of formula (I**) in which $B^1$-$B^2$-$B^3$-$B^4$ is —$CH_2$—C=N—$CH_2$— as well as mixtures thereof.

Tables 1g-1 to 128g-1: Compounds of Formula (Ig)

The invention is further illustrated by making available the following individual compounds of formula (Ig) in Tables 1g-1 to 128g-1.

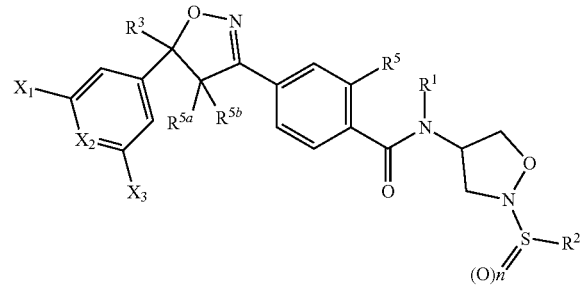

(Ig)

Each of Tables 1g-1 to 128g-1 make available 1500 compounds of the formula (Ig) in which $X_2$, $X_3$, $R^3$, $X_1$ and $R^5$ are the substituents defined in Table P and $R^1$ and $R^2$ are the substituents defined in the relevant Table 1 to 128 and $R^{5a}$ is Cl and $R^{5b}$ is H. Thus Table 1g individualises 1500 compounds of formula (Ig) wherein for each row of Table P, the $R^1$ and $R^2$ substituents are as defined in Table 1 and $R^{5a}$ is Cl and $R^{5b}$ is H; similarly, Table 2g individualises 1500 compounds of formula (Ig) wherein for each row of Table P, the $R^1$ and $R^2$ substituents are as defined in Table 2 and $R^{5a}$ is Cl and $R^{5b}$ is H; and so on for Tables 3g to 128g.

Each compound disclosed in Tables 1g-1 to 128g-1 represents a disclosure of a compound according to the compound of formula (I*) in which $B^1$-$B^2$-$B^3$-$B^4$ is —$C(R^{5a}R^{5b})$—C=N—O— and a disclosure according to the compound of formula (I**) in which $B^1$-$B^2$-$B^3$-$B^4$ is —$C(R^{5a}R^{5b})$—C=N—O— as well as mixtures thereof.

Tables 1g-2 to 128g-2: Compounds of Formula (Ig)

The invention is further illustrated by making available the following individual compounds of formula (Ig) in Tables 1g-2 to 128g-2. Each of Tables 1g-2 to 128g-2 make available 1500 compounds of the formula (Ig) in which $X_2$, $X_3$, $R^3$, $X_1$ and $R^5$ are the substituents defined in Table P and $R^1$ and $R^2$ are the substituents defined in the relevant Table 1 to 128 and $R^{5a}$ is Br and $R^{5b}$ is H.

Tables 1g-3 to 128g-3: Compounds of Formula (Ig)

The invention is further illustrated by making available the following individual compounds of formula (Ig) in Tables 1g-3 to 128g-3. Each of Tables 1g-3 to 128g-3 make available 1500 compounds of the formula (Ig) in which $X_2$, $X_3$, $R^3$, $X_1$ and $R^5$ are the substituents defined in Table P and $R^1$ and $R^2$ are the substituents defined in the relevant Table 1 to 128 and $R^{5a}$ is OH and $R^{5b}$ is H.

Tables 1g-4 to 128g-4: Compounds of Formula (Ig)

The invention is further illustrated by making available the following individual compounds of formula (Ig) in Tables 1g-4 to 128g-4. Each of Tables 1g-4 to 128g-4 make available 1500 compounds of the formula (Ig) in which $X_2$, $X_3$, $R^3$, $X_1$ and $R^5$ are the substituents defined in Table P and $R^1$ and $R^2$ are the substituents defined in the relevant Table 1 to 128 and $R^{5a}$ is F and $R^{5b}$ is H.

Tables 1h to 128h: Compounds of Formula (Ih)

The invention is further illustrated by making available the following individual compounds of formula (Ih) in Tables 1h to 128h.

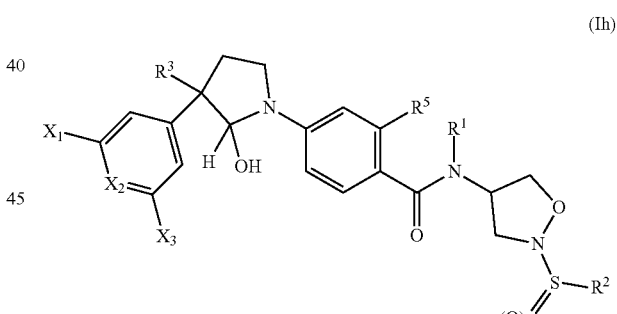

(Ih)

Each of Tables 1h to 128h make available 1500 compounds of the formula (Ih) in which $X_2$, $X_3$, $R^3$, $X_1$ and $R^5$ are the substituents defined in Table P and $R^1$ and $R^2$ are the substituents defined in the relevant Table 1 to 128. Thus Table 1h individualises 1500 compounds of formula (Ih) wherein for each row of Table P, the $R^1$ and $R^2$ substituents are as defined in Table 1; similarly, Table 2h individualises 1500 compounds of formula (Ih) wherein for each row of Table P, the $R^1$ and $R^2$ substituents are as defined in Table 2; and so on for Tables 3f to 128f.

Each compound disclosed in Tables 1h to 128h represents a disclosure of a compound according to the compound of formula (I*) in which $B^1$-$B^2$-$B^3$-$B^4$ is —CH(OH)—N—$CH_2$—$CH_2$— and a disclosure according to the compound of formula (I**) in which $B^1$-$B^2$-$B^3$-$B^4$ is —CH(OH)—N—$CH_2$—$CH_2$— as well as mixtures thereof.

Tables 1j to 128j: Compounds of Formula (Ij)

The invention is further illustrated by making available the following individual compounds of formula (Ij) in Tables 1j to 128j.

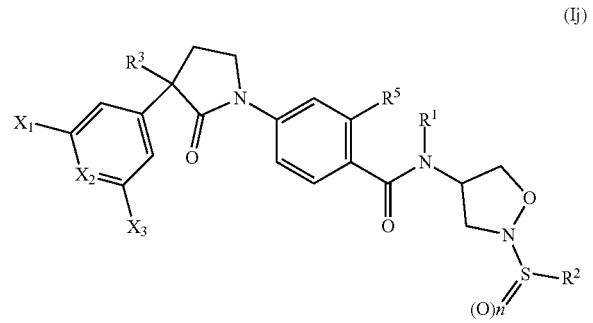

(Ij)

Each of Tables 1j to 128j make available 1500 compounds of the formula (Ij) in which $X_2$, $X_3$, $R^3$, $X_1$ and $R^5$ are the substituents defined in Table P and $R^1$ and $R^2$ are the substituents defined in the relevant Table 1 to 128. Thus Table 1j individualises 1500 compounds of formula (Ij) wherein for each row of Table P, the $R^1$ and $R^2$ substituents are as defined in Table 1; similarly, Table 2j individualises 1500 compounds of formula (Ih) wherein for each row of Table P, the $R^1$ and $R^2$ substituents are as defined in Table 2; and so on for Tables 3j to 128j.

Each compound disclosed in Tables 1j to 128j represents a disclosure of a compound according to the compound of formula (I*) in which $B^1$-$B^2$-$B^3$-$B^4$ is —C(O)—N—CH$_2$—CH$_2$— and a disclosure according to the compound of formula (I**) in which $B^1$-$B^2$-$B^3$-$B^4$ is —C(O)—N—CH$_2$—CH$_2$— as well as mixtures thereof.

Tables 1k to 128k: Compounds of Formula (Ik)

The invention is further illustrated by making available the following individual compounds of formula (Ik) in Tables 1k to 128k.

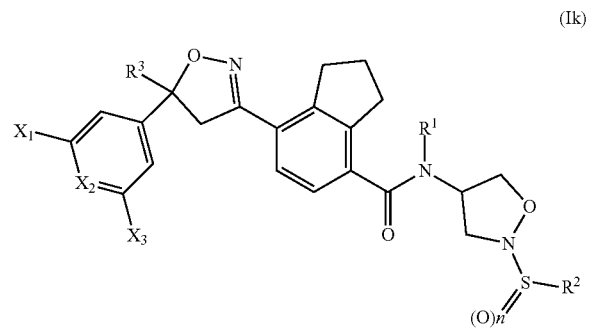

(Ik)

Each of Tables 1k to 128k make available 1500 compounds of the formula (Ik) in which $X_2$, $X_3$, $R^3$ and $X_1$ are the substituents defined in Table P (thus the meaning of the substituent $R^5$ can be disregarded in the Table P for the Tables 1k to 128k) and $R^1$ and $R^2$ are the substituents defined in the relevant Table 1 to 128. Thus Table 1k individualises 1500 compounds of formula (Ik) wherein for each row of Table P, the $R^1$ and $R^2$ substituents are as defined in Table 1; similarly, Table 2k individualises 1500 compounds of formula (Ik) wherein for each row of Table P, the $R^1$ and $R^2$ substituents are as defined in Table 2; and so on for Tables 3k to 128k.

Each compound disclosed in Tables 1k to 128k represents a disclosure of a compound according to the compound of formula (I*) in which $B^1$-$B^2$-$B^3$-$B^4$ is —CH$_2$—C=N—O— and a disclosure according to the compound of formula (I**) in which $B^1$-$B^2$-$B^3$-$B^4$ is —CH$_2$—C=N—O— as well as mixtures thereof.

Tables 1l to 128l: Compounds of formula (I-1) The invention is further illustrated by making available the following individual compounds of formula (I-1) in Tables 1l to 128l.

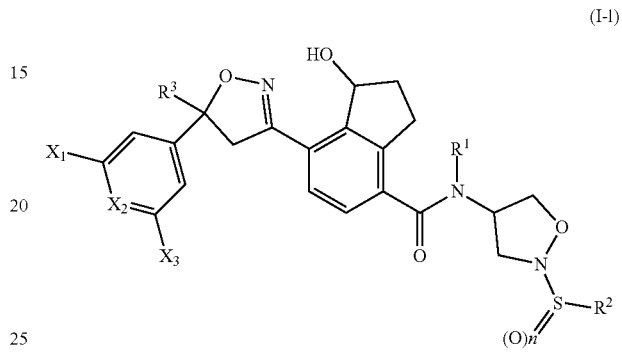

(I-1)

Each of Tables 1l to 128l make available 1500 compounds of the formula (I-1) in which $X_2$, $X_3$, $R^3$ and $X_1$ are the substituents defined in Table P (thus the meaning of the substituent $R^5$ can be disregarded in the Table P for the Tables 1l to 128l) and $R^1$ and $R^2$ are the substituents defined in the relevant Table 1 to 128. Thus Table 1l individualises 1500 compounds of formula (I-1) wherein for each row of Table P, the $R^1$ and $R^2$ substituents are as defined in Table 1; similarly, Table 2l individualises 1500 compounds of formula (I-1) wherein for each row of Table P, the $R^1$ and $R^2$ substituents are as defined in Table 2; and so on for Tables 3l to 128l.

Each compound disclosed in Tables 1l to 128l represents a disclosure of a compound according to the compound of formula (I*) in which $B^1$-$B^2$-$B^3$-$B^4$ is —CH$_2$—C=N—O— and a disclosure according to the compound of formula (I**) in which $B^1$-$B^2$-$B^3$-$B^4$ is —CH$_2$—C=N—O— as well as mixtures thereof.

Tables 1m to 128m: Compounds of formula (Im)

The invention is further illustrated by making available the following individual compounds of formula (Im) in Tables 1m to 128m.

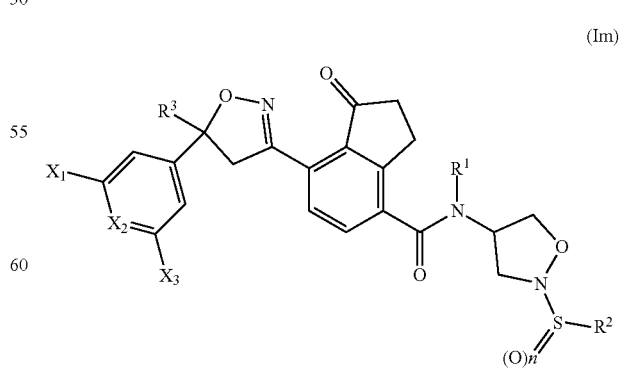

(Im)

Each of Tables 1m to 128m make available 1500 compounds of the formula (Im) in which $X_2$, $X_3$, $R^3$ and $X_1$ are the substituents defined in Table P (thus the meaning of the substituent $R^5$ can be disregarded in the Table P for the Tables 1m to 128m) and $R^1$ and $R^2$ are the substituents defined in the relevant Table 1 to 128. Thus Table 1m individualises 1500 compounds of formula (Im) wherein for each row of Table P, the $R^1$ and $R^2$ substituents are as defined in Table 1; similarly, Table 2m individualises 1500 compounds of formula (Im) wherein for each row of Table P, the $R^1$ and $R^2$ substituents are as defined in Table 2; and so on for Tables 3m to 128m.

Each compound disclosed in Tables 1m to 128m represents a disclosure of a compound according to the compound of formula (I*) in which $B^1$-$B^2$-$B^3$-$B^4$ is —CH$_2$—C=N—O— and a disclosure according to the compound of formula (I**) in which $B^1$-$B^2$-$B^3$-$B^4$ is —CH$_2$—C=N—O— as well as mixtures thereof.

Examples of compounds of formula (Int-I) made available are those where $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$, $R^5$ and $R^2$ each correspond to a substitutent $R^1$, $R^5$ and $R^2$ respectively as defined in each of Tables 1 to 128 above in context of formula (Ia), So for example, Table 1 individualises a compound of formula (Int-I) wherein $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$, $R^5$ and $R^2$ are each as defined in Table 1; similarly, Table 2 individualises a compound of formula (Int-I) wherein $X^B$ is bromo, chloro, iodo, cyano, formyl, CH=NOH or acetyl, $A^2$, $A^3$ and $A^4$ are each CH, n is 2, $A^1$ is $CR^5$, and wherein $R^1$, $R^5$ and $R^2$ are each as defined in Table 2; and so on for Tables 3 to 128.

Examples of compounds of formula (Int-II) made available are those where $X^c$ is CH$_2$C$_1$, CH$_2$Br, CH=C(CF$_3$)(3-chloro-5-trifluoromethyl-phenyl), CH=C(CF$_3$)(3-bromo-5-trifluoromethyl-phenyl), CH=C(CF$_3$)(3,5-dichloro-4-fluoro-phenyl), CH=C(CF$_3$)(3,4,5-trichloro-phenyl), CH$_2$C(OH)(CF$_3$)(3-chloro-5-trifluoromethyl-phenyl), CH$_2$C(OH)(CF$_3$)(3-bromo-5-trifluoromethyl-phenyl), CH$_2$C(OH)(CF$_3$)(3,5-dichloro-4-fluoro-phenyl) or CH$_2$C(OH)(CF$_3$)(3,4,5-trichloro-phenyl), A2, A3 and A4 are each CH, n is 2, A1 is $CR^5$, and wherein $R^1$, $R^5$ and $R^2$ each correspond to a substitutent $R^1$, $R^5$ and $R^2$ respectively as defined in each of Tables 1 to 128 above in context of formula (Ia), So for example, Table 1 individualises a compound of formula (Int-II) wherein $X^c$ is CH$_2$C$_1$, CH$_2$Br, CH=C(CF$_3$)(3-chloro-5-trifluoromethyl-phenyl), CH=C(CF$_3$)(3-bromo-5-trifluoromethyl-phenyl), CH=C(CF$_3$)(3,5-dichloro-4-fluoro-phenyl), CH=C(CF$_3$)(3,4,5-trichloro-phenyl), CH$_2$C(OH)(CF$_3$)(3-chloro-5-trifluoromethyl-phenyl), CH$_2$C(OH)(CF$_3$)(3-bromo-5-trifluoromethyl-phenyl), CH$_2$C(OH)(CF$_3$)(3,5-dichloro-4-fluoro-phenyl) or CH$_2$C(OH)(CF$_3$)(3,4,5-trichloro-phenyl), $A^2$, $A^3$ and $A^4$ are each CH, n is 2, $A^1$ is $CR^5$, and wherein $R^1$, $R^5$ and $R^2$ are each as defined in Table 1; similarly, Table 2 individualises a compound of formula (Int-II) wherein $X^c$ is CH$_2$C$_1$, CH$_2$Br, CH=C(CF$_3$)(3-chloro-5-trifluoromethyl-phenyl), CH=C(CF$_3$)(3-bromo-5-trifluoromethyl-phenyl), CH=C(CF$_3$)(3,5-dichloro-4-fluoro-phenyl), CH=C(CF$_3$)(3,4,5-trichloro-phenyl), CH$_2$C(OH)(CF$_3$)(3-chloro-5-trifluoromethyl-phenyl), CH$_2$C(OH)(CF$_3$)(3-bromo-5-trifluoromethyl-phenyl), CH$_2$C(OH)(CF$_3$)(3,5-dichloro-4-fluoro-phenyl) or CH$_2$C(OH)(CF$_3$)(3,4,5-trichloro-phenyl), A2, A3 and A4 are each CH, n is 2, A1 is $CR^5$, and wherein $R^1$, $R^5$ and $R^2$ are each as defined in Table 2; and so on for Tables 3 to 128.

Examples of compounds of formula (Int-III) made available are those where n is 2, and wherein $R^1$ and $R^2$ correspond to the substitutents $R^1$ and $R^2$ as defined in each of Tables 1 to 128 above in context of formula (Ia), So for example, Table 1 individualises a compound of formula (Int-III) wherein n is 2, and $R^1$ and $R^2$ are as defined in Table 1; similarly, Table 2 individualises a compound of formula (Int-III) wherein n is 2, and wherein $R^1$ and $R^2$ are as defined in Table 2; and so on for Tables 3 to 128.

The compounds of the invention may be made by a variety of methods as shown in Schemes 1 to 20

Scheme 1

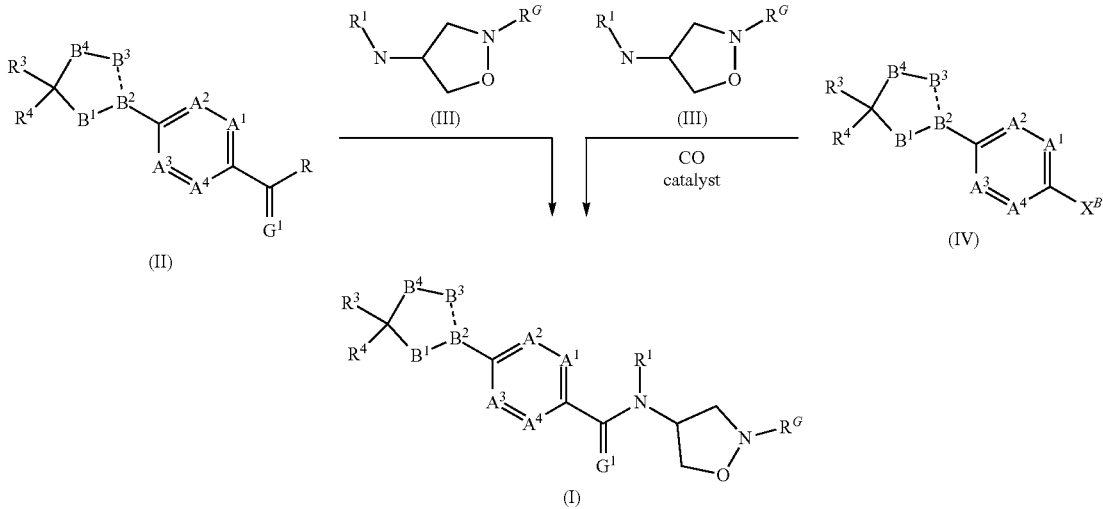

chloro-5-trifluoromethyl-phenyl), CH=C(CF$_3$)(3-bromo-5-trifluoromethyl-phenyl), CH=C(CF$_3$)(3,5-dichloro-4-fluoro-phenyl), CH=C(CF$_3$)(3,4,5-trichloro-phenyl), CH$_2$C(OH)(CF$_3$)(3-chloro-5-trifluoromethyl-phenyl), CH$_2$C(OH)(CF$_3$)(3-bromo-5-trifluoromethyl-phenyl), CH$_2$C(OH)(CF$_3$)(3,5-dichloro-4-fluoro-phenyl) or CH$_2$C(OH)(CF$_3$)(3,4,5-trichloro-phenyl), A2, A3 and A4 are each CH, n is 2, A1 is $CR^5$, and wherein $R^1$, $R^5$ and $R^2$ each correspond to a substitutent $R^1$, $R^5$ and $R^2$ respectively as defined in each of 1) Compounds of formula (I) wherein $G^1$ is oxygen can be prepared by reacting a compound of formula (II) wherein $G^1$ is oxygen and R is OH, $C_1$-$C_6$alkoxy or Cl, F or Br, with an amine of formula (III), wherein $R^G$ is S(O)$_n$$R^2$ or a protecting group, such as a Boc, as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art. Some of these methods are described in the preparation examples.

2) Acid halides of formula (II), wherein $G^1$ is oxygen and R is Cl, F or Br, may be made from carboxylic acids of formula (II), wherein $G^1$ is oxygen and R is OH, under standard conditions, as described for example in WO2008128711

3) Carboxylic acids of formula (II), wherein $G^1$ is oxygen and R is OH, may be formed from esters of formula (II), wherein $G^1$ is oxygen and R is $C_1$-$C_6$alkoxy as described for example in WO2008128711 (when $B^1$-$B^2$-$B^3$-$B^4$ is $CH_2$—N—$CH_2$—$CH_2$—) and WO2009072621 (when $B^1$-$B^2$-$B^3$-$B^4$ is —$CH_2$—C=N—$CH_2$—) and as described below (when $B^1$-$B^2$-$B^3$-$B^4$ is —$CH_2$—C=CH—O— or —CH=C—$CH_2$—O—).

4) Compounds of formula (I) wherein $G^1$ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO09080250.

6) Compounds of formula (I), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

In all the following schemes, $A^1$, $A^2$, $A^3$ and $A^4$ are as described for compounds of formula (I), and P can be a leaving group, for example a halogen, such as bromo, iodo, chloro or described by one of the three groups A and B:

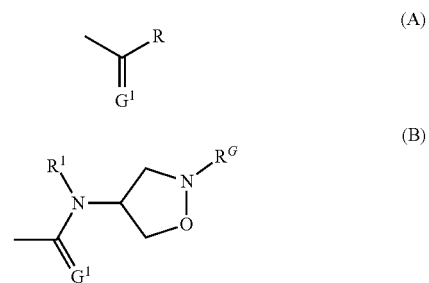

wherein $G^1$ is oxygen and R is OH, $C_1$-$C_{12}$alkoxy or Cl, F or Br, $R^G$ is $S(O)_nR^2$ or a protecting group, such as a Boc and $R^1$, $R^2$, and $G^1$ are as described for compounds of formula (I).

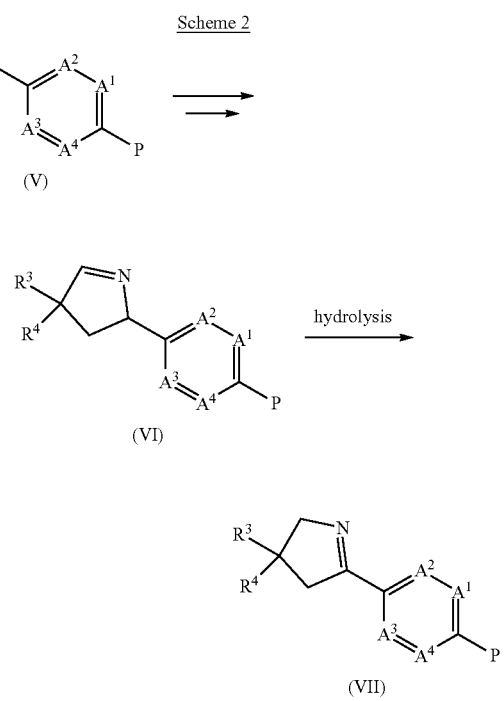

7) Compounds of formula (VII) can be prepared by various methods from an intermediate of formula (VI) as shown in Scheme 2 according to similar methods to those described in WO10149506. An intermediate of formula (VI) can be prepared for example from an intermediate of formula (V) as described in the same reference.

Scheme 3

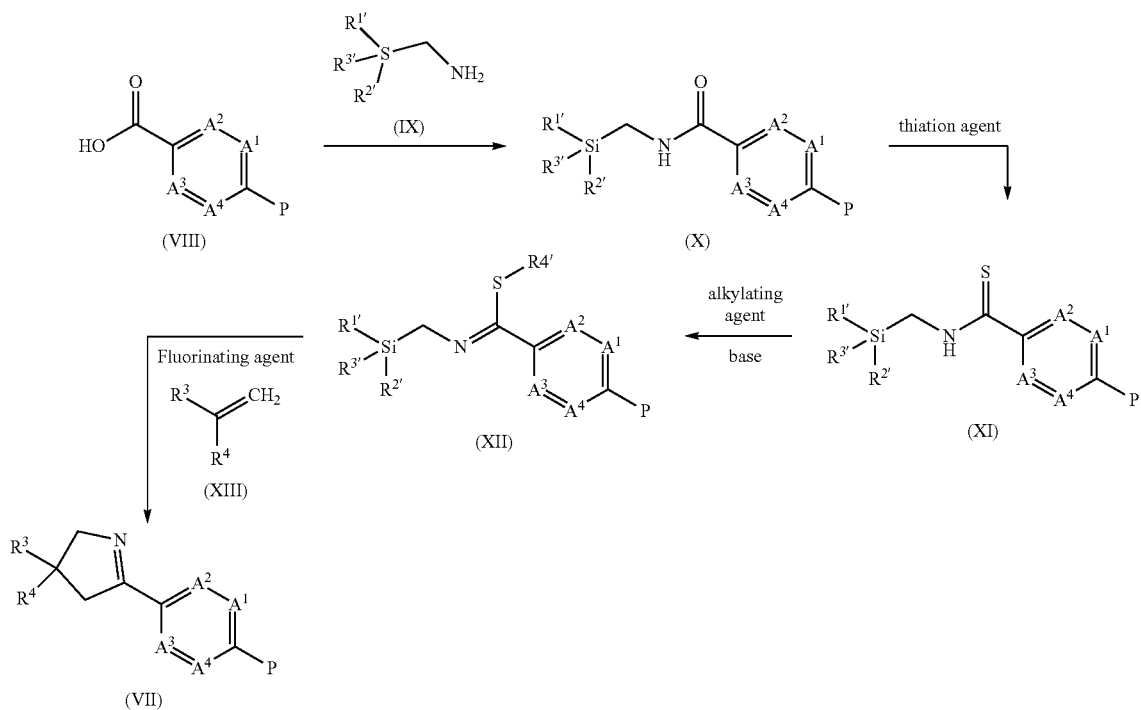

8) Alternatively, compounds of formula (VII) can be prepared by various methods from an intermediate of formula (XII) as shown in Scheme 3 according to similar methods to those described in WO10149506. The intermediates of formula (XII) can be prepared for example as described in the same reference.

9) Alternatively, compounds of formula (VII) can be prepared by various methods from an intermediate of formula (XV) or (XVI) as shown in Scheme 4 according to similar methods to those described in WO10149506. The intermediates of formula (XV) can be prepared for example as described in the same reference.

Scheme 4

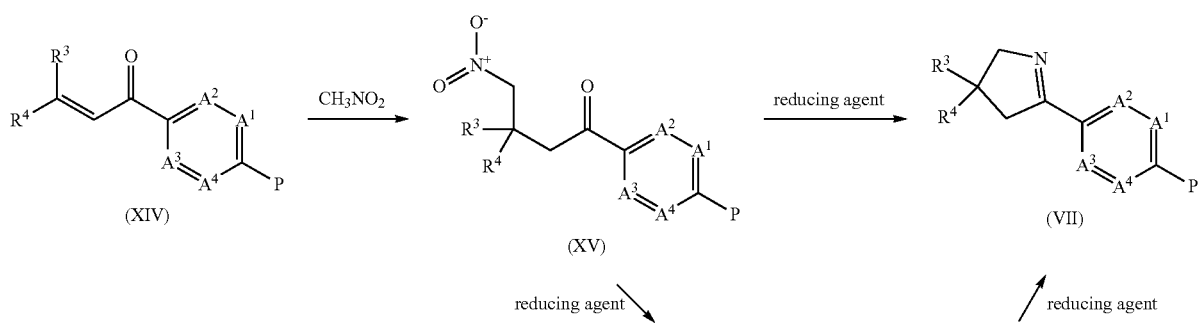

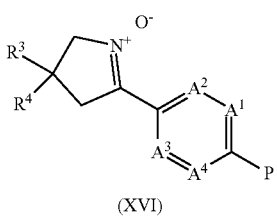

Scheme 5

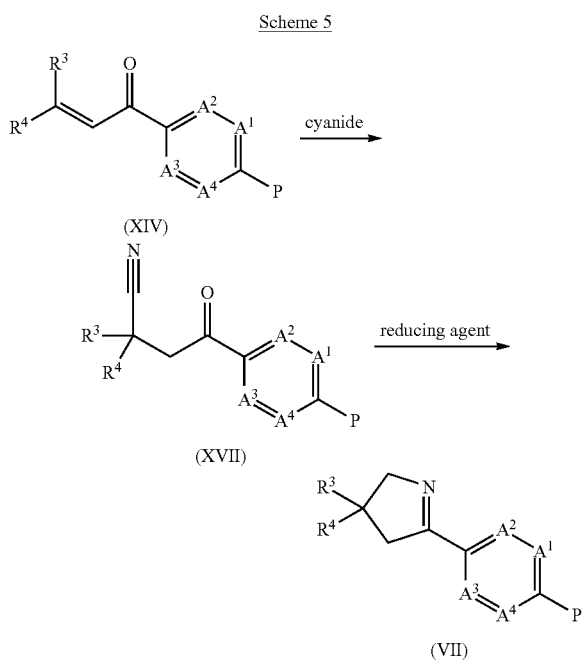

10) Alternatively, compounds of formula (VII) can be prepared by various methods from an intermediate of formula (XVII) as shown in Scheme 5 according to similar methods to those described in WO10149506. The intermediates of formula (XVII) can be prepared for example as described in the same reference.

substituted aryl, and Z is optionally substituted alkyl or optionally substituted arylalkylene, can be prepared by reacting a compound of formula (XIV) with a glycine Schiff base of formula (XVIII), in the presence of base. In most cases it is advantageous to conduct the reaction using a solvent at a dilution of 0.1 M to 1 M, preferably 0.3 M to 0.5 M. Suitable organic solvents could be used, for example toluene, 1,2-dichloroethane, dichloromethane, tetrahydrofuran, methanol or ethyl acetate. The reaction temperature is usually between 0° C. to 100° C., preferably between 40 and 100° C. When a solvent is used the reactants are usually at a dilution of e.g. between 0.1 M to 1 M. The reaction time is usually between 0 and 96 hours, preferably between 0 and 12 hours. Suitable bases include amines, such as triethylamine, 2,5-dimethylpiperazine, tetramethylpiperidine, 4-dimethylamino pyridine, potassium carbonate, metal alkoxides, such as sodium t-butoxide or metal fluorides, such as cesium fluoride.

12) Compounds of formula (XX) can be prepared by deprotecting and cyclizing compounds of formula (XIX). Suitable conditions for this transformation include acidic conditions, for instance the presence of strong acids such as trifluoroacetic acid, sulfonic acid or hydrochloric acid. Suitable solvents can be used, for example acetone, dimethylsulfoxide, dimethylformamide, toluene, xylenes, 1,2-dichloroethane, dichloromethane, tetrahydrofuran, methanol ethanol, tert-butanol, water or ethyl acetate at a temperature from 0° C. to 140° C., preferably between 0° C. and 80° C., and at dilution of e.g. between 0.1 M to 1 M. The reaction time is usually between 1 and 24 hours, preferably between 1 and 6 hours.

13) Alternatively, compounds of formula (VII) can be prepared by decarboxylating compounds of formula (XX).

Scheme 6

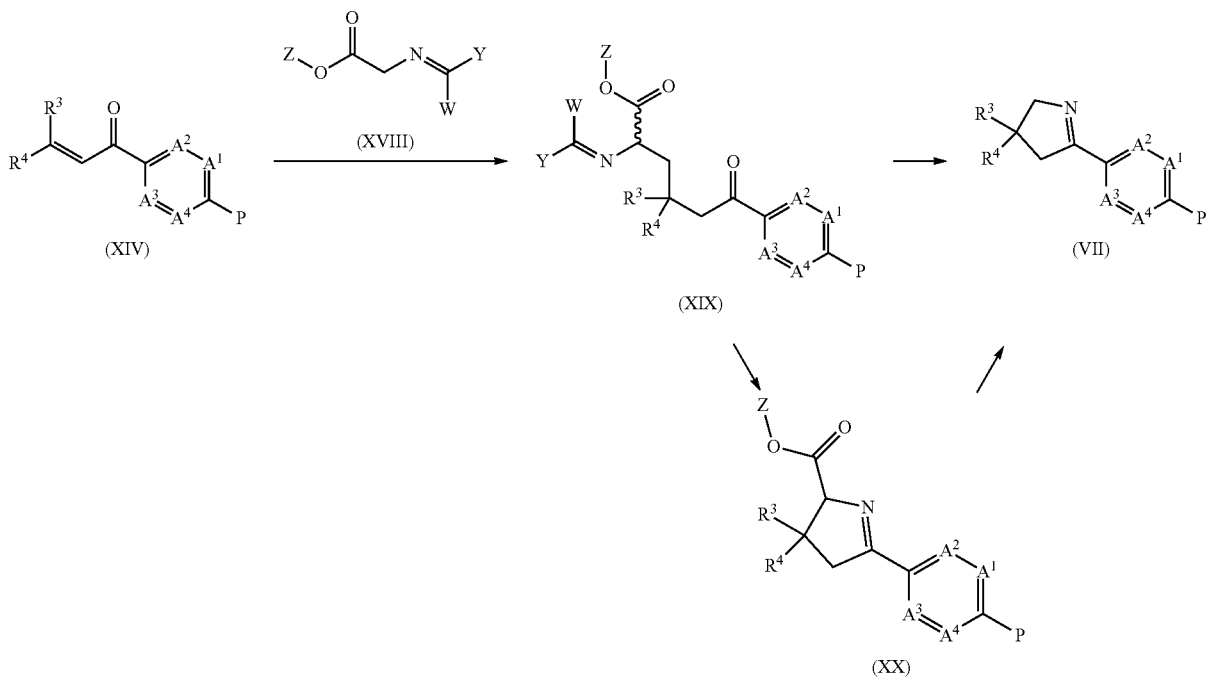

11) Compounds of formula (XIX) wherein $R^3$ and $R^4$ are as defined for the compound of formula I, and wherein W is hydrogen or optionally substituted aryl, Y is optionally Suitable conditions for this transformation involve heating the compounds in a suitable media, which depending on the group Z may include some standard additives known by a person skilled in the art. Suitable solvents can be used, for example acetone, dimethylsulfoxide, dimethylformamide, toluene, xylenes, 1,2-dichloroethane, dichloromethane, tetrahydrofuran, methanol, ethanol, tert-butanol, water or ethyl acetate. The temperature is usually between 0° C. and 200° C., preferably between 50 and 180° C.

Where a solvent is used, the reactants are usually at dilution of e.g. between 0.1 M to 1 M. The reaction time is usually between 0 and 96 hours, preferably between 0 and 24 hours. The reaction can also be performed under microwave conditions, preferably between 40 and 180° C., In some cases, however, it is necessary or useful to add an additive, such as a metal halide, for instance sodium chloride or potassium iodide, or a metal cyanide, such as sodium cyanide to the reaction media, or a base (e.g. when group Z is alkyl). In the case where Z is aryl-methylene (e.g. benzyl), suitable deprotection conditions include hydrogenation conditions. The most useful solvents are alcohols such as methanol or ethanol and in most cases it is advantageous to conduct the reaction at dilution between 0.1 M to 1 M, preferably 0.3 M to 0.5 M. The amount of catalyst, such as palladium on charcoal added is usually between 0.1 molar equivalent and 0.50 molar equivalents and the reaction time in most cases is between 1 hour and 6 hours.

14) Compounds of formula (VII) can be prepared by deprotecting, decarboxylating and cyclizing compounds of formula (XIX) according to a one-pot stepwise procedure without isolating the intermediates. Suitable conditions for this transformation include acidic conditions, for instance the presence of strong acids such as trifluoroacetic acid or hydrochloric acid, or basic conditions, depending on the group Z. Suitable solvents could be used, for example acetone, dimethylsulfoxide, dimethylformamide, toluene, xylenes, 1,2-dichloroethane, dichloromethane, tetrahydrofuran, methanol, ethanol, tert-butanol, water or ethyl acetate. The temperature is usually between 0° C. and 200° C., preferably between 50 and 180° C. Where a solvent is used the reactants are usually at dilution of e.g. between 0.1 M to 1 M. The reaction time is usually between land 96 hours, preferably between 1 and 12 hours. The reaction can also be performed under microwave conditions, preferably between 40 and 180° C. In some cases, however, it is necessary or useful to add an additive, such as a metal halide, for instance sodium chloride or potassium iodide, or a metal cyanide, such as sodium cyanide to the reaction media.

Enantiomerically enriched mixtures of compounds of formula (VII) may be prepared, for example, according to schemes 4, 5 or 6 by formation of intermediate XV, XVII or XIX via an asymmetric Michael addition, see for example J. Org. Chem. 2008, 73, 3475-3480 and references cited therein" and J. Am. Chem. Soc. 2008, 130, 6072-6073.

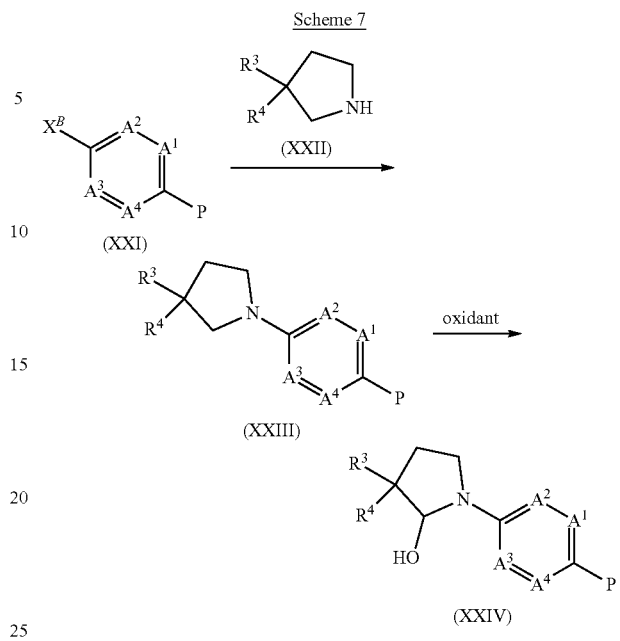

Scheme 7

15) Compounds of formula (XXIII) can be prepared by reaction of compound of formula (XXI) wherein $X^B$ is a halogen, such as bromine or chlorine, with an amine compound of formula (XXII) as shown in Scheme 7 in the absence or the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

Compounds of formula (XXII) can be prepared according to a method developed in the literature: Tetrahedron (1996), 52, (1), 59-70 and Tetrahedron Letters (1993), 34, (20), 3279-82.

16) Compounds of formula (XXI) wherein $X^B$ is a leaving group, for example a halogen, such as bromo, can be prepared as described in WO09080250.

17) compounds of formula (XXIV) can be prepared by reaction of compound of formula (XXIII) with an oxidant, as described in WO12035011.

Scheme 8

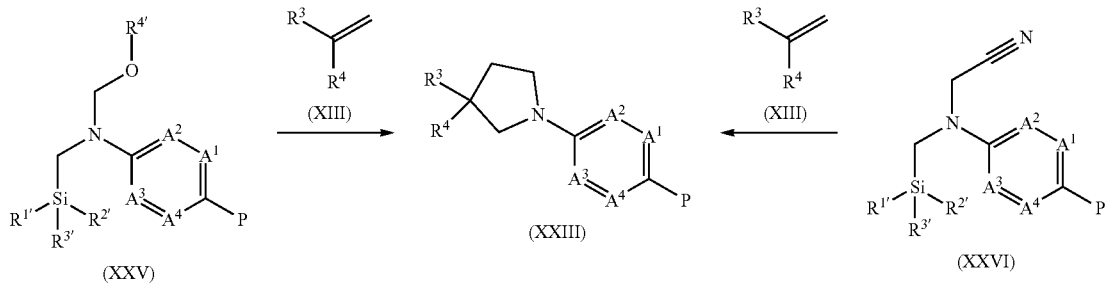

18) Compounds of formula (XXIII) can be prepared by reaction of compound of formula (XXVI) wherein $R^{1'}$, $R^{2'}$ and $R^{3'}$ are independently of each other optionally substituted alkyl or optionally substituted phenyl groups, with styrene of formula (XIII) according to a method developed in the literature: Journal of Medicinal Chemistry (1990), 33(2), 849-54.

19) Compounds of formula (XXIII) can be prepared by reaction of compound of formula (XXV) wherein $R^{4'}$ is optionally substituted alkyl group, $R^{1'}$, $R^{2'}$ and $R^{3'}$ are independently of each other optionally substituted alkyl or optionally substituted phenyl groups, with styrene of formula (XIII) according to a method developed in the literature: Tetrahedron (1996), 52, (1), 59-70 and Tetrahedron Letters (1993), 34, (20), 3279-82.

21) Compounds of formula (XXIX) can be prepared by reaction of compound of formula (XXXI) with a compound of formula (XXI) as described in 15).

Compounds of formula (XXXI) can be prepared by many methods as described in the literature (Bioorganic & Medicinal Chemistry Letters (2010), 20(1), 362-365).

22) Compounds of formula (XXIX) can be prepared by reaction of compound of formula (XXVII) wherein R is OH, $C_1$-$C_6$alkoxy or Cl, F or Br, with a compound of formula (XXVIII) under standard reductive amination conditions.

23) Compounds of formula (XXVII) can be prepared by many methods as described in the literature (US patent US 2005148792).

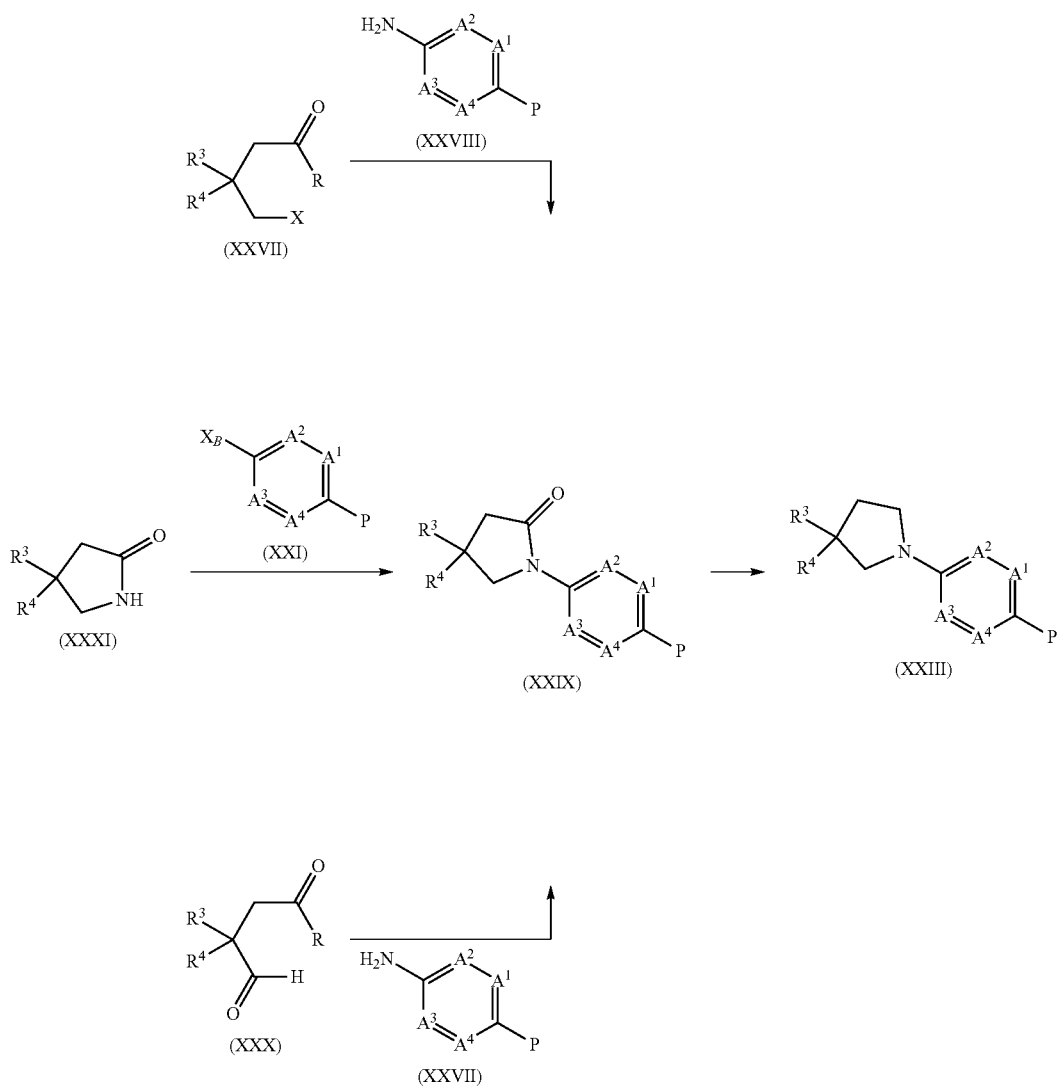

Scheme 9

20) Compounds of formula (XXIII) can be prepared by reduction of compounds of formula (XXIX) with a metal hydride, for instance according to a method developed in the literature: Journal of Pharmaceutical Sciences (1978), 67(7), 953-6.

24) Compounds of formula (XXIX) can be prepared by reaction of compound of formula (XXVII) wherein R is OH, $C_1$-$C_6$alkoxy or Cl, F or Br, and X is a leaving group, such as a mesylate, a tosylate or an halogen with a compound of formula (XXVIII) under standard substitution reaction conditions.

Scheme 10

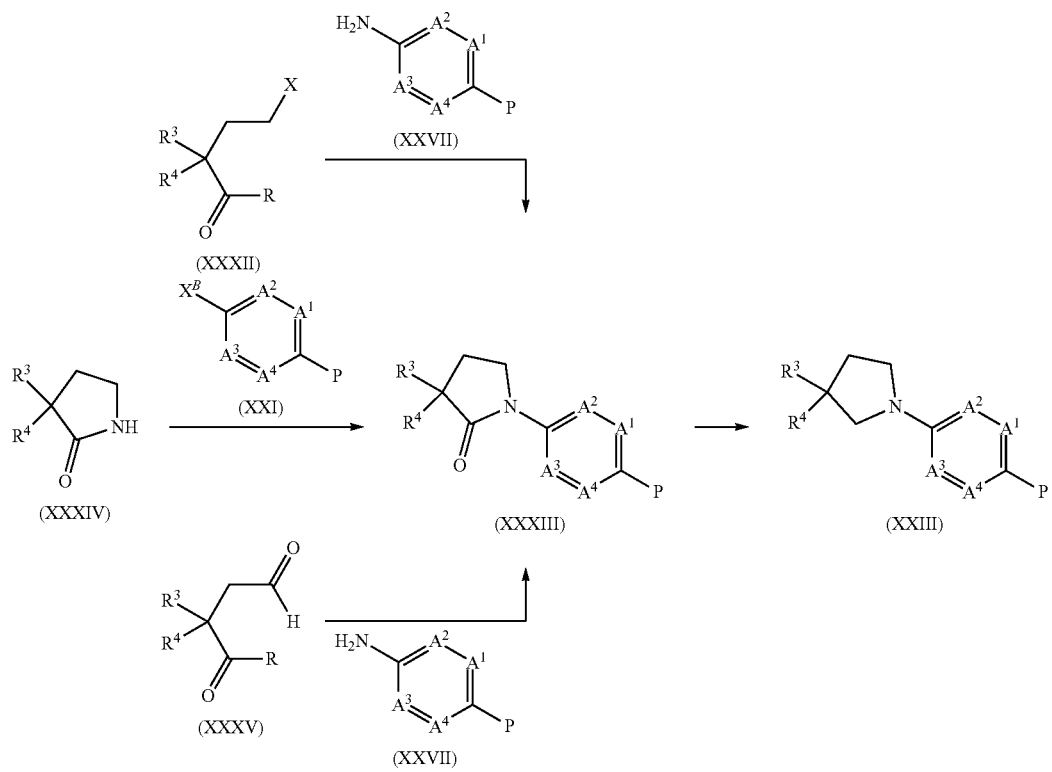

25) Compounds of formula (XXIII) can be prepared by reduction of compounds of formula (XXXIII) with a metal hydride, for instance according to a method developed in the literature: Tetrahedron: Asymmetry (1999), 10(20), 3877-3881

26) Compounds of formula (XXXIII) can be prepared by reaction of compound of formula (XXXIV) with a compound of formula (XXI) as described in 15).

27) Compounds of formula (XXXIV) can be prepared by many methods as described in the literature (Tetrahedron: Asymmetry (1999), 10(20), 3877-3881).

28) Compounds of formula (XXXIII) can be prepared by reaction of compound of formula (XXXV) wherein R is OH, $C_1$-$C_6$alkoxy or Cl, F or Br, with a compound of formula (XXVII) under standard reductive amination conditions.

29) Compounds of formula (XXXV) can be prepared by many methods as described in the literature.

30) Compounds of formula (XXXIV) can be prepared by reaction of compound of formula (XXXII) wherein R is OH, $C_1$-$C_6$alkoxy or Cl, F or Br, and X is a leaving group, such as a mesylate, a tosylate or an halogen with a compound of formula (XXVII) under standard substitution reaction conditions.

Scheme 11

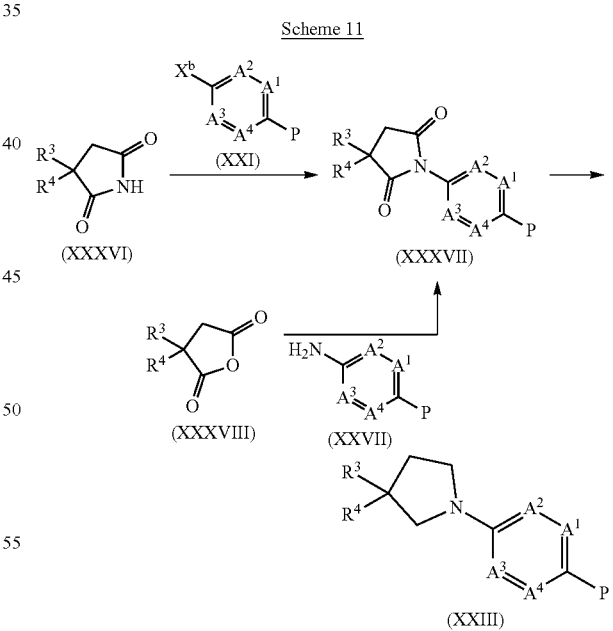

31) Compounds of formula (XXIII) can be prepared by reduction of compounds of formula (XXXVII) with a metal hydride, for instance according to a method developed in the literature (ARKIVOC, 2003, 5, and U.S. Pat. No. 4,524, 206).

32) Compounds of formula (XXXVII) can be prepared by reaction of compound of formula (XXXVI) with a compound of formula (XXI) as described in 15).

33) Compounds of formula (XXXVII) can be prepared by reaction of compound of formula (XXXVIII) with a compound of formula (XXVII) under standard substitution reaction conditions.

Scheme 12

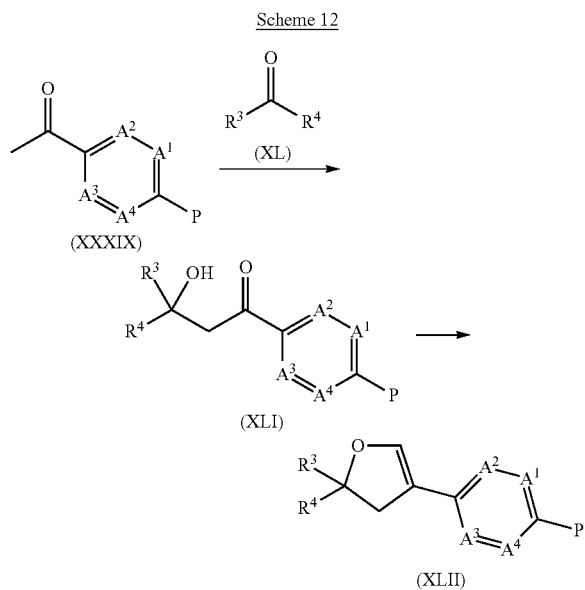

34) Compounds of formula (XLII) can be prepared by reacting a compound of formula (XLI) with trimethylsilyldiazomethane, in the presence of an organometallic reagent, such as methyl lithium, in a suitable solvent, such as tetrahydrofuran, diethyl ether, N, N-dimethylformamide or dimethoxyethane. The reaction is carried out at a temperature of from −78° C. to 100° C., preferably from −78° C. to ambient temperature. Compounds of formula (XLII) are either known compounds or can be prepared using methods described for example in WO2007074789, preferably by reacting a compound of formula (XXXIX) with a ketone of formula (XL).

35) Alternatively, 2,3-dihydrofuran compounds of formula (XLII) may be prepared by isomerisation of 2,5-dihydrofuran of formula (XLVI) using a metal catalyst such as $RhCl(PPh_3)_3$, $RhH(PPh_3)_4$, $H_2Ru(CO)(PPh_3)_3$, $RuCl_3$, $HClRu(CO)(PPh_3)_3$ or $H_2Ru(PPh_3)_4$ in a solvent such as toluene or an alcoholic solvent such as ethanol at a temperature of between room temperature and 150° C., preferably between 80° C. and 120° C. Such conditions of isomerisation of 2,5-dihydrofuran compounds have been described in *Chem. Eur. J.* 2003, 9, 4442-4451 using the general catalytic isomerisation described by M. Mori et al in *J. Org. Chem.* 2000, 65, 3966-3970 or M. Bartok et al in *J. Organomet. Chem.* 1985, 297, C37-C40. Alternatively, the isomerisation may be performed in the presence of basic oxide metal catalysts such as MgO, CaO, SrO, or $La_2O_3$ as described by K. Tanabe in *Chem. Lett.* 1981, 341-342 for the isomerisation of 2,5-dihydrofuran.

36) Compounds of formula (XLII) and (XLVI) can be prepared by reacting a compound of formula (XLIV) wherein $X^1$ is a leaving group, for example a halogen, such as iodo or bromo with a compound of formula (XLIII), in the presence of a metal, such as catalyst, such as magnesium, lithium, indium, cerium or zinc, in a suitable solvent, such as tetrahydrofuran, diethyl ether or N, N-dimethylformamide. The reaction is carried out at a temperature of from −78° C. to 100° C., preferably from −78° C. to ambient temperature.

37) Compounds of formula (XLV) can be prepared by reacting a compound of formula (XLIII) with a compound of formula (XLIV), in the presence of a metal, such as magnesium, indium, cerium, zinc, or an organolithium reagent, such as n-butyl lithium, in a suitable solvent, such as tetrahydrofuran, diethyl ether or N, N-dimethylformamide. The reaction is carried out at a temperature of from −100° C. to 100° C., preferably from −100° C. to ambient temperature.

38) Compounds of formula (XLII) and (XLVI) can be prepared by reacting a compound of formula (XLV) in the presence of an acid, such as p-toluenesulfonic acid or sulphuric acid, or in the presence of a dehydrating agent, such as $POCl_3$ in a suitable solvent, such as tetrahydrofuran, Scheme 13

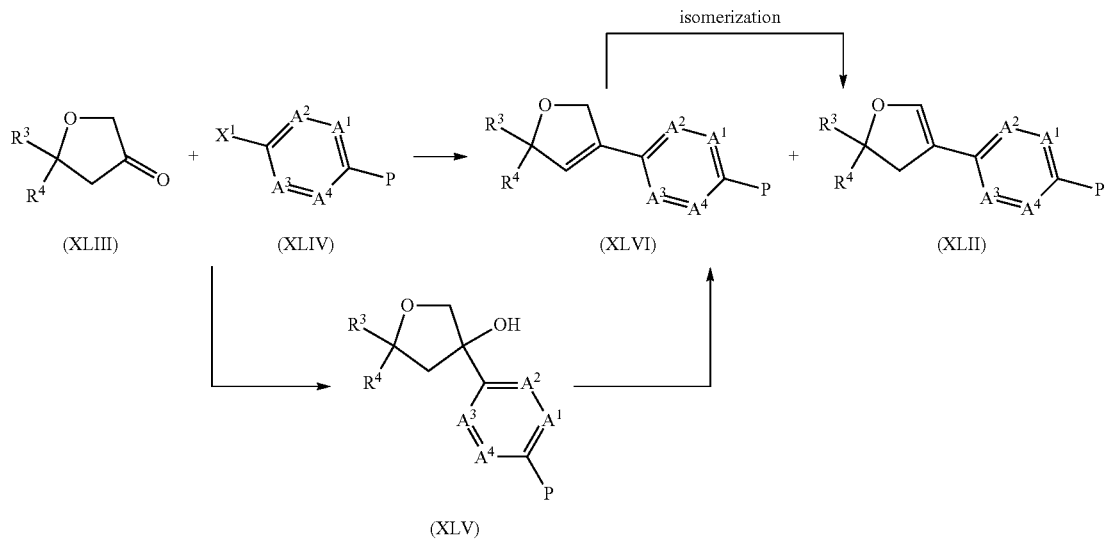

diethyl ether or dichloromethane. The reaction is carried out at a temperature of from −78° C. to 100° C., preferably from −40° C. to ambient temperature.

39) Alternatively, compounds of formula (XLII) and (XLVI) can be obtained by reacting a compound of formula (XLV) in the presence of a chlorinating agent, such as thionyl chloride or oxalyl chloride, or an acetylating agent, such as acetic anhydride in the presence of a base, such as triethylamine, potassium carbonate or pyridine, in a suitable solvent, such as tetrahydrofuran, diethyl ether or dichloromethane. The reaction is carried out at a temperature of from −78° C. to 100° C., preferably from −40° C. to ambient temperature.

40) Compounds of formula (XLIV) are either known compounds or can be prepared by known methods to the person skilled in the art. Compounds of formula (XLIII) can be prepared as described in Scheme 14.

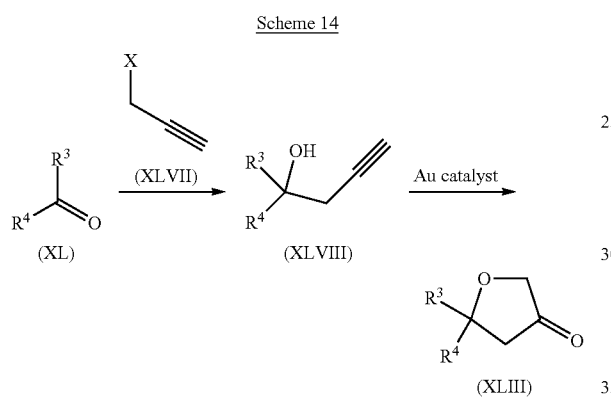

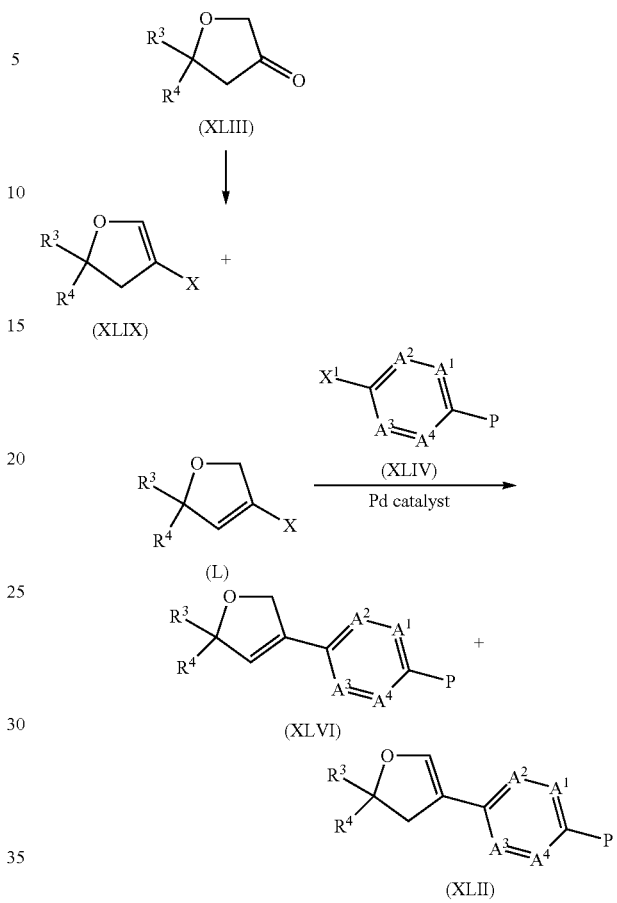

41) Compounds of formula (XLIII) can be prepared by hydrative cyclisation of a compound of formula (XLVIII) These reactions are usually carried out in the presence of a suitable lewis acid, such as a gold catalyst, as described in *J. Am. Chem. Soc.*, 2010, 132 (10), pp 3258-3259. The reaction is usually carried out using (Triphenylphosphine)gold(I) bis(trifluoromethanesulfonyl)imidate, in the presence of a pyridine N-oxide, such as 5-Bromo-1-oxy-nicotinic acid methyl ester and an acid, such as methanesulfonic acid, in an aprotic solvent, such as 1,2-dichloroethane. The reaction is carried out at a temperature of from 0° C. to 100° C., preferably from 0° C. to 40° C.

42) Compounds of formula (XLVIII) can be prepared by reacting a ketone of formula (XL) with a compound of formula (XLVII), where X is a halogen. These reactions are usually carried out in the presence of a metal, such as magnesium, lithium, indium, cerium or zinc, in a suitable solvent, such as tetrahydrofuran, diethyl ether or N, N-dimethylformamide. The reaction is carried out at a temperature of from −78° C. to 100° C., preferably from −78° C. to ambient temperature. Alternatively, compounds of formula (XLVIII) can be prepared by reacting a compound of formula (XL) with a compound of formula (XLVII), where X is a trialkylsilyl group. These reactions are usually carried out in the presence of strong base, such as lithium diisopropylamide, in a suitable solvent, such as tetrahydrofuran, diethyl ether or N, N-dimethylformamide. The reaction is carried out at a temperature of from −78° C. to 100° C., preferably from −78° C. to ambient temperature.

43) Compounds of formula (XLVI) (and compounds of formula (XLII)) can be prepared by reacting a compound of formula (L) (and respectively compounds of formula (XLIX)) wherein X is a leaving group, for example a halogen, such as bromo, or a triflate, with a compound of formula (XLIV) wherein $X^1$ is a boron derivative, such as a boronic acid, a pinacolboronate, or a trifluoroborate salt, in a Suzuki coupling reaction, in the presence of a palladium catalyst, such as palladium acetate or tetrakis(triphenylphosphine) palladium, in a suitable solvent, such as 1,4-dioxane, touene, acetonitrile or N, N-dimethylformamide. The reaction is carried out at a temperature of from −20° C. to 150° C., preferably from ambient temperature to 100° C. Alternatively, compounds of formula (XLVI) (and compounds of formula (XLII)) can be prepared by reacting a compound of formula (L) (and respectively compounds of formula (XLIX)) wherein X is a leaving group, for example a halogen, such as bromo, or a triflate with a compound of formula (XLIV) wherein $X^1$ is a trialkylstannane derivative, such as tributyltin, or respectively an organozinc derivative in a Stille or Negishi coupling reaction, in the presence of a palladium catalyst, such as palladium acetate or tetrakis (triphenylphosphine) palladium, in a suitable solvent, such as 1,4-dioxane, touene, acetonitrile or N, N-dimethylformamide.

44) Compounds of formula (XLIX) (and compounds of formula (L)) wherein X is a halogen, such as bromo, can be prepared by reacting a compound of formula (XLIII) with a brominating agent, such as phosphoric tribromide, in a suitable solvent, such as tetrahydrofuran, or chloroform, dichloromethane. The reaction is carried out at a temperature of from −40° C. to 100° C., preferably from −40° C. to ambient temperature. Alternatively, compounds of formula (XLIX) (and compounds of formula (L)) wherein X is a triflate, can be prepared by reacting a compound of formula (XLIII) with a triflating agent, such as triflic anhydride or N,N-bis(trifluoromethanesulfonyl)aniline, in the presence of a base, such as 4-picoline, sodium or potassium hexamethyldisilylamide, lithium diisopropylamide, triethylamine or 2,6-lutidine in a suitable solvent, such as tetrahydrofuran, chloroform or dichloromethane. The reaction is carried out at a temperature of from −100° C. to 150° C., preferably from −40° C. to 100° C.

formula (XIII) are commercially available or can be made by methods known to a person skilled in the art. Compounds of formula (LI) can be made by methods known to a person skilled in the art, as described in journal of Organic Chemistry (1981), 46(4), 771.

Scheme 17

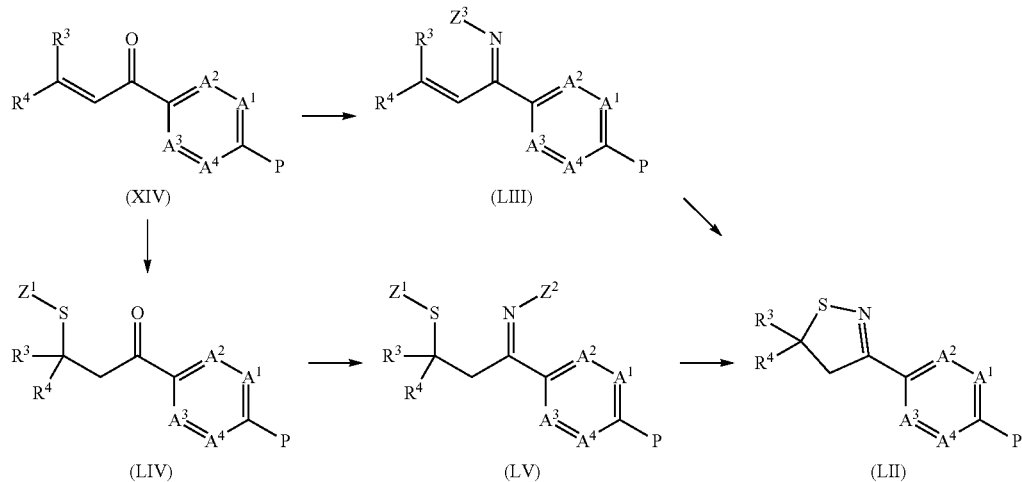

46) Compounds of formula (LIV) wherein $Z^1$ is hydrogen or cyano or halogen or $C_1$-$C_8$alkyl or aryl-$C_1$-$C_4$alkylene- or $C_1$-$C_8$alkylcarbonyl- or arylsulfonyl- or arylthio-, can be obtained by reacting an unsaturated ketone of formula (XIV), with a sulfur nucleophile, such as thioacetic acid, hydrogen sulfide, sodium sulfide, ammonium sulfide, thiourea, benzylmercaptan, Sodium benzenethiosulfonate, potassium thiocyanate, sodium thiocyanate, sodium thiomethoxide or tert-butyl mercaptan as shown on Scheme 17. Such reactions can be performed optionally in the presence of a base, such as sodium hydroxide, sodium ethoxide, sodium methoxide, sodium tert-butoxide or potassium hydroxide. Sometimes, such reactions can also be performed in the presence of an acid, for example p-toluenesulfonic acid, hydrochloric acid, acetic acid, in a solvent, such as methanol, ethanol, N,N-dimethylformamide, toluene, dichloromethane, ethyl acetate, acetonitrile or chlorobenzene or water, or mixtures thereof, at a temperature of from 0° C. to 100° C., preferably from ambient temperature to 80° C. Such conditions are described, for example, in Journal of the American Chemical Society (1949), 71, 3554-5 or in Tetrahedron: Asymmetry (2003), 14(1), 113-117 and Journal of Organic Chemistry (1996), 61, 1986.

47) Compounds of formula (LIII) wherein $Z^3$ is thiol or aryl substituted $C_1$-$C_8$alkylsulfinyl-, can be made by reaction of the ketone of formula (XIV) with an amine, such as triphenylmethanesulfenamide. Such reactions are usually carried out in the presence of an acid or not, for example p-toluenesulfonic acid, hydrochloric acid, acetic acid, optionally in the presence of a solvent, for example an alcohol, such as methanol or ethanol, or toluene, dichloromethane, water, or mixtures thereof. The reaction can be carried out in the presence or the absence of a dehydrating agent, such as anhydrous magnesium sulfate or molecular sieves. It can also be performed using a Dean Stark or Soxhlet apparatus that enables a constant removal of the water formed during the reaction. The reaction is carried out Scheme 16

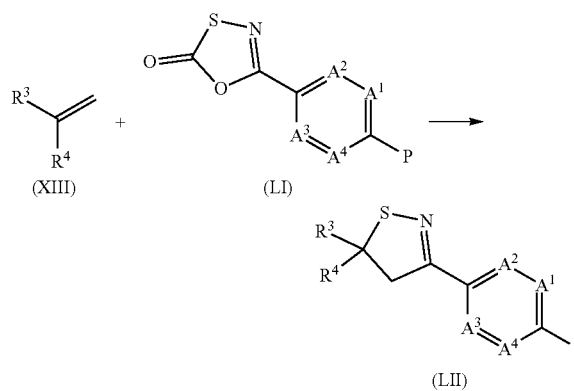

45) Compounds of formula (LII) can be prepared by reacting a compound of formula (LI) with the vinyl compound of formula (XIII) optionally in the presence of a suitable solvent, for example N,N-dimethylformamide, xylene, toluene, chlorobenzene or dichlorobenzene. The reaction can be performed under microwave heating preferably at temperatures up to 200° C. and preferably under neat conditions using a large excess of the compound of formula (XIII) (e.g. 40 equivalents). Vinyl compounds of at a temperature of from 0° C. to 100° C., preferably from 15° C. to 30° C., in particular at ambient temperature.

48) Compounds of formula (LV) wherein $Z^2$ is hydrogen or hydroxyl or $C_1$-$C_8$alkoxy- or $C_1$-$C_8$alkylsulfonyloxy- or $C_1$-$C_8$arylsulfonyloxy- or aryl-$C_1$-$C_4$alkylene- or aryl, can be made by reaction of the ketone of formula (LIV) with an amine, such as hydroxylamine hydrochloride, methoxylamine or ammonia. Such reactions are carried out in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. Such reactions can also be carried out in the presence of an acid or not, for example p-toluenesulfonic acid, hydrochloric acid, acetic acid, optionally in the presence of a solvent, for example an alcohol, such as methanol or ethanol, or toluene, dichloromethane, water, or mixtures thereof. The reaction can be carried out in the presence or the absence of a dehydrating agent, such as anhydrous magnesium sulfate or molecular sieves. It can also be performed using a Dean Stark or Soxhlet apparatus that enables a constant removal of the water formed during the reaction. The reaction is carried out at a temperature of from 0° C. to 100° C., preferably from 15° C. to 30° C., in particular at ambient temperature.

49) Compounds of formula (LII) can be obtained by cyclising a compound of formula (LIII) wherein $Z^3$ is thiol. Such reactions are usually carried out in the presence of an acid or not, for example p-toluenesulfonic acid, optionally in the presence of a solvent, for example dichloroethane, methanol, ethanol, toluene, dichloromethane or chlorobenzene. The reaction is carried out at a temperature of from 0° C. to 200° C., preferably from 25° C. to 100° C. Alternatively, compounds of formula (LII) can be obtained by cyclising a compound of formula (LIII) wherein $Z^3$ is aryl substituted $C_1$-$C_8$alkylsulfinyl-. Such reactions are usually carried out in the presence of an acid or not, for example p-toluenesulfonic acid, trifluoroacetic acid or hydrochloric acid, optionally in the presence of a solvent, for example dichloroethane, methanol, ethanol, toluene, dichloromethane or chlorobenzene. The reaction is carried out at a temperature of from 0° C. to 200° C., preferably from 25° C. to 100° C. Such reactions usually involve first the deprotection of the thiol to give a compound of formula (X) wherein $Z^3$ is thiol, followed by the cyclization.

50) Compounds of formula (LII) can be obtained from compound of formula (LV) wherein $Z^1$ is hydrogen or cyano or halogen or $C_1$-$C_8$alkyl or aryl-$C_1$-$C_4$alkylene- or $C_1$-$C_8$alkylcarbonyl- or arylsulfonyl- or arylthio-, and $Z^2$ is hydrogen or hydroxyl or $C_1$-$C_8$alkoxy- or $C_1$-$C_8$alkylsulfonyloxy- or $C_1$-$C_8$arylsulfonyloxy- or aryl-$C_1$-$C_4$alkylene- or aryl. Such reactions usually involve the deprotection of $Z^1$ and of $Z^2$ or of both groups. The reaction can then involve the following intermediates:

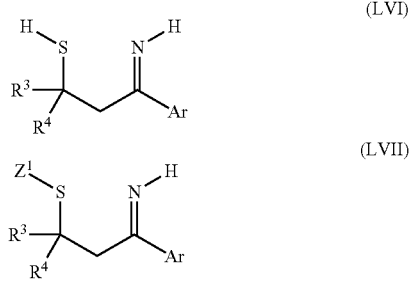

(LVI)

(LVII)

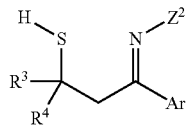

(LVIII)

Depending on the nature of $Z^1$ and $Z^2$, the deprotection conditions are different and can be made by methods known to a person skilled in the art or as described in T. W. Green, P. G. M. Wuts, *Protective Groups in Organic Synthesis*, Wiley-Interscience, New York, 1999, 564-566, 740-743.

51) Compounds of formula (LII) can be obtained from compound of formula (LVI) from an oxidation step. Such reactions are usually carried out in the presence of an oxidant, for example iodine, bromine, thionyl chloride, Bis(trifluoroacetoxy)iodobenzene; The reaction can be carried out in the presence of an acid or not, such as trifluoroacetic acid or acetic acid, optionally in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C. Such transformations, including reaction conditions and suitable catalyst, are described in Journal of the Chemical Society, Perkin Transactions 1: Organic and Bio-Organic Chemistry (1972-1999) (1985), (1), 153-7 and Organic Letters (2006), 8(21), 4811-4813. Similarly, compounds of formula (LII) can be obtained from a compound of formula (LVII) wherein $Z^1$ is arylsulfonyl- or arylthio-, by an oxidation step, are described in Journal of Organic Chemistry (1990), 55(13), 4156-62.

52) Compounds of formula (LII) can be obtained from compound of formula (LVIII) wherein $Z^2$ is $C_1$-$C_8$alkoxy-. Such reactions are usually carried out in the presence of a copper (I) reagent, such copper-3-methylsalicylate. The reaction can be carried out in the presence of a solvent, for example dichloroethane, dimethylsulfoxide, N,N-dimethylformamide, methanol, ethanol, toluene, dichloromethane, ethyl acetate or chlorobenzene. The reaction is carried out at a temperature of from 0° C. to 200° C., preferably from 25° C. to 100° C., or under microwave heating conditions. Such transformations are described in Journal of the American Chemical Society (2011), 133, 6403-6410.

53) Alternatively, compounds of formula (LII) can be obtained directly from a compound of formula (LVII) wherein $Z^1$ is hydrogen. Such reactions are usually carried out in the presence chloramines, formed in situ from ammonia and chlorine or sodium hypochlorite or hypochlorous acid, optionally in the presence of a solvent, for example dichloroethane, methanol, ethanol, toluene, dichloromethane or chlorobenzene. The reaction is carried out at a temperature of from −80° C. to 40° C., preferably below −40° C.

54) Alternatively, compounds of formula (LII) can be obtained directly from a compound of formula (LIV) wherein $Z^1$ is cyano or halogen or arylsulfonyl- or arylthio-. Such reactions are usually carried out in the presence ammonia, optionally in the presence of a solvent, for example dichloroethane, tetrahydrofuran, methanol, ethanol, toluene, dichloromethane or chlorobenzene. The reaction is carried out at a temperature of from −80° C. to 80° C.

55) Alternatively, compounds of formula (LII) can be obtained directly from a compound of formula (LIV) wherein $Z^1$ is aryl-$C_1$-$C_4$alkylene. Such reactions are usually carried out in two steps—The first one involves the treatment of a compound of formula (LIV) wherein $Z^1$ is aryl-$C_1$-$C_4$alkylene by a suitable oxidant, such as sulfuryl chloride or chlorine, in the presence of a solvent, for example dichloroethane, methanol, ethanol, toluene, dichloromethane or chlorobenzene, to provide a compound of formula (LIV) wherein $Z^1$ is chlorine. The second step then involves the treatment a compound of formula (LIV) wherein $Z^1$ is chlorine by an ammonia source, such as ammonia or ammonium bromide in the presence of a base, in the presence of a solvent, for example dichloroethane, methanol, ethanol, toluene, tetrahydrofuran, dichloromethane or chlorobenzene. Both steps are usually carried out at a temperature of from $-80°$ C. to $80°$ C.

56) Alternatively, compounds of formula (LII) can be obtained directly from a compound of formula (LIV) wherein $Z^1$ is hydrogen. Such reactions are usually carried out in the presence of a suitable nitrogen electrophile, such as Hydroxylamine-O-sulfonic acid. Such reactions are carried out in the presence of a base, for example an organic base, such as triethylamine or sodium acetate, or an inorganic base, such as sodium hydrogen carbonate, sodium hydroxide or potassium hydroxide optionally in the presence of a solvent, for example tetrahydrofuran, toluene, an alcohol, such as methanol or ethanol, or water, or mixtures thereof. The reaction is carried out at a temperature of from $-80°$ C. to $80°$ C.

by hydrolysis using a suitable base such as MOH, $M_2CO_3$, $MHCO_3$ wherein M is an alkali metal such as lithium, sodium, potassium, cesium, barium etc. or an alkoxide, or in the presence of acid, such as trifluoroacetic acid or hydrochloric acid, followed by decarboxylation by heating with or without a base. The reaction is carried out at a temperature of from $-20°$ C. to $200°$ C., in the presence or the absence of a suitable solvent.

57) Compounds of formula (LXIV) can be obtained from compounds of formula (LXIII) by subjecting then to a decarboxylative dehydration following the procedures known in literature.

58) Compounds of formula (LXIV) can also be obtained from compounds of formula (LX) via a two step sequence: first compounds of formula (LX) can be converted to the bicyclic intermediate of formula (LXIII) using with various activating agents like protic acids HCl, $H_2SO_4$, $H_3PO_4$ etc or Lewis acid such $BF_3.OEt_2$, or using dehydrating agents, such as MsCl, $Tf_2O$, $SOCl_2$, $(COCl)_2$ and $POCl_3$. Then, the compounds of formula (LXIII) can be transformed into the compounds of formula (LXIV) by heating to a temperature of from $30°$ C. to $150°$ C., in the presence or the absence of a suitable solvent.

59) Compounds of formula (LXI) can be obtained from compounds of formula (LX) by subjecting then to a dehydration following the procedures known in literature, using various activating agents like protic acids NCl, $H_2SO_4$, Scheme 18

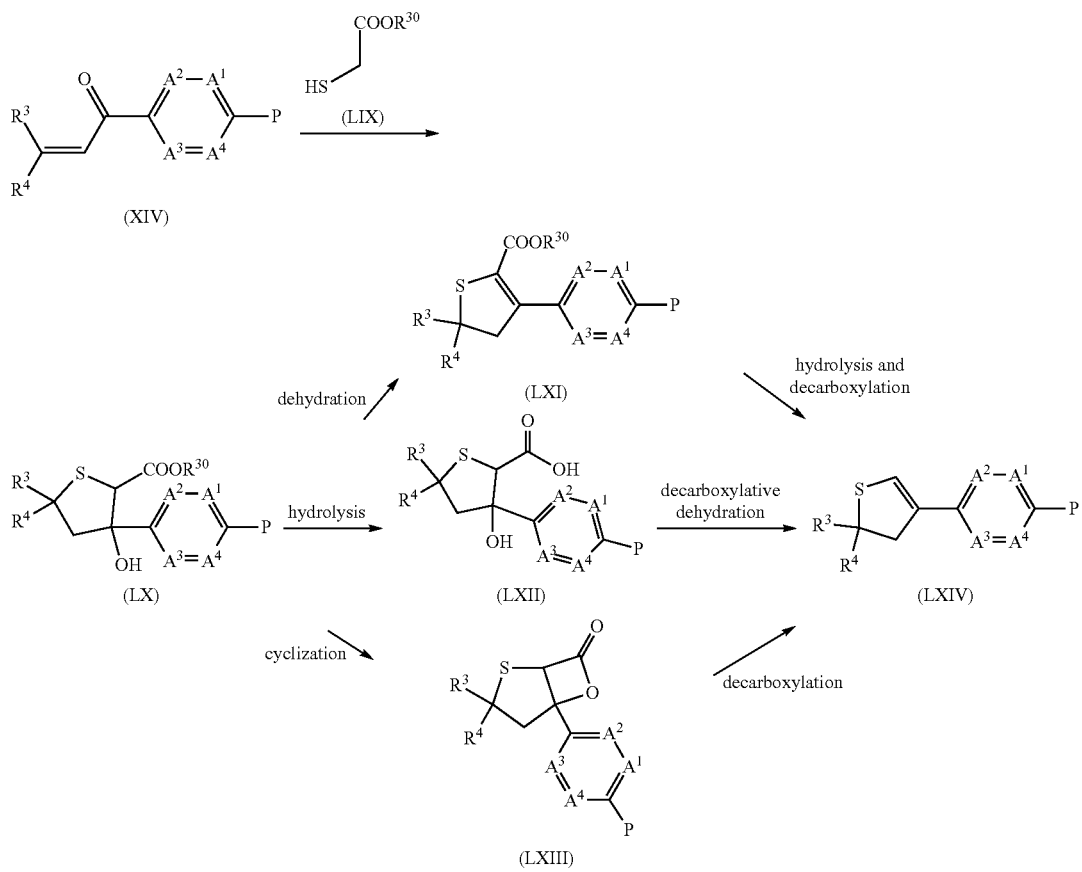

56) Compounds of formula (LXIV) can be obtained from compounds of formula (LXI), wherein $R^{30}$ is $C_1$-$C_{15}$alkyl, $H_3PO_4$ etc or Lewis acid such $BF_3.OEt_2$, or using dehydrating agents, such as MsCl, $Tf_2O$, $SOCl_2$, $(COCl)_2$ and $POCl_3$.

60) Compounds of formula (LX) can be obtained from compounds of formula (XIV) and compounds of formula (LIX) in presence or absence of bases such as MOH, $M_2CO_3$, $MHCO_3$ wherein M is an alkali metal such as lithium, sodium, potassium, cesium, barium etc. or an alkoxide, at a temperature of from −20° C. to 200° C.

Scheme 19

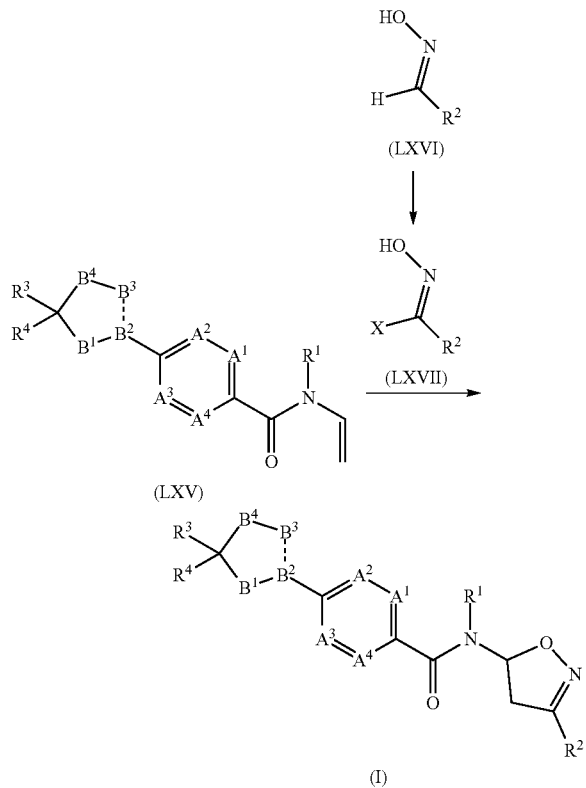

61) Compounds of formula (I) can be made by reaction of an oxime of formula (LXVII) and a vinyl compound of formula (LXV) in a two step reaction. In the first step, the oxime of formula (LXVI) is reacted with a halogenating agent, for example chlorine, or a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

In the second step, the halogeno hydroxy imine intermediate of formula (LXVII) is reacted with the vinyl compound of formula (LXV) in the presence of a base, for example an organic base, such as triethylamine, or an inorganic base, such as sodium hydrogen carbonate, in the presence of a suitable solvent, for example a polar solvent, such as N,N-dimethylformamide or isopropanol or an apolar solvent, such as toluene. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature. Vinyl compounds of formula (LXV) are easily prepared using methods known to a person skilled in the art, such as is described in WO2013120940.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

The compounds of formula (I) and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO200015615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula (I) according to the invention are preventively and/or curatively valuable active ingredients in the field of pest control, even at low rates of application, which have a very favorable biocidal spectrum and are well tolerated by warm-blooded species, fish and plants. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acalitus* spp, *Aculus* spp, *Acaricalus* spp, *Aceria* spp, *Acarus siro*, *Amblyomma* spp., *Argas* spp., *Boophius* spp., *Brevipalpus* spp., *Bryobia* spp, *Calipitrimerus* spp., *Chorioptes* spp., *Dermanyssus gallinae*, *Dermatophagoides* spp., *Eotetranychus* spp., *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,
*Haematopinus* spp., *Linognathus* spp., *Pediculus* spp., *Pemphigus* spp. and *Phylloxera* spp.;

from the order Coleoptera, for example,
*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,
*Aedes* spp., *Anopheles* spp, *Antherigona soccata*, *Bactrocea oleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,
*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopa-*

*phis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maid is, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp., *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp,

*Scirtothrips aurantii, Sericothrips variabilis, Taeniothrips* spp., *Thrips* spp;

from the order Thysanura, for example,

*Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., Alonsoa spp., Anemone spp., Anisodontea capsenisis, *Anthemis* spp., *Antirrhinum* spp., Aster spp., Begonia spp. (e.g. *B. elatior, B. semperflorens, B. tubéreux*), Bougainvillea spp., *Brachycome* spp., Brassica spp. (ornamental), Calceolaria spp., Capsicum annuum, Catharanthus roseus, Canna spp., *Centaurea* spp., *Chrysanthemum* spp., Cineraria spp. (*C. maritime*), Coreopsis spp., Crassula coccinea, Cupheaignea, *Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. oleracea, B.*

*pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), Mentha spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and *Ectoparasitic nematodes*), especially plant parasitic *nematodes* such as root knot *nematodes, Meloidogyne hapla, Meloidogyne incognita, Meloidogyne javanica, Meloidogyne arenaria* and other *Meloidogyne* species; cyst-forming *nematodes, Globodera rostochiensis* and other *Globodera* species; *Heterodera avenae, Heterodera glycines, Heterodera schachtii, Heterodera trifolii*, and other *Heterodera* species; Seed gall *nematodes, Anguina* species; Stem and foliar *nematodes, Aphelenchoides* species; Sting *nematodes, Belonolaimus longicaudatus* and other *Belonolaimus* species; Pine *nematodes, Bursaphelenchus xylophilus* and other *Bursaphelenchus* species; Ring *nematodes, Criconema* species, *Criconemella* species, *Criconemoides* species, *Mesocriconema* species; Stem and bulb *nematodes, Ditylenchus destructor, Ditylenchus dipsaci* and other *Ditylenchus* species; Awl *nematodes, Dolichodorus* species; Spiral *nematodes, Heliocotylenchus multicinctus* and other *Helicotylenchus* species; Sheath and sheathoid *nematodes, Hemicycliophora* species and *Hemicriconemoides* species; *Hirshmanniella* species; Lance *nematodes, Hoploaimus* species; false rootknot *nematodes, Nacobbus* species; Needle *nematodes, Longidorus elongatus* and other *Longidorus* species; Pin *nematodes, Pratylenchus* species; Lesion *nematodes, Pratylenchus neglectus, Pratylenchus penetrans, Pratylenchus curvitatus, Pratylenchus goodeyi* and other *Pratylenchus* species; Burrowing *nematodes, Radopholus similis* and other *Radopholus* species; Reniform *nematodes, Rotylenchus robustus, Rotylenchus reniformis* and other *Rotylenchus* species; *Scutellonema* species; Stubby root *nematodes, Trichodorus primitivus* and other *Trichodorus* species, *Paratrichodorus* species; Stunt *nematodes, Tylenchorhynchus claytoni, Tylenchorhynchus dubius* and other *Tylenchorhynchus* species; Citrus *nematodes, Tylenchulus* species; Dagger *nematodes, Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, *Ampullariidae; Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); Discus (*D. rotundatus*); Euomphalia; *Galba* (*G. trunculata*); *Helicelia* (*H. itala, H. obvia*); *Helicidae Helicigona arbustorum*); *Helicodiscus; Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); *Vallonia* and *Zanitoides*.

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising *nematodes*, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/).

In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO2008151984, WO2003034823, U.S. Pat. No. 5,631,072, WO2005064072, WO2006128870, EP1724392, WO2005113886 or WO2007090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against wood borers listed in the following tables X and Y:

TABLE X

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE Y

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticoillis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain- |

TABLE Y-continued

Examples of native woodborers of economic importance.

| Family | Species | Host or Crop Infested |
|---|---|---|
| | *Vitacea polistiformis* | ash, Viburnum, Willow, Apple, Loquat, Ninebark, Bayberry Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., Panstrongylus spp.

Of the order Blattarida, for example *Blatta orientalis, Periplaneta americana, Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharine*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
| --- | --- |
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| active ingredient | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| active ingredient | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| active ingredient | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| active ingredient | 40% |
| --- | --- |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredient | 40% |
| --- | --- |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |

| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula (I) with active ingredients are preferred (the abbreviation "TX" means "one compound selected from the group consisting of the compounds described in Tables 1 to 128 (including 1a to 128a to 1m to 128m) and Table P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX,

*Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure B2 (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, niflurdide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin

[84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-

5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7] TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7] TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-C5-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-C5-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX,1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; lancotrione [1486617-21-3]+TX; florpyrauxifen [943832-81-3]+TX; ipfentrifluconazole [1417782-08-1]+TX; mefentrifluconazole [1417782-03-6]+TX; quinofumelin [861647-84-9]+TX; chloroprallethrin [399572-87-3]+TX; cyhalodiamide [1262605-53-7]+TX; fluazaindolizine [1254304-22-7]+TX; fluxametamide [928783-29-3]+TX; epsilon-metofluthrin [240494-71-7]+TX; epsilon-momfluorothrin [1065124-65-3]+TX; pydiflumetofen [1228284-64-7]+TX; kappa-bifenthrin [439680-76-9]+TX; broflanilide [1207727-04-5]+TX; dicloromezotiaz [1263629-39-5]+TX; dipymetitrone [16114-35-5]+TX; pyraziflumid [942515-63-1]+TX; and kappa-tefluthrin [391634-71-2]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter cysts* (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX,

*Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* CrylAb+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/35 Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar nucleopolyhedrosis* virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan $C_9$-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia* onychis+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas* reactans+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dorman+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodo-* torula rubra+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis nucleopolyhedrovirus* (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, Chrysanthemum extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaC20)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomata C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomata-PC)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX, 11 Tetradecatrienyl acetate+TX, (Z+TX,Z+TX, E)-7+TX, 11+TX, 13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, *Andersoni*-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exo-*

*chomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopfi* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Callego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (SD-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline Y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from Tables 1 to 128 (including Tables 1a to 128a to 1m to 128m) and Table A of the present invention with active ingredients described above comprises a compound selected from Tables 1 to 128 (including Tables 1a to 128a to 1m to 128m) and Table A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from Tables 1 to 128 (including Tables 1a to 128a to 1m to 128m) and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Tables 1 to 128 (including Tables 1a to 128a to 1m to 128m) and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula (I). The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

The invention further relates to a method for controlling pests, which comprises applying a composition according to the invention to the pests or their environment preferably with the exception of a method for treatment of the human or animal body by surgery or therapy and diagnostic methods practised on the human or animal body.

The invention further relates to a method for the protection of plant propagation material from the attack by pests, which comprises treating the propagation material or the site, where the propagation material is planted, with a composition comprising a compound according to this invention or with a compound according to this invention. The invention further relates to a plant propagation material treated with the pesticidal composition comprising a compound according to this invention or with a compound according to this invention.

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm, 0.4 ppm, 0.2 ppm, 0.1 ppm or even at lower concentrations. Temperatures are given in degrees Celsius; mixing ratios of solvents are given in parts by volume.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated.

The following LC-MS methods were used to characterize the compounds:

Method A

MS Spectra were recorded on a Waters SQD2 Mass Spectrometer (Single quadrupole mass spectrometer) Ionisation method: Electrospray, Polarity: positive ions
Capillary (kV) 3.50, Cone (V) 30.00, Extractor (V) 3.00, Source Temperature (° C.) 150, Desolvation Temperature (° C.) 400 Cone Gas Flow (L/Hr) 60, Desolvation Gas Flow (L/Hr) 700, Mass range: 140 to 800 Da; DAD Wavelength range (nm): 210 to 400
LC Method Waters ACQUITY UPLC with the following HPLC gradient conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method B

Spectra were recorded on a Mass Spectrometer (ACQUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75

Example 1

Step A: methyl 2-[(4S)-4-hydroxyisoxazolidine-2-carbonyl]benzoate

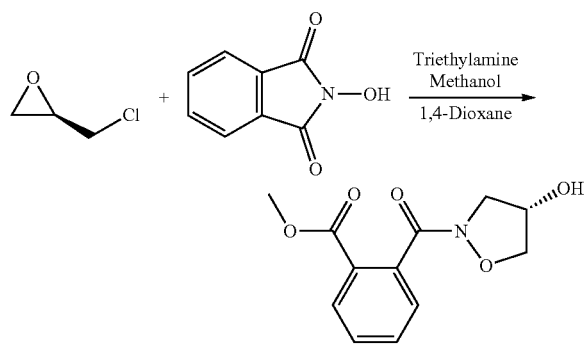

In a sulfonation flask with mechanical stirrer, condenser, thermometer, under inert atmosphere, a suspension of N-hydroxyphthalimide (40.0 g) and (R)-(−)-epichlorhydrin (25.0 g) in anhydrous 1,4-dioxane (240 mL), was treated with triethylamine (3.42 mL). The suspension turned immediately orange. The resulting mixture was then heated to 55° C. and stirred at that temperature for 6 days. To the resulting dark red solution were added methanol (240 mL) and triethylamine (34.2 mL) and the stirring was continued for 3 hours at the same temperature.

The reaction mixture was then concentrated under vacuum to yield a dark red oil which was treated with a little dichloromethane and saturated aqueous sodium bicarbonate solution. The mixture was extracted twice with dichloromethane. The organic phase was dried over sodium sulfate and evaporated under reduced pressure. The residue was submitted to silica gel chromatography, using methanol/dichloromethane 5:95 as eluent. The selected fractions were evaporated and the residue was triturated with ethyl acetate. A white suspension formed slowly. Methyl 2-[(4S)-4-hydroxyisoxazolidine-2-carbonyl]benzoate was isolated by filtration.

$^1$HNMR (CDCl$_3$, 400 MHz): 7.99 (d, J=8 Hz, 1H), 7.62 (t, J=8 Hz, 1H), 7.51-7.42 (m, 2H), 4.81-4.72 (m, 1H), 4.35-3.63 (m, 4H), 3.92 (s, 3H).

Step B: (4S)-isoxazolidin-2-ium-4-ol Chloride

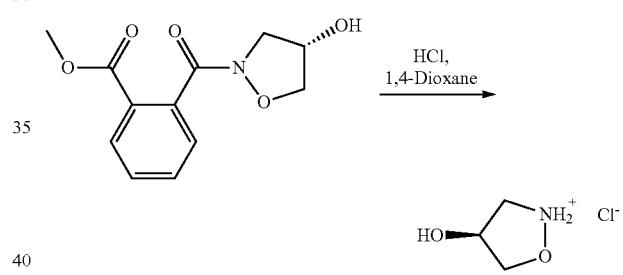

Methyl 2-[(4S)-4-hydroxyisoxazolidine-2-carbonyl]benzoate (264 g) was placed in a flask equipped with a mechanical stirrer, a condenser, a thermometer and an inert gas inlet and outlet through a bubbler. A 4 molar anhydrous solution of hydrochloric acid in dioxane (1.313 L) was added. The resulting solution was stirred at 80° C. for 20 hours. Care was taken to trap the hydrochloric gas leaving the apparatus.

The reaction mixture was then cooled to 0° C. and the solid that was formed was isolated by careful filtration. After rinsing with dry dioxane and drying, (4S)-isoxazolidin-2-ium-4-ol chloride was isolated as colorless powder. The compound was analyzed by NMR.

$^1$H-NMR (DMSO-d6, 400 MHz): 13.1-12.1 (br s, 2H), 6.2-5.2 (br s, 1H), 4.85-4.77 (m, 1H), 4.08 (d, 1H), 4.04 (dd, 1H), 3.49 (dd, 1H), 3.33 (d, 1H).

Step C: tert-butyl (4S)-4-hydroxyisoxazolidine-2-carboxylate

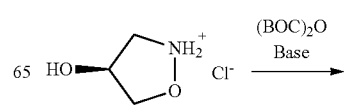

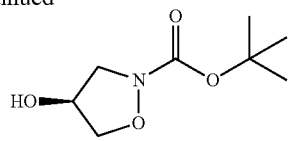

A suspension of (4S)-isoxazolidin-2-ium-4-ol chloride (67.8 g) in dry tetrahydrofuran (300 mL) under inert atmosphere was stirred at 0° C. A solution of triethylamine (82 g) in tetrahydrofuran (100 mL) was added over a period of 10 minutes. A solution di-tert-butyl dicarbonate (141 g) in tetrahydrofuran (100 mL) was then added to the reaction mixture. After the removal of the ice bath, the reaction mixture was stirred at room temperature until the strating material was reacted.

The progression of the reaction is monitored by TLC analysis of aliquots eluted on a silica gel plate with a mixture of ethyl acetate/heptane 1:1. The plate can be developed with iodine vapour or ninhydrine.

The reaction mixture was the filtered and the precipitate washed with tetrahydrofuran. The filtrate was concentrated under vacuum and the residue was purified on a silica gel column using first a gradient heptane/ethyl acetate 3:1 to 1:3.

The tert-butyl (4S)-4-hydroxyisoxazolidine-2-carboxylate is isolated as a pale yellow oil, characterized by its NMR spectrum.

$^1$HNMR (CDCl$_3$, 400 MHz): 4.78-4.74 (m, 1H), 3.96-3.94 (m, 2H), 3.72-3.68 (m, 2H), 2.36 (broad d, 1H), 1.48 (s, 9H).

Step D: tert-butyl (4S)-4-methylsulfonyloxyisoxazolidine-2-carboxylate

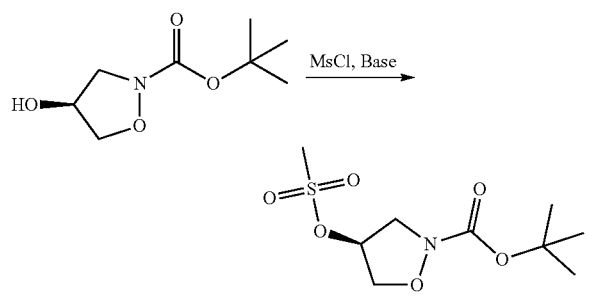

To a solution of tert-butyl (4S)-4-hydroxyisoxazolidine-2-carboxylate (5.00 g) in dichloromethane (30 mL) was added triethylamine (7.52 mL). The reaction flask was cooled in an ice bath and a solution of methanesulfonyl chloride (3.13 mL) in dichloromethane (10 mL) was slowly added in such a way to keep the temperature below 20° C. The resulting orange colored suspension was stirred for 16 hours at 20° C. and resulted in a brown suspension.

The reaction mixture was then washed with 1M aqueous hydrochloric acid (30 mL) and the aqueous phase was extracted with dichloromethane. The combined organic extracts were washed with 1M aqueous sodium hydroxide (30 mL). The aqueous phase was extracted with dichloromethane and the combined organic extracts were dried over sodium sulfate and concentrated under vacuo to yield crude tert-butyl (4S)-4-methylsulfonyloxyisoxazolidine-2-carboxylate that was pure enough to be used in the following step.

$^1$HNMR (CDCl$_3$, 400 MHz): 5.53-5.47 (m, 1H), 4.20-4.15 (broad d, J=10 Hz, 1H), 4.11-4.05 (dd, J$_1$=10 Hz, J$_2$=5 Hz, 1H), 4.03-3.97 (broad d, J=14 Hz, 1H), 3.89-3.82 (dd, J$_1$=14 Hz, J$_2$=5 Hz, 1H), 3.07 (s, 3H), 1.50 (s, 9H).

Step E: tert-butyl (4R)-4-azidoisoxazolidine-2-carboxylate

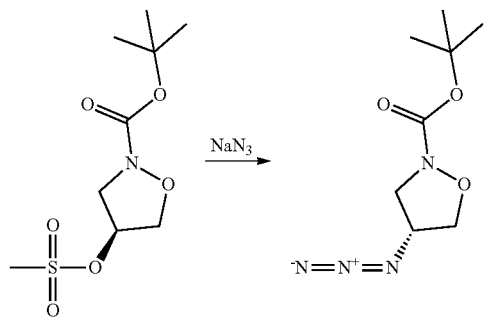

Sodium azide (21.5 g) was suspended in 170 mL of dimethylformamide (dried over molecular sieves) in a 500 mL flask fitted with a mechanical stirrer, a thermometer, a condenser, an argon inlet and outlet with a bubbler and a dropping funnel. The reaction flask was placed in an oil bath and heated under stirring at 60° C. The reaction was performed under argon atmosphere and behind a safety shield. Special care was given to the absence of chlorinated solvent traces in the starting mesylate for safety reasons. A solution of tert-butyl (4S)-4-methylsulfonyloxyisoxazolidine-2-carboxylate (described above) (68 g) in dry dimethylformamide (170 mL) was added under stirring. No exotherm was observed. After the addition was complete, the reaction mixture was stirred at the same temperature for 22 hours. The progression of the reaction can be followed by TLC analysis (silica gel plate, eluent ethyl acetate-heptane 1:1, Rf starting material 0.3, Rf product 0.6).

The reaction mixture was then let cool down to room temperature and transferred in a mixture of water (1 L) and ethyl acetate. The resulting mixture was extracted three times with ethyl acetate. The combined organic extracts were washed three times with water, then with brine before being dried over sodium sulfate. After removal of the solvent under vacuum, the crude tert-butyl (4R)-4-azidoisoxazolidine-2-carboxylate was obtained as a light orange oil. It was used without purification for the following step.

$^1$HNMR (CDCl$_3$, 400 MHz): 4.47-4.42 (m, 1H), 4.07-4.01 (dd, 1H), 3.97-3.92 (dd, 1H), 3.80-3.77 (d, 2H), 1.51 (s, 9H).

Step F: tert-butyl (4R)-4-aminoisoxazolidine-2-carboxylate

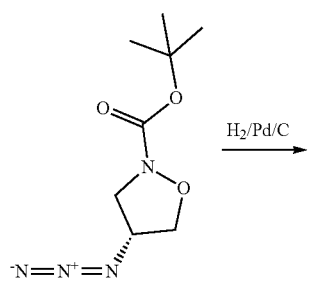

-continued

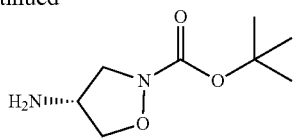

A solution of tert-butyl (4R)-4-azidoisoxazolidine-2-carboxylate (56 g) in tetrahydrufurane (1300 mL) was placed in an inertized autoclave equipped with a mechanical stirrer. Palladium on carbon (2.50 g, 5% catalyst loading) was introduced and the reactor was closed. After evacuation of the reactor's atmosphere hydrogen was introduced (this operation was repeated twice). The applied pressure didn't exceed 3 atm. The reaction was performed under strong agitation, at room temperature. The progression was checked by analysis of aliquots of the reaction mixture (after removal of hydrogen under vacuum and filling the reactor with argon). After 8 hours, another portion of catalyst (1.25 g) was introduced, following a safe protocol and the hydrogenation was continued for two more hours, after which the conversion was complete. After inertizing the reactor, the reaction mixture was filtered over a short path of celite and the filtrate was evaporated on the rotary evaporator at 60° C. The crude tert-butyl (4R)-4-aminoisoxazolidine-2-carboxylate was obtained as a pale brown oil.

$^1$HNMR (CDCl$_3$, 400 MHz): 4.00-3.89 (m, 2H), 3.87-3.80 (dd, 1H), 3.70-3.65 (dd, 1H), 3.38-3.33 (dd, 1H), 1.48 (s, 9H).

Enantiomeric purity of tert-butyl (4R)-4-aminoisoxazolidine-2-carboxylate: Chiral analysis of the product was performed on a chiral HPLC, using a racemic compound as reference.

HPLC: Waters UPLC—HClass
DAD Detector Waters UPLC
Column: Daicel CHIRALPAK® IF, 3 µm, 0.46 cm×10 cm
Mobile phase: Heptane/EtOH/DEA 80/20/0.1%
Flow rate: 1.0 ml/min
Detection: 220 nm
Sample concentration: 1 mg/mL in iPrOH 100%
Injection: 24

Under these conditions, the enantiomers have a retention time of 5.99 min and 9.69 min respectively.

The product obtained as described above showed only the peak of the short retention time, the other isomer being not detected.

Example 2

Step A: [(4S)-2-(dimethylsulfamoyl)isoxazolidin-4-yl] methanesulfonate

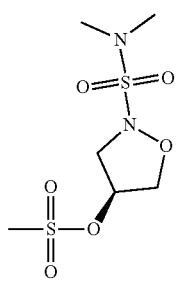 [SMILES: CN(C)S(=O)(=O)N1C[C@H](OS(C)(=O)=O)CO1]

To a suspension of (4S)-isoxazolidin-2-ium-4-ol chloride (synthesis described in step B of example 1) (5.00 g) in tetrahydrofuran (50 mL) under inert atmosphere was added triethylamine (19.6 mL). The mixture was stirred at 20° C. for 15 minutes, then N,N-dimethylsulfamoyl chloride (4.75 mL) was added. The reaction mixture was then heated to 60° C. and stirred for 20 hours.

The resulting suspension was then cooled down to 0° C. and methanesulfonyl chloride (3.42 mL) was added dropwise, so that the temperature was kept under 30° C. The mixture was then stirred at 20° C. for 2 hours. The reaction mixture was treated with water (150 mL) and extracted three times with ethyl acetate. The combined organic phases were washed with a saturated aqueous solution of sodium bicarbonate, followed by brine and dried over sodium sulfate. After removal of the solvent, the pale brown oil was crystallized from ethyl acetate/hexanes to yield off-white crystals of the title product that was characterized by NMR.

$^1$HNMR (CDCl$_3$, 400 MHz): 5.67-5.58 (m, 1H), 4.50 (dd, J$_1$=10.4 Hz, J$_2$=6.2 Hz, 1H), 4.24 (dd, J$_1$=10.4 Hz, J$_2$=2.6 Hz, 1H), 4.15 (dd, J$_1$=14.3 Hz, J$_2$=6.2 Hz, 1H), 3.71 (dd, J$_1$=14.3 Hz, J$_2$=2.6 Hz, 1H), 3.10 (s, 3H), 2.96 (s, 3H).

Steps B then C: (4R)-4-amino-N,N-dimethyl-isoxazolidine-2-sulfonamide

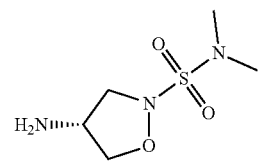

The title compound was obtained in an analogous way as described in steps E and F of synthesis example 1. It was characterized by NMR analysis.

$^1$HNMR (CDCl$_3$, 400 MHz): 4.25 (t, 1H), 4.07-3.99 (m, 1H), 3.79 (dd, 1H), 3.73 (dd, 1H), 3.25 (dd, 1H), 2.89 (s, 6H).

Example 3: Step A: [(4S)-2-ethylsulfonylisoxazolidin-4-yl] ethanesulfonate

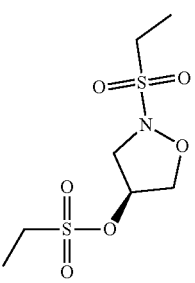 [SMILES: CCS(=O)(=O)O[C@@H]1CON(S(=O)(=O)CC)C1]

To a stirred suspension of (4S)-isoxazolidin-2-ium-4-ol chloride (synthesis described in step B of example 1) (2.50 g) in dichloromethane (100 mL) at 0° C. was added triethylamine (11.2 mL), whereby the reaction mixture became a yellow solution. Ethanesulfonyl chloride (6.53 g) was then added in such a way that the temperature didn't exceed 25°

C. A suspension formed and the reaction mixture was stirred at 0° C. for 30 min, then for 1 hour at 20° C.

The reaction mixture was then washed with hydrochloric acid aqueous solution (1 N), followed by water and brine. After drying of the organic phase over sodium sulfate and removal of the solvent, the dark brown oil was purified by chromatography over a silica gel, eluting with a mixture of heptane and ethyl acetate. The title compound was isolated as a brown oil and characterized by NMR.

$^1$HNMR (CDCl$_3$, 400 MHz): 5.65-5.59 (m, 1H), 4.47 (dd, 1H), 4.37 (dd, 1H), 4.21 (dd, 1H), 3.72 (dd, 1H), 3.42-3.34 (m, 2H), 3.22 (q, 2H), 1.47-1.38 (m, 6H).

Step B: (4R)-4-azido-2-ethylsulfonyl-isoxazolidine

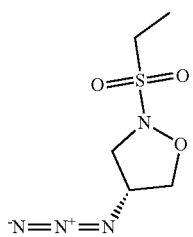

In a similar way as described above, but with heating at 90° C., the title compound was obtained as a pale yellow oil.

$^1$HNMR (CDCl$_3$, 400 MHz): 4.63-4.55 (m, 1H), 4.41 (dd, 1H), 4.21 (dd, 1H), 4.04 (dd, 1H), 3.45-3.20 (m, 3H), 1.44 (t, 3H).

Step C: (4R)-2-ethylsulfonylisoxazolidin-4-amine

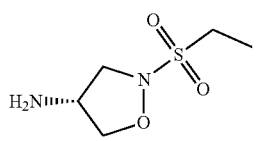

In a similar way as described above, the title compound was obtained as a colorless oil.

$^1$HNMR (CDCl$_3$, 400 MHz): 4.31 (dd, 1H), 4.14-4.06 (m, 1H), 3.90 (dd, 1H), 3.82 (dd, 1H), 3.38-3.25 (m, 3H), 1.60 (br. S, 2H), 1.42 (t, 3H).

Example 4:
(4R)-2-methylsulfonylisoxazolidin-4-Amine, Hereafter, was Also Prepared

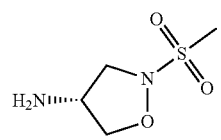

By analogy to the above described examples, the title compound was also prepared as a light yellow oil.

$^1$HNMR (CDCl$_3$, 400 MHz): 4.34 (dd, 1H), 4.13-4.07 (m, 1H), 3.88 (dd, 1H), 3.84 (dd, 1H), 3.34 (dd, 1H), 3.12 (s, 3H), 1.56 (br. s, 2H).

Example 5

Step A: tert-butyl 4-[(4-acetyl-2-methyl-benzoyl) amino]isoxazolidine-2-carboxylate

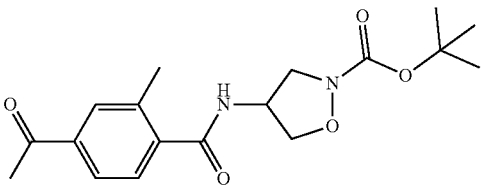 [SMILES: CC(=O)c1ccc(C(=O)NC2CON(C(=O)OC(C)(C)C)C2)c(C)c1]

To a solution of 4-acetyl-2-methyl-benzoyl chloride (5.00 g) in acetonitrile was added tert-butyl 4-aminoisoxazolidine-2-carboxylate (5.55 g) (preparation described above) and pyridine (2.4 g) at 20° C. After stirring for 15 hours, the reaction mixture was diluted with ethyl acetate and washed with diluted aqueous hydrochloric acid, then sodium hydrogen carbonate solution, water and brine. The organic phase was dried over sodium sulfate and the solvent removed at the rotary evaporator. The crude product was purified by chromatography over silica gel, eluting with mixtures of cyclohexane ethyl acetate. The title product was isolated as a viscous oil.

$^1$HNMR (CDCl$_3$, 400 MHz): 7.76 (s, 1H), 7.72 (d, 2H), 7.39 (d, 1H), 6.58 (br. d, 1H), 5.05-4.96 (m, 1H), 4.10-4.02 (m, 2H), 3.97 (dd, 1H), 3.60 (dd, 1H), 2.58 (s, 3H), 2.45 (s, 3H), 1.47 (s, 9H).

Example 6

Step A: 4-acetyl-2-methyl-N-(2-methylsulfonylisoxazolidin-4-yl)benzamide

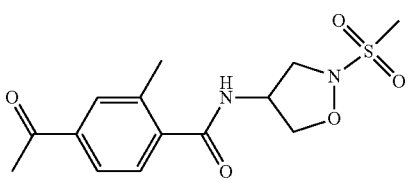 [SMILES: CC(=O)c1ccc(C(=O)NC2CON(S(C)(=O)=O)C2)c(C)c1]

Treatment of a solution of 4-acetyl-2-methyl-benzoyl chloride with 2-methylsulfonylisoxazolidin-4-amine lead to the title compound as colorless crystals with a melting point of 153-155° C.

$^1$HNMR (CDCl$_3$, 400 MHz): 7.80-7.73 (m, 2H), 7.44 (d, 1H), 6.94 (br. d, 1H), 5.37-5.29 (m, 1H), 4.48 (t, 1H), 4.18 (dd, 1H), 3.96 (d, 1H), 3.71 (dd, 1H), 3.17 (s, 3H), 2.60 (s, 3H), 2.48 (s, 3H).

Step B: 4-[(E-Z)-3-(3,5-dichlorophenyl)-4,4,4-trifluoro-but-2-enoyl]-2-methyl-N-(2-methylsulfonylisoxazolidin-4-yl)benzamide

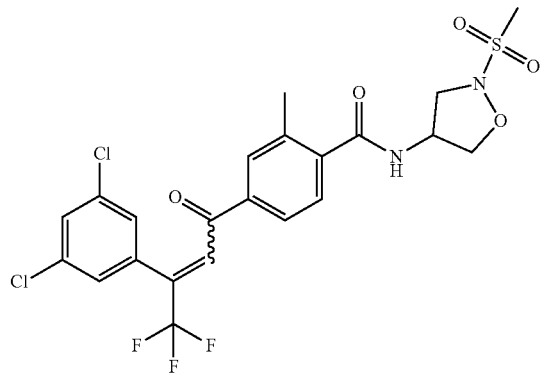

4-Acetyl-2-methyl-N-(2-methylsulfonylisoxazolidin-4-yl)benzamide (3.00 g), 1-(3,5-dichlorophenyl)-2,2,2-trifluoro-ethanone (3.35 g) and potassium carbonate (3.18 g) were mixed in tetrahydrofuran (50 mL). The suspension was stirred at 65° C. for 44 hours.

The resulting mixture was diluted with water (200 mL) and 2N hydrochloric acid (25 mL), then extracted twice with ethyl acetate. The organic phase was washed with water, brine and dried over sodium sulfate. After evaporation of the solvent, the crude product was submitted to chromatography over silica gel.

$^1$HNMR (CDCl$_3$, 400 MHz): 7.68-7.63 (m, 2H), 7.45 (d, 1H), 7.35 (d, 1H), 7.14 (s, 2H), 6.90 (br.d, 1H), 5.38-5.28 (m, 1H), 4.50 (t, 1H), 4.20 (dd, 1H), 4.01-3.95 (m, 1H), 3.68 (dd, 1H), 3.18 (s, 3H), 2.48 (s, 3H).

Example 7: Method for Preparing Compounds of the Invention from a Carboxylic Acid

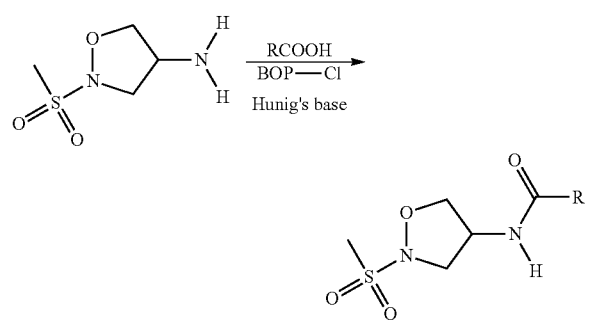

To a solution of an acid of formula RCOOH (45 μmol) in dimethylacetamide (0.3 ml) was added successively a solution of 2-methylsulfonylisoxazolidin-4-amine (30 μmol) in dimethylacetamide (0.25 ml), diisopropylethylamine (Hunig's base) (0.6 ml), and a solution of bis(2-oxo-3-oxazolidinyl)phosphonic chloride ("BOP-Cl") (15.3 mg) in dimethylacetamide (0.25 ml). The reaction mixture was stirred at 50° C. for 16 hours. Then the reaction mixture was evaporated to dryness. The remaining mixture was dissolved with methanol/dimethylacetamide (4:1) (0.7 ml) and purified by preparative HPLC. This method was used to prepare a number of compounds (Compound Nos. A1 to A8 of Table A) in parallel.

The corresponding carboxylic acids used for the preparation of Compounds A1 to A8 are respectively described in the following patent applications (WO 2014072480, WO 2013037626, WO 2013026724, WO 2010020522, WO 2010149506, WO 2012156400, WO 2012045700, WO 2010149506).

TABLE A

Compounds according to the invention

| Compound number | chemical name | LC-MS Method | RT (min) | [M + H]$^+$ measured |
|---|---|---|---|---|
| A1 | 2-chloro-N-(2-methylsulfonylisoxazolidin-4-yl)-4-[2-(3,4,5-trichlorophenyl)-2-(trifluoromethyl)-3H-thiophen-4-yl]benzamide | A | 2.09 | 635.0 |
| A2 | 4-[(5S)-5-(3,5-dichlorophenyl)-5-(trifluoromethyl)-4H-isothiazol-3-yl]-2-methyl-N-(2-methylsulfonylisoxazolidin-4-yl)benzamide | A | 1.98 | 582.1 |
| A3 | 4-[2-(3,5-dichlorophenyl)-2-(trifluoromethyl)-3H-furan-4-yl]-2-methyl-N-(2-methylsulfonylisoxazolidin-4-yl)benzamide | A | 1.95 | 565.1 |
| A4 | 4-[(4S,5R)-4-chloro-5-(3,5-dichlorophenyl)-5-(trifluoromethyl)-4H-isoxazol-3-yl]-2-methyl-N-(2-methylsulfonylisoxazolidin-4-yl)benzamide | A | 1.97 | 600.1 |
| A5 | 4-[3-(3,5-dichlorophenyl)-3-(trifluoromethyl)-2,4-dihydropyrrol-5-yl]-2-methyl-N-(2-methylsulfonylisoxazolidin-4-yl)benzamide | A | 1.76 | 564.1 |
| A6 | 4-[3-(3,5-dichlorophenyl)-3-(trifluoromethyppyrrolidin-1-yl]-2-methyl-N-(2-methylsulfonylisoxazolidin-4-yl)benzamide | A | 1.89 | 566.1 |
| A7 | 4-[3-(3,5-dichloro-4-fluoro-phenyl)-3-(trifluoromethyl)-2,4-dihydropyrrol-5-yl]-2-methyl-N-(2-methylsulfonylisoxazolidin-4-yl)benzamide | A | 1.77 | 582.1 |
| A8 | 2-methyl-N-(2-methylsulfonylisoxazolidin-4-yl)-4-[3-(3,4,5-trichlorophenyl)-3-(trifluoromethyl)-2,4-dihydropyrrol-5-yl]benzamide | A | 1.86 | 598.1 |
| A9 | 4-[3-(3,5-dichlorophenyl)-3-(trifluoromethyppyrrolidin-1-yl]-N-[(4R)-2-(dimethylsulfamoyl)isoxazolidin-4-yl]-2-methyl-benzamide | B | 2.00 | 594.11 |
| A10 | 4-[3-(3,5-dichloro-4-fluoro-phenyl)-3-(trifluoromethyl)-2,4-dihydropyrrol-5-yl]-N-[(4R)-2-(dimethylsulfamoyl)isoxazolidin-4-yl]-2-methyl-benzamide | B | 1.88 | 610.08 |
| A11 | N-[(4R)-2-(dimethylsulfamoypisoxazolidin-4-yl]-2-methyl-4-[3-(3,4,5-trichlorophenyl)-3-(trifluoromethyl)-2,4-dihydropyrrol-5-yl]benzamide | B | 1.97 | 626.05 |
| A12 | 4-[2-(3,5-dichlorophenyl)-2-(trifluoromethyl)-3H-furan-4-yl]-N-[(4R)-2-(dimethylsulfamoyl)isoxazolidin-4-yl]-2-methyl-benzamide | B | 2.06 | 593.08 |

TABLE A-continued

Compounds according to the invention

| Compound number | chemical name | LC-MS Method | RT (min) | [M + H]+ measured |
|---|---|---|---|---|
| A13 | 4-[(5S)-5-(3,5-dichlorophenyl)-5-(trifluoromethyl)-4H-isothiazol-3-yl]-N-[(4R)-2-(dimethylsulfamoyl)isoxazolidin-4-yl]-2-methyl-benzamide | B | 2.08 | 610.05 |
| A14 | 4-[3-(3,5-dichlorophenyl)-3-(trifluoromethyl)-2,4-dihydropyrrol-5-yl]-N-[(4R)-2-(dimethylsulfamoyl)isoxazolidin-4-yl]-2-methyl-benzamide | B | 1.87 | 592.09 |
| A15 | 6-[3-(3,5-dichlorophenyl)-3-(trifluoromethyl)pyrrolidin-1-yl]-N-[(4R)-2-(dimethylsulfamoyl)isoxazolidin-4-yl]-4-methyl-pyridine-3-carboxamide | B | 1.72 | 595.10 |
| A16 | 6-[3-(3,5-dichlorophenyl)-3-(trifluoromethyl)pyrrolidin-1-yl]-N-[(4R)-2-(dimethylsulfamoyl)isoxazolidin-4-yl]-2-methyl-pyridine-3-carboxamide | B | 1.81 | 595.10 |
| A17 | 6-[5-(3,5-dichlorophenyl)-5-(trifluoromethyl)-2H-furan-3-yl]-N-[(4R)-2-(dimethylsulfamoyl)isoxazolidin-4-yl]-2-methyl-pyridine-3-carboxamide | B | 2.02 | 594.07 |

BIOLOGICAL EXAMPLES

These Examples illustrate the pesticidal/insecticidal properties of compounds of formula (I).

Tests were performed as follows:

*Diabrotica Balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:

A1, A2, A3, A4, A5, A6, A7, A8, A9, A10, A11, A12, A13, A14, A15, A16, A17.

*Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A1, A2, A3, A4, A5, A6, A7, A8, A9, A10, A11, A12, A13, A14, A15, A16, A17.

*Myzus persicae* (Green Peach Aphid). Intrinsic Activity

Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:

A1, A2, A3, A4, A5, A6, A7, A8.

*Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:

A2, A4, A5, A7, A8, A10, A11, A12, A13, A14, A16.

*Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A1, A2, A3, A4, A5, A6, A7, A8, A9, A10, A11, A12, A13, A14, A15, A16, A17.

*Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:

A1, A2, A3, A4, A5, A6, A7, A8, A9, A10, A11, A12, A13, A14, A15, A16, A17.$

*Tetranychus urticae* (Two-Spotted Spider Mite): Feeding/Contact Activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:

A1, A2, A3, A4, A5, A6, A7, A8, A9, A10, A11, A12, A13, A14, A15, A16, A17.

*Thrips tabaci* (Onion *thrips*) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation.

The following compounds resulted in at least 80% mortality at an application rate of 200 ppm:

A1, A2, A3, A4, A5, A6, A7, A8, A9, A10, A11, A12, A13, A14, A16, A17.

The invention claimed is:

1. A compound of formula (I)

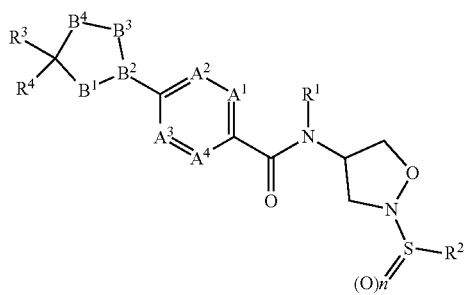

(I)

wherein $A^1, A^2, A^3$ and $A^4$ are independently of one another C—H, C—$R^5$, or nitrogen;

$B^1$-$B^2$-$B^3$-$B^4$ is —C($R^{5a}R^{5b}$)—C=N—O—, —CH$_2$—C=N—CH$_2$—, —CH$_2$—C=CH$_2$—S—, —CH$_2$—C=N—S—, —CH$_2$—N—CH$_2$—CH$_2$—, —CH$_2$—C=CH—O—, —CH(OH)—N—CH$_2$—CH$_2$—, —C(O)—N—CH$_2$—CH$_2$—, —CH$_2$—C=N—O— or —CH=C—CH$_2$—O—;

$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl, or $C_1$-$C_8$alkoxycarbonyl;

$R^2$ is $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —N($R^8$)($R^9$), —OR$^{10}$ or halogen;

$R^3$ is $C_1$-$C_8$haloalkyl;

$R^4$ is aryl, aryl substituted by one to three $R^7$, heteroaryl or heteroaryl substituted by one to three $R^7$;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH=CH—CH=CH— bridge, a —CH$_2$—CH$_2$—CH$_2$— bridge, a —CH(OH)—CH$_2$—CH$_2$— bridge, a —C(O)—CH$_2$—CH$_2$— bridge, or a —N=CH—CH=CH— bridge;

$R^{5a}$ and $R^{5b}$ are, independently of each other, hydrogen, cyano, halogen, hydroxyl, $C_1$-$C_8$alkyl-, $C_1$-$C_8$alkyl-substituted by one to five $R^{6a}$, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, arylthio- or arylthio- wherein the aryl moiety is substituted by one to five $R^7$, arylsulfinyl- or arylsulfinyl- wherein the aryl moiety is substituted by one to five $R^7$, arylsulfonyl- or arylsulfonyl- wherein the aryl moiety is substituted by one to five $R^7$, heterocyclylthio- or heterocyclylthio- wherein the heterocyclyl moiety is substituted by one to five $R^7$, heterocyclylsulfinyl- or heterocyclylsulfinyl- wherein the heterocyclyl moiety is substituted by one to five $R^7$, or heterocyclylsulfonyl- or heterocyclylsulfonyl- wherein the heterocyclyl moiety is substituted by one to five $R^7$, $C_1$-$C_8$alkyl, $C_2$-$C_8$alkenyl, $C_2$-$C_8$alkynyl, $C_1$-$C_8$haloalkyl, $C_2$-$C_8$haloalkenyl, hydroxy, $C_1$-$C_8$alkoxy, $C_3$-$C_8$alkenyloxy, $C_3$-$C_8$alkynyloxy, or $C_1$-$C_8$haloalkoxy, provided that at least one of $R^{5a}$ and $R^{5b}$ is not hydrogen;

$R^{6a}$ is independently cyano, nitro, amino, $C_1$-$C_8$alkylamino, N,N—$C_1$-$C_8$dialkylamino, hydroxy, $C_1$-$C_8$alkoxy, or $C_1$-$C_8$haloalkoxy;

$R^{6b}$ is independently halogen, cyano, nitro, oxo, $C_1$-$C_8$alkyl, $C_1$-$C_8$haloalkyl, amino, $C_1$-$C_8$alkylamino, N,N—$C_1$-$C_8$dialkylamino, hydroxyl, $C_1$-$C_8$alkoxy, $C_1$-$C_8$haloalkoxy, phenyl, phenyl substituted by one to three $R^7$, 5-6 membered heteroaryl, or 5-6 membered heteroaryl substituted by one to three $R^7$;

$R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy;

$R^8$ and $R^9$ are independently hydrogen, cyano, cyano-$C_1$-$C_8$alkyl, $C_1$-$C_8$alkyl, $C_1$-$C_8$alkyl substituted by one to three $R^{6a}$, $C_2$-$C_8$alkenyl, $C_2$-$C_8$alkenyl substituted by one to three $R^{6a}$, $C_1$-$C_8$alkoxy, $C_1$-$C_8$haloalkoxy, $C_1$-$C_8$haloalkoxy substituted by one to three $R^{6a}$, $C_1$-$C_8$alkoxy substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —S(O)$R^{10}$, —S(O)$_2R^{10}$, COR$^{10}$, COOR$^{10}$, or $R^8$ and $R^9$ together with the nitrogen atom can be linked through a $C_3$-$C_8$alkylene chain, a $C_3$-$C_8$alkylene chain substituted by one to three $R^{6b}$ or a $C_3$-$C_8$alkylene chain, where one carbon atom is replaced by O, S, S(O) or SO$_2$;

$R^{10}$ is hydrogen, cyano-$C_1$-$C_8$alkyl, $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-

C₈haloalkyl, C₂-C₈alkenyl, C₂-C₈alkenyl substituted by one to three $R^{6a}$, C₂-C₈haloalkenyl, C₂-C₈haloalkenyl substituted by one to three $R^{6a}$, C₂-C₈alkynyl, C₂-C₈haloalkynyl, phenyl, phenyl substituted by one to three $R^7$, phenyl-C₁-C₄alkyl, phenyl-C₁-C₄alkyl wherein the phenyl moiety is substituted by one to three $R^7$, 5-6 membered heteroaryl, 5-6 membered heteroaryl substituted by one to three $R^7$, 5-6 membered heteroaryl-C₁-C₄alkyl or 5-6 membered heteroaryl-C₁-C₄alkyl wherein the heteroaryl moiety is substituted by one to three $R^7$;

n is 1 or 2;

provided that if $B^1$-$B^2$-$B^3$-$B^4$ is —CH₂—C=N—O— then the only meaning of $R^5$ is that two $R^5$ on adjacent carbon atoms together form a —CH₂—CH₂—CH₂— bridge, a —CH(OH)—CH₂—CH₂— bridge or a —C(O)—CH₂—CH₂— bridge;

and an agrochemically acceptable salt, stereoisomer, enantiomer, tautomer and N-oxide thereof.

2. The compound according to claim 1, wherein $A^1$ is $CR^5$ and $A^2$, $A^3$ and $A^4$ are each CH.

3. The compound according to claim 1, wherein $R^1$ is hydrogen, C₁-C₈alkyl, C₁-C₈alkylcarbonyl- or C₁-C₈alkoxycarbonyl-.

4. The compound of formula (I) according to claim 1, wherein $R^1$ is C₁-C₈alkyl, C₁-C₈alkylcarbonyl-, C₁-C₈alkoxy, C₁-C₈alkoxy-C₁-C₈alkyl, or C₁-C₈alkoxycarbonyl.

5. The compound of formula (I) according to claim 4, wherein $R^1$ is C₁-C₈alkoxy-C₁-C₈alkyl, or C₁-C₈alkoxycarbonyl.

6. The compound of formula (I) according to claim 5, wherein $R^1$ is methoxymethyl, ethoxymethyl, methoxycarbonyl, or ethoxycarbonyl.

7. The compound according to claim 1, wherein $R^2$ is C₁-C₈alkyl or C₁-C₈alkyl substituted by one to three $R^{6a}$, C₁-C₈haloalkyl or C₁-C₈haloalkyl substituted by one to three $R^{6a}$, C₃-C₈cycloalkyl or C₃-C₈cycloalkyl substituted by one to three $R^{6b}$, phenyl, phenyl substituted by one to three $R^7$, phenyl-C₁-C₄alkyl, phenyl-C₁-C₄alkyl wherein the phenyl moiety is substituted by one to three $R^7$, 5-6 membered heteroaryl, 5-6 membered heteroaryl substituted by one to three $R^7$, halogen or —N($R^8$)($R^9$) wherein $R^8$, $R^9$, $R^{6a}$ and $R^{6b}$ are as defined in claim 1.

8. The compound according to claim 1, wherein $R^3$ is C₁-C₄haloalkyl.

9. The compound according to claim 1, wherein $R^4$ is phenyl or phenyl substituted by one to three $R^7$; wherein $R^7$ is independently halogen, cyano, C₁-C₈alkyl, C₁-C₈haloalkyl, C₁-C₈alkoxy, or C₁-C₈haloalkoxy.

10. The compound according to claim 1, wherein $A^1$ is $CR^5$ and $A^2$, $A^3$ and $A^4$ are each CH; $R^1$ is hydrogen; $R^2$ is C₁-C₄alkyl, C₁-C₄alkyl substituted by one to three $R^{6a}$, C₂-C₄alkenyl, C₂-C₄alkynyl, C₃-C₅cycloalkyl, C₁-C₄haloalkyl, di-C₁-C₄alkylamino, C₁-C₄alkylamino, fluoro, 1-3 halo-substituted phenyl, or 5-6 membered heteroaryl; $R^3$ is chlorodifluoromethyl or trifluoromethyl; $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro phenyl or 3,4,5-trichloro-phenyl; and n is 2; wherein $R^5$ is bromo, chloro, fluoro, cyano, methyl, ethyl, trifluoromethyl, cyclopropyl, or vinyl; $R^{6a}$ is independently fluoro, cyano, methoxy, difluoromethoxy or trifluoromethoxy; and $R^{6b}$ is independently bromo, chloro, fluoro, cyano, methyl, ethyl, trifluoromethyl, methoxy, difluoromethoxy, trifluoromethoxy.

11. The compound according to claim 1, wherein $A^1$ is $CR^5$ and $A^2$, $A^3$ and $A^4$ are each CH; $R^1$ is hydrogen, methyl, ethyl, methylcarbonyl-, or methoxycarbonyl; $R^2$ is C₁-C₈alkyl, C₁-C₈alkyl substituted by one to three $R^{6a}$, C₂-C₈alkenyl, C₂-C₈alkynyl, C₃-C₈cycloalkyl, C₁-C₈haloalkyl, di-C₁-C₈alkylamino, C₁-C₄alkylamino, fluoro, aryl, aryl substituted by one to three $R^{6b}$, 5-6 membered heteroaryl or 5-6 membered heteroaryl substituted by one to three $R^{6b}$; $R^3$ is C₁-C₄haloalkyl; $R^4$ is aryl or aryl substituted by one to three $R^{6b}$; and n is 2; wherein $R^5$ is halogen or C₁-C₈alkyl, C₃-C₈cycloalkyl, C₁-C₈haloalkyl, or C₂-C₈alkenyl; $R^{6a}$ is independently cyano, halogen, C₁-C₄alkoxy, or C₁-C₄haloalkoxy; and $R^{6b}$ is independently halogen, cyano, C₁-C₄alkyl, or C₁-C₄haloalkyl, C₁-C₄alkoxy, or C₁-C₄haloalkoxy.

12. The compound according to claim 1, wherein $R^{5a}$ is halogen, hydroxyl, C₁-C₈alkylthio-, C₁-C₈haloalkylthio-, C₁-C₈alkylsulfinyl-, C₁-C₈haloalkylsulfinyl-, C₁-C₈alkylsulfonyl-, C₁-C₈haloalkylsulfonyl-, C₁-C₈alkyl, C₂-C₈alkenyl, C₂-C₈alkynyl, C₁-C₈haloalkyl, C₂-C₈haloalkenyl; $R^{5b}$ is halogen or hydrogen.

13. A method of combating and/or controlling an invertebrate animal pest which comprises applying to the pest, to a locus of the pest, or to a plant susceptible to attack by the pest a pesticidally effective amount of a compound of formula (I) as defined in claim 1.

14. A pesticidal composition, which comprises a compound of formula (I) according to claim 1 or where appropriate, a tautomer thereof, in each case in free form or in agrochemically utilizable salt form, as active ingredient.

15. A method for controlling pests, which comprises applying a composition according to claim 14 to the pests or their environment with the exception of a method for treatment of the human or animal body by surgery or therapy and diagnostic methods practised on the human or animal body.

16. A method for the protection of plant propagation material from the attack by pests, which comprises treating the propagation material or the site, where the propagation material is planted, with a composition according to claim 15.

17. A plant propagation material treated with the pesticidal composition described in claim 14.

18. A compound of formula (Int-I)

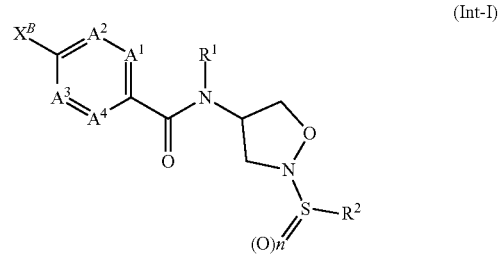

(Int-I)

wherein $A^1$, $A^2$, $A^3$, $A^4$, $R^1$ and $R^2$, are as defined for a compound of formula (I) according to claim 1 and $X^B$ is a leaving group, or $X^B$ is cyano, formyl, CH=N—OH or acetyl, or a tautomer, isomer, enantiomer, salt or N-oxide thereof; or a compound of formula (Int-II)

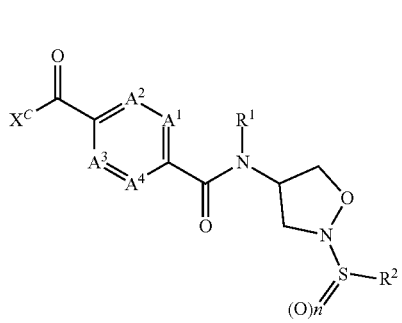
(Int-II)

wherein $A^1$, $A^2$, $A^3$, $A^4$, $R^1$ and $R^2$, are as defined for a compound of formula (I) according to claim 1 and $X^C$ is $CH_2$-halogen, $CH=C(R^3)R^4$, or $CH_2C(OH)(R^3)R^4$ wherein $R^3$ and $R^4$ are as defined for a compound of formula (I) according to claim 1, or a tautomer, isomer, enantiomer, salt or N-oxide thereof; or a compound of formula (Int-III)

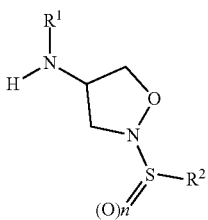
(Int-III)

wherein R and $R^2$, are as defined for a compound of formula (I) according to claim 1, or a tautomer, isomer, enantiomer, salt or N-oxide thereof; or a compound of formula (Int-IV)

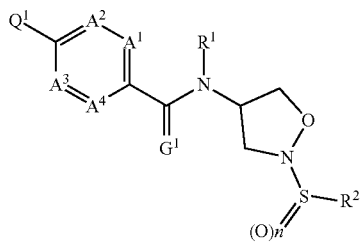
(Int-IV)

wherein $Q^1$ is $CO_2H$ or $NH_2$, and wherein $A^1$, $A^2$, $A^3$, $A^4$, $G^1$, $R^1$, n and $R^2$ are as defined for a compound of formula (I) according to claim 1, or a tautomer, isomer, enantiomer, salt or N-oxide thereof; or a compound of formula (Int-V)

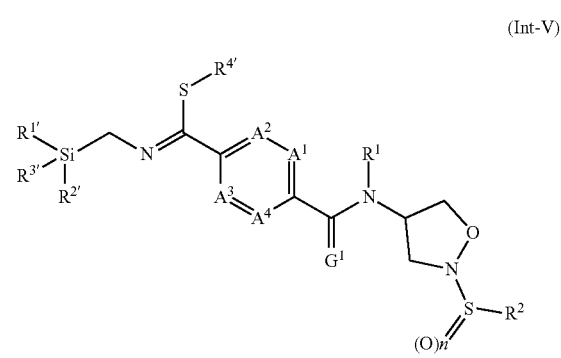
(Int-V)

wherein $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for a compound of formula (I) according to claim 1, or a tautomer, isomer, enantiomer, salt or N-oxide thereof; or a compound of formula (Int-VI)

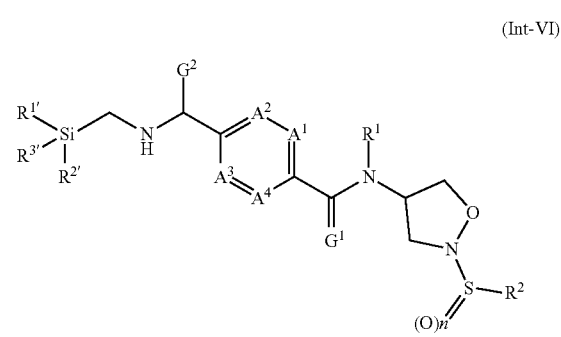
(Int-VI)

wherein $G^2$ is O or S, $R^{1'}$, $R^{2'}$ and $R^{3'}$ are independently of each other optionally substituted alkyl or optionally substituted phenyl, and $A^1$, $A^2$, $A^3$, $A^4$, $G^1$, $R^1$, n and $R^2$ are as defined for a compound of formula (I) according to claim 1, or a tautomer, isomer, enantiomer, salt or N-oxide thereof; or a compounds of formula (Int-VII)

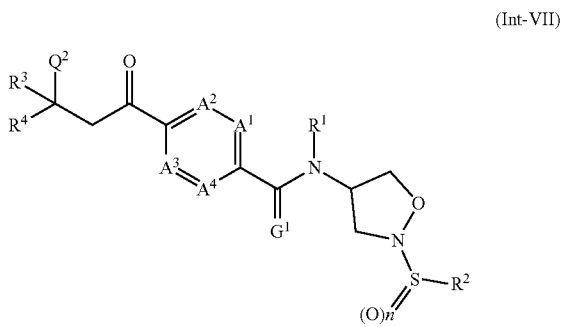
(Int-VII)

wherein $Q^2$ is $CH_2-NO_2$, CN or group Qa

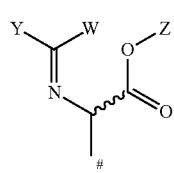
(Qa)

W is hydrogen or optionally substituted aryl, Y is optionally substituted aryl, and Z is optionally substituted alkyl or optionally substituted arylalkylene, and $A^1$, $A^2$, $A^3$, $A^4$, $G^1$, $R^1$, $R^2$, $R^3$, $R^4$ and n are as defined for a compound of formula (I) according to claim 1, or a tautomer, isomer, enantiomer, salt or N-oxide thereof; or a compound of formula (Int-VIII)

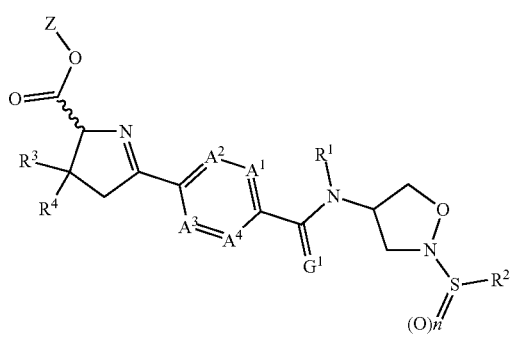
(Int-VIII)

wherein Z is optionally substituted alkyl or optionally substituted arylalkylene, and $A^1$, $A^2$, $A^3$, $A^4$, $G^1$, $R^1$, $R^2$, $R^3$, $R^4$ and n are as defined for a compound of formula (I) according to claim 1, or a tautomer, isomer, enantiomer, salt or N-oxide thereof; or a compound of formula (Int-IX)

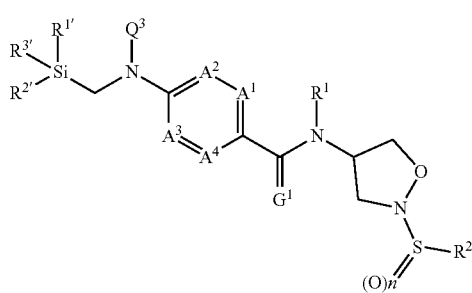
(Int-IX)

wherein $Q^3$ is $CH_2-OR^{4'}$ or $CH_2-CN$, $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for a compound of formula (I) according to claim 1, or a tautomer, isomer, enantiomer, salt or N-oxide thereof; or a compound of formula (Int-X)

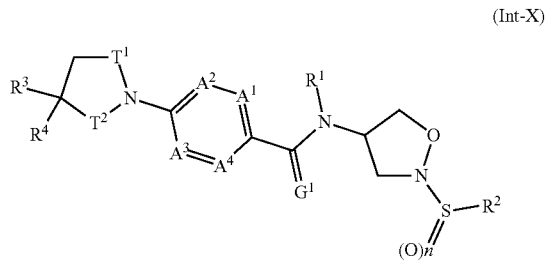
(Int-X)

wherein $T^1$ and $T^2$ are independently $CH_2$ or C=O or CHOH, providing that at least one of $T^1$ and $T^2$ is C=O or CHOH, and $A^1$, $A^2$, $A^3$, $A^4$, $G^1$, $R^1$, $R^2$, $R^3$, $R^4$ and n are as defined for a compound of formula (I) according to claim 1, or a tautomer, isomer, enantiomer, salt or N-oxide thereof.

19. The compound according to claim 18, wherein the compound is selected from the compound of formula (Int-IV), the compound of formula (Int-V), the compound of formula (Int-VI), the compound of formula (Int-VII), the compound of formula (Int-VIII), the compound of A formula (Int-IX), or the compound of formula (Int-X).

20. A compound of formula (I)

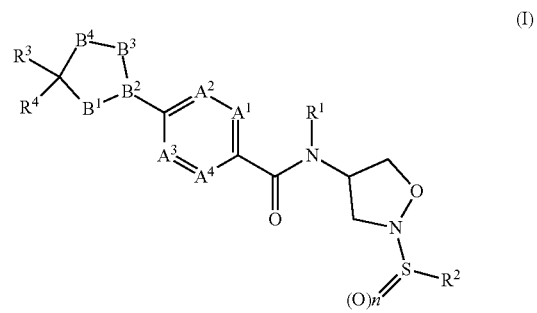
(I)

wherein
$A^1$, $A^2$, $A^3$ and $A^4$ are independently of one another C—H, C—$R^5$, or nitrogen;
$B^1$-$B^2$-$B^3$-$B^4$ is —C($R^{5a}R^{5b}$)—C=N—O—, —$CH_2$—C=N—$CH_2$—, —$CH_2$—C=CH—S—, —$CH_2$—C=N—S—, —$CH_2$—N—$CH_2$—$CH_2$—, —$CH_2$—C=CH—O—, —CH(OH)—N—$CH_2$—$CH_2$—, —C(O)—N—$CH_2$—$CH_2$—, —$CH_2$—C=N—O— or —CH=C—$CH_2$—O—;
$R^1$ is $C_3$-$C_6$cycloalkylcarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl,
wherein each alkyl or alkoxy group may be optionally substituted with from one to three halogen atoms or with a cyano group; or
$R^1$ is $C_1$-$C_8$alkyl, $C_1$-$C_8$alkylcarbonyl-, $C_1$-$C_8$alkoxy, $C_1$-$C_8$alkoxy-$C_1$-$C_8$alkyl, or $C_1$-$C_8$alkoxycarbonyl-, wherein each alkyl or alkoxy group is substituted with from one to three halogen atoms or with a cyano group;
$R^2$ is $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —N($R^8$)($R^9$), —O$R^{10}$ or halogen;

$R^3$ is $C_1$-$C_8$haloalkyl;

$R^4$ is aryl, aryl substituted by one to three $R^7$, heteroaryl or heteroaryl substituted by one to three $R^7$;

$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH═CH—CH═CH— bridge, a —CH$_2$—CH$_2$—CH$_2$— bridge, a —CH(OH)—CH$_2$—CH$_2$— bridge, a —C(O)—CH$_2$—CH$_2$— bridge, or a —N═CH—CH═CH— bridge;

$R^{5a}$ and $R^{5b}$ are, independently of each other, hydrogen, cyano, halogen, hydroxyl, $C_1$-$C_8$alkyl-, $C_1$-$C_8$alkyl- substituted by one to five $R^{6a}$, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, arylthio- or arylthio- wherein the aryl moiety is substituted by one to five $R^7$, arylsulfinyl- or arylsulfinyl- wherein the aryl moiety is substituted by one to five $R^7$, arylsulfonyl- or arylsulfonyl- wherein the aryl moiety is substituted by one to five $R^7$, heterocyclylthio- or heterocyclylthio- wherein the heterocyclyl moiety is substituted by one to five $R^7$, heterocyclylsulfinyl- or heterocyclylsulfinyl- wherein the heterocyclyl moiety is substituted by one to five $R^7$, or heterocyclylsulfonyl- or heterocyclylsulfonyl- wherein the heterocyclyl moiety is substituted by one to five $R^7$, $C_1$-$C_8$alkyl, $C_2$-$C_8$alkenyl, $C_2$-$C_8$alkynyl, $C_1$-$C_8$haloalkyl, $C_2$-$C_8$haloalkenyl, hydroxy, $C_1$-$C_8$alkoxy, $C_3$-$C_8$alkenyloxy, $C_3$-$C_8$alkynyloxy, or $C_1$-$C_8$haloalkoxy, provided that at least one of $R^{5a}$ and $R^{5b}$ is not hydrogen;

$R^{6a}$ is independently cyano, nitro, amino, $C_1$-$C_8$alkylamino, N,N—$C_1$-$C_8$dialkylamino, hydroxy, $C_1$-$C_8$alkoxy, or $C_1$-$C_8$haloalkoxy;

$R^{6b}$ is independently halogen, cyano, nitro, oxo, $C_1$-$C_8$alkyl, $C_1$-$C_8$haloalkyl, amino, $C_1$-$C_8$alkylamino, N,N—$C_1$-$C_8$dialkylamino, hydroxyl, $C_1$-$C_8$alkoxy, $C_1$-$C_8$haloalkoxy, phenyl, phenyl substituted by one to three $R^7$, 5-6 membered heteroaryl, or 5-6 membered heteroaryl substituted by one to three $R^7$;

$R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy;

$R^8$ and $R^9$ are independently hydrogen, cyano, cyano-$C_1$-$C_8$alkyl, $C_1$-$C_8$haloalkyl, $C_1$-$C_8$alkyl substituted by one to three $R^{6a}$, $C_2$-$C_8$alkenyl, $C_2$-$C_8$alkenyl substituted by one to three $R^{6a}$, $C_1$-$C_8$alkoxy, $C_1$-$C_8$haloalkoxy, $C_1$-$C_8$haloalkoxy substituted by one to three $R^{6a}$, $C_1$-$C_8$alkoxy substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl, 5-6 membered heteroaryl-$C_1$-$C_4$alkyl wherein the heteroaryl moiety is substituted by one to three $R^7$, —S(O)$R^{10}$, —S(O)$_2R^{10}$, CO$R^{10}$, COO$R^{10}$, or $R^8$ and $R^9$ together with the nitrogen atom can be linked through a $C_3$-$C_8$alkylene chain, a $C_3$-$C_8$alkylene chain substituted by one to three $R^{6b}$ or a $C_3$-$C_8$alkylene chain, where one carbon atom is replaced by O, S, S(O) or SO$_2$;

$R^{10}$ is hydrogen, cyano-$C_1$-$C_8$alkyl, $C_1$-$C_8$alkyl, $C_1$-$C_8$alkyl substituted by one to three $R^{6a}$, $C_1$-$C_8$haloalkyl, $C_1$-$C_8$haloalkyl substituted by one to three $R^{6a}$, $C_3$-$C_8$cycloalkyl, $C_3$-$C_8$cycloalkyl substituted by one to three $R^{6b}$, $C_3$-$C_8$cycloalkyl where one carbon atom is replaced by O, S, S(O) or SO$_2$, $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or SO$_2$, $C_3$-$C_8$cycloalkyl-$C_1$-$C_8$haloalkyl, $C_2$-$C_8$alkenyl, $C_2$-$C_8$alkenyl substituted by one to three $R^{6a}$, $C_2$-$C_8$haloalkenyl, $C_2$-$C_8$haloalkenyl substituted by one to three $R^{6a}$, $C_2$-$C_8$alkynyl, $C_2$-$C_8$haloalkynyl, phenyl, phenyl substituted by one to three $R^7$, phenyl-$C_1$-$C_4$alkyl, phenyl-$C_1$-$C_4$alkyl wherein the phenyl moiety is substituted by one to three $R^7$, 5-6 membered heteroaryl, 5-6 membered heteroaryl substituted by one to three $R^7$, 5-6 membered heteroaryl-$C_1$-$C_4$alkyl or 5-6 membered heteroaryl-$C_1$-$C_4$alkyl wherein the heteroaryl moiety is substituted by one to three $R^7$;

n is 1 or 2;

provided that if $B^1$-$B^2$-$B^3$-$B^4$ is —CH$_2$—C═N—O— then the only meaning of $R^5$ is that two $R^5$ on adjacent carbon atoms together form a —CH$_2$—CH$_2$—CH$_2$— bridge, a —CH(OH)—CH$_2$—CH$_2$— bridge or a —C(O)—CH$_2$—CH$_2$— bridge;

and an agrochemically acceptable salt, stereoisomer, enantiomer, tautomer and N-oxide thereof.

21. The compound of formula (I) according to claim 20, wherein $R^1$ is $C_3$-$C_6$cycloalkylcarbonyl, $C_1$-$C_8$alkylcarbonyloxy$C_1$-$C_8$alkyl, $C_1$-$C_8$alkoxycarbonylsulfanyl, $C_1$-$C_8$alkylaminocarbonyloxy$C_1$-$C_8$alkyl, $C_1$-$C_8$dialkylaminocarbonyloxy$C_1$-$C_8$alkyl, $C_1$-$C_8$alkylaminocarbonyl$C_1$-$C_8$alkyl, $C_1$-$C_8$dialkylaminocarbonyl$C_1$-$C_8$alkyl or $C_1$-$C_8$alkoxycarbonyl$C_1$-$C_8$alkylamino$C_1$-$C_8$alkyl, wherein each alkyl or alkoxy group may be optionally substituted with from one to three halogen atoms; or $R^1$ is $C_1$-$C_8$alkyl, $C_1$-$C_8$alkylcarbonyl-, $C_1$-$C_8$alkoxy, $C_1$-$C_8$alkoxy-$C_1$-$C_8$alkyl, or C1-$C_8$alkoxycarbonyl wherein each alkyl or alkoxy group is substituted with from one to three halogen atoms.

22. The compound of formula (I) according to claim 21, wherein $R^1$ is $C_1$-$C_8$cyanoalkyl, or $C_1$-$C_8$alkylcarbonyloxy$C_1$-$C_8$alkyl.

23. The compound of formula (I) according to claim 21, wherein $R^1$ is cyanomethyl, methylcarbonyloxymethyl, 1-methylethylcarbonyloxymethyl or 1,1-dimethylethylcarbonyloxymethyl.

24. A compound of formula (Int-I)

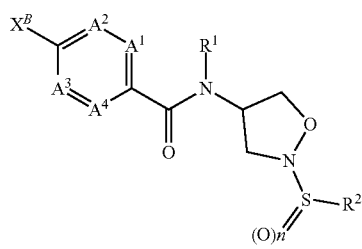
(Int-I)

wherein $A^1$, $A^2$, $A^3$, $A^4$, $R^1$ and $R^2$, are as defined for compound of formula (I) according to claim 20 and $X^B$ is a leaving group, or $X^B$ is cyano, formyl, CH=N—OH or acetyl, or a tautomer, isomer, enantiomer, salt or N-oxide thereof; or a compound of formula (Int-II)

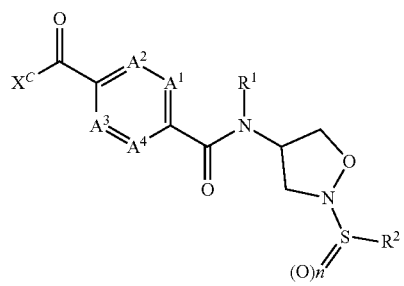
(Int-II)

wherein $A^1$, $A^2$, $A^3$, $A^4$, $R^1$ and $R^2$, are as defined for a compound of formula (I) according to claim 20 and $X^C$ is $CH_2$-halogen, CH=C($R^3$)$R^4$, or $CH_2$C(OH)($R^3$)$R^4$ wherein $R^3$ and $R^4$ are as defined for a compound of formula (I) according to claim 20, or a tautomer, isomer, enantiomer, salt or N-oxide thereof; or a compound of formula (Int-III)

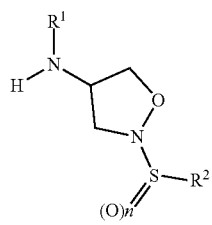
(Int-III)

wherein R and $R^2$, are as defined for compound of formula (I) according to claim 20, or a tautomer, isomer, enantiomer, salt or N-oxide thereof; or a compound of formula (Int-IV)

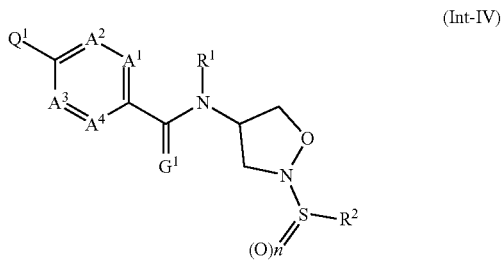
(Int-IV)

wherein $Q^1$ is $CO_2H$ or $NH_2$, and wherein $A^1$, $A^2$, $A^3$, $A^4$, $G^1$, $R^1$, n and $R^2$ are as defined for compound of formula (I) according to claim 20, or a tautomer, isomer, enantiomer, salt or N-oxide thereof; or a compound of formula (Int-V)

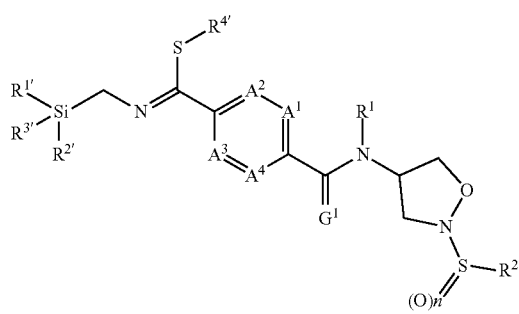
(Int-V)

wherein $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for the compound of formula (I) according to claim 20 or a tautomer, isomer, enantiomer, salt or N-oxide thereof; or a compound of formula (Int-VI)

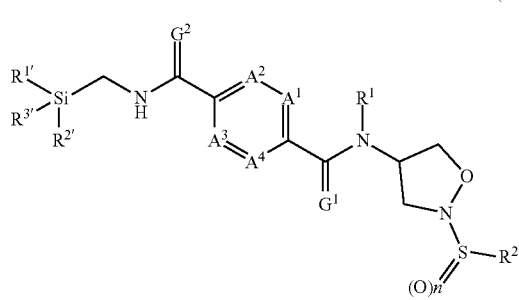
(Int-VI)

wherein $G^2$ is O or S, $R^{1'}$, $R^{2'}$ and $R^{3'}$ are independently of each other optionally substituted alkyl or optionally substituted phenyl, and $A^1$, $A^2$, $A^3$, $A^4$, $G^1$, $R^1$, n and $R^2$ are as defined for the compound of formula (I) according to claim 20, or a tautomer, isomer, enantiomer, salt or N-oxide thereof; or a compounds of formula (Int-VII)

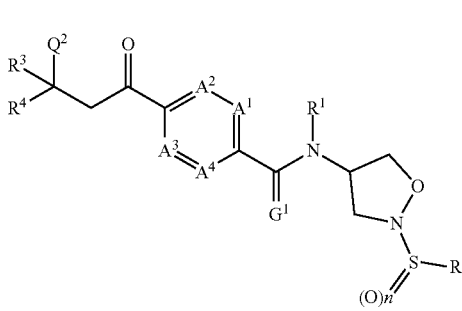
(Int-VII)

wherein $Q^2$ is $CH_2$—$NO_2$, CN or group Qa

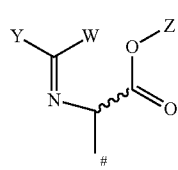
(Qa)

W is hydrogen or optionally substituted aryl, Y is optionally substituted aryl, and Z is optionally substituted alkyl or optionally substituted arylalkylene, and $A^1$, $A^2$, $A^3$, $A^4$, $G^1$, $R^1$, $R^2$, $R^3$, $R^4$ and n are as defined for the compound of formula (I) according to claim 20, or a tautomer, isomer, enantiomer, salt or N-oxide thereof; or a compound of formula (Int-VIII)

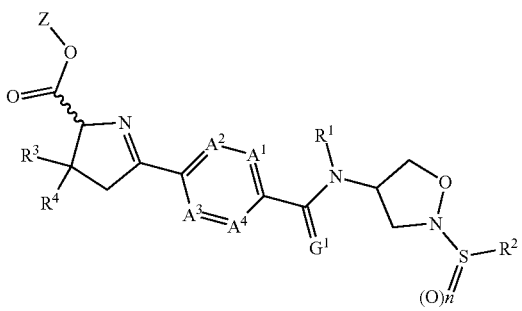
(Int-VIII)

wherein Z is optionally substituted alkyl or optionally substituted arylalkylene, and $A^1$, $A^2$, $A^3$, $A^4$, $G^1$, $R^1$, $R^2$, $R^3$, $R^4$ and n are as defined for the compound of formula (I) according to claim 20, or a tautomer, isomer, enantiomer, salt or N-oxide thereof; or a compound of formula (Int-IX)

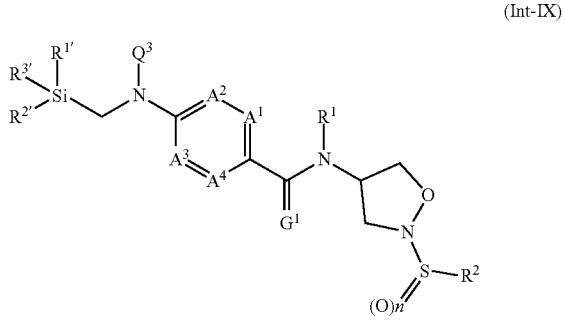
(Int-IX)

wherein $Q^3$ is $CH_2$—$OR^{4'}$ or $CH_2$—CN, $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, $R^1$, n and $R^2$ are as defined for the compound of formula (I) according to claim 20, or a tautomer, isomer, enantiomer, salt or N-oxide thereof; or a compound of formula (Int-X)

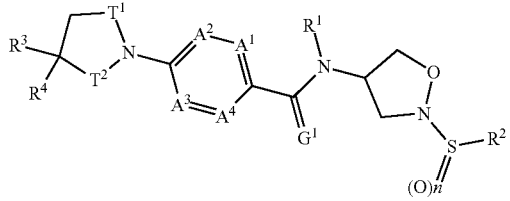
(Int-X)

wherein $T^1$ and $T^2$ are independently $CH_2$ or C=O or CHOH, providing that at least one of T and $T^2$ is C=O or CHOH, and $A^1$, $A^2$, $A^3$, $A^4$, $G^1$, $R^1$, $R^2$, $R^3$, $R^4$ and n are as defined for the compound of formula (I) according to claim 20, or a tautomer, isomer, enantiomer, salt or N-oxide thereof.

25. The compound according to claim 24, wherein the compound is selected from the compound of formula (Int-IV), the compound of formula (Int-V), the compound of formula (Int-VI), the compound of formula (Int-VII), the compound of formula (Int-VIII), the compound of A formula (Int-IX), or the compound of formula (Int-X).

\* \* \* \* \*